(12) United States Patent
Pihlavisto et al.

(10) Patent No.: US 9,371,290 B2
(45) Date of Patent: Jun. 21, 2016

(54) PYRIDAZINONE COMPOUNDS

(75) Inventors: Marjo Pihlavisto, Kaarina (FI); David Smith, Naantali (FI); Auni Juhakoski, Raisio (FI); Ferenc Fulop, Szeged (HU); Laszlo Lazar, Szeged (HU); Istvan Szatmari, Szeged (HU); Ferenc Miklos, Szeged (HU); Zsolt Szakonyi, Szeged (HU); Lorand Kiss, Szeged (HU); Marta Palko, Szeged (HU)

(73) Assignee: BIOTIE THERAPIES CORPORATION, Turku (FI)

( * ) Notice: Subject to any disclaimer, the term of this patent is extended or adjusted under 35 U.S.C. 154(b) by 0 days.

(21) Appl. No.: 14/003,626

(22) PCT Filed: Mar. 6, 2012

(86) PCT No.: PCT/FI2012/050220
§ 371 (c)(1),
(2), (4) Date: Sep. 6, 2013

(87) PCT Pub. No.: WO2012/120195
PCT Pub. Date: Sep. 13, 2012

(65) Prior Publication Data
US 2014/0024648 A1  Jan. 23, 2014

Related U.S. Application Data

(60) Provisional application No. 61/450,352, filed on Mar. 8, 2011.

(30) Foreign Application Priority Data

Mar. 8, 2011 (FI) ..................... 20115234

(51) Int. Cl.
| | | |
|---|---|---|
| *A61K 31/50* | (2006.01) | |
| *A61K 31/501* | (2006.01) | |
| *C07D 401/00* | (2006.01) | |
| *C07D 403/00* | (2006.01) | |
| *C07D 405/00* | (2006.01) | |
| *C07D 409/00* | (2006.01) | |
| *C07D 237/24* | (2006.01) | |
| *C07D 405/14* | (2006.01) | |
| *C07D 401/04* | (2006.01) | |
| *C07D 403/04* | (2006.01) | |
| *C07D 405/04* | (2006.01) | |
| *C07D 409/04* | (2006.01) | |
| *C07D 413/04* | (2006.01) | |
| *C07D 401/14* | (2006.01) | |
| *A61K 31/5377* | (2006.01) | |
| *A61K 45/06* | (2006.01) | |
| *C07D 237/16* | (2006.01) | |
| *C07D 403/12* | (2006.01) | |
| *C07D 403/14* | (2006.01) | |
| *G01N 33/50* | (2006.01) | |

(52) U.S. Cl.
CPC .............. *C07D 237/24* (2013.01); *A61K 31/50* (2013.01); *A61K 31/501* (2013.01); *A61K 31/5377* (2013.01); *A61K 45/06* (2013.01); *C07D 237/16* (2013.01); *C07D 401/04* (2013.01); *C07D 401/14* (2013.01); *C07D 403/04* (2013.01); *C07D 403/12* (2013.01); *C07D 403/14* (2013.01); *C07D 405/04* (2013.01); *C07D 405/14* (2013.01); *C07D 409/04* (2013.01); *C07D 413/04* (2013.01); *G01N 33/502* (2013.01)

(58) Field of Classification Search
None
See application file for complete search history.

(56) References Cited

U.S. PATENT DOCUMENTS

| | | |
|---|---|---|
| 2005/0250782 A1 | 11/2005 | Marlow et al. |
| 2009/0163545 A1 | 6/2009 | Goldfarb |
| 2009/0318455 A1 | 12/2009 | Kossen et al. |
| 2010/0190731 A1 | 7/2010 | Olgin et al. |

FOREIGN PATENT DOCUMENTS

| | | |
|---|---|---|
| EP | 1 847 535 A1 | 10/2007 |
| JP | 2003-040872 A | 2/2003 |

(Continued)

OTHER PUBLICATIONS

Birkinshaw, et. al., Biochemical Journal (1936), 30, 394-411.*

(Continued)

*Primary Examiner* — Jeffrey H Murray
(74) *Attorney, Agent, or Firm* — Birch, Stewart, Kolasch & Birch, LLP

(57) ABSTRACT

The invention relates to pyridazinone and pyridone compounds having formula (I) or (I'), and pharmaceutically acceptable salts, hydrates, and solvates thereof (I) wherein $R_1/R_4$ and X and $X_3$ are as defined in the claims. The invention further relates to their use as inhibitors of copper-containing amine oxidases. The present invention also relates to the preparation of the aforementioned compounds and to pharmaceutical compositions comprising as an active ingredient(s) one or more of the aforementioned compounds, pharmaceutically acceptable salts, hydrates, or solvates thereof.

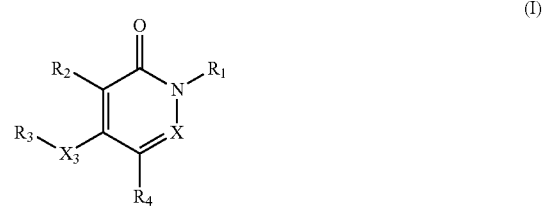

(I)

17 Claims, 1 Drawing Sheet

(56) References Cited

FOREIGN PATENT DOCUMENTS

| WO | WO 2004/072029 A2 | 8/2004 |
|---|---|---|
| WO | WO 2008/115381 A1 | 9/2008 |
| WO | WO 2010/029379 A1 | 3/2010 |
| WO | WO 2010/135470 A1 | 11/2010 |

OTHER PUBLICATIONS

Shober, et. al., Journal of Heterocyclic Chemistry (1990), 27(3), 471-7.*

Bestmann et al., "Phosphacumulen-Ylide als Cyclisierungsbausteine in der Heterocyclensynthese", Chem. Ber., vol. 118, 1985, pp. 1709-1719.

Birkinshaw et al., "LXIV. Studies in the Biochemistry of Micro-Organisms. XLVIII. Penicillic Acid, A Metabolic Product of Penicillium Puberulum Bainier and P. Cyclopium Westling", Biochem. J., 1936, vol. 30, No. 3, pp. 394-411.

Extended European Search Report, dated Jul. 1, 2014, for European Application No. 12754287.6.

Mohareb et al., "Novel Synthesis of 4-Bromo-3-Oxo-2-Phenylhydrazono-Butyronitrile and 4-Cyano-3-Oxo-2-Phenylhydrazono-Butyronitrile: Synthesis of Pyridazine, Thiazole, 1, 2, 4-Triazine and Pyrido[2,3-e]-1,2,4-Triazine Der.", Coll. Czech. Chem. Commun., vol. 57, 1992, pp. 1759-1769.

Schober et al., "Pyridazines with Heteroatom Substituents in Position 3 and 5.3 [1]. 2-Aryl-5-hydroxypyridazin-3(2H)-ones as Potential Herbicides: Synthesis and Some Reactions", J. Heterocyclic Chem., vol. 26, Jan.-Feb. 1989, pp. 169-176, XP2051833.

Bowden et al., "Structure-activity relations. Part 16. Biologically active 2,4-diphenylphthalazin-1(2H)-ones and 2,6-diphenylpyridazin-3(2H)-ones," Journal of Serbian Chemical Society, 1997, vol. 62, No. 10, pp. 951-955.

El-Mobayed et al., "Effect of Solvent on the Product Formation in the Reaction of Hydrazines with β-Aroyl-α-[4(1,3-Disubstituted-2-Pyrazolin-5-One)] Propionic Acids," Arab Gulf Journal for Scientific Research, 1990, vol. 8, No. 3, pp. 29-38.

Fahmy et al., "Activated Nitriles in Heterocyclic Synthesis: A Novel Synthesis of Pyridine and Pyridazine Derivatives," Communications, Dec. 1985, pp. 1135-1137.

Finnish Search Report issued in FI20115234 on Jan. 23, 2012.

International Search Report issued in PCT/FI2012/050220, mailed on Jun. 28, 2012.

Lyubchanskaya et al., "Synthesis of functionally substituted dienediamines and study of their chemical transformations," Khimiko-Farmatsevticheskii Zhurnal, 1995, vol. 29, No. 9, pp. 40-43.

Schober et al., "Pyridazines with Hetero-Atom Substituents in Position 3 and 5, Part VII [1]. Halogenation of 2-Aryl-5-hydroxy-pyridazin-3(2H)-ones in Position 4," Monatshefte für Chemie, 1990, vol. 121, pp. 565-569.

Soliman et al., "The Reaction of Hydrazines with β-Aroyl Acrylic Acids and Their Methyl Esters," Egyptian Journal of Chemistry, 1985, vol. 28, No. 4, pp. 311-318.

Zupančič et al., "Transformations of Dialkyl Acetone-1,3-dicarboxylates via Their Dimethylaminomethylidene Derivatives Into 1-substituted 4-ethoxycarbonyl-5-(ethoxycarbonylmethyl)...," Acta Chimica Slovenica, 2008, vol. 55, pp. 1009-1018.

Australian Office Action and Search Report dated Oct. 16, 2015, for Australian Application No. 2012224499.

Japanese Office Action dated Sep. 8, 2015, for Japanese Application No. 2013-557146 with the English translation.

STN Tokyo, 338405-34-8 Registry, May 25, 2001, 3(2H)-Pyridazinone, 5-phenoxy-2-phenyl-6-(1H-1,2,4-triazol-5-yl), 1 page.

American Chemical Society (ACS), "1-(2,4-dichlorophenyl)-1,6-dihydro-6-oxo-4-phenoxy-3-pyridazinecarbonitrile," CAS Registry No. 338405-51-9, Entered STN: May 25, 2001, Abstract only provided (1 page).

American Chemical Society (ACS), "1-(4-fluorophenyl)-1,6-dihydro-4-methoxy-6-oxo-3-pyridazinecarboxamide," CAS Registry No. 921581-88-6, Entered STN: Feb. 16, 2007, Abstract only provided (1 page).

American Chemical Society (ACS), "1,6-dihydro-4-(methylthio)-6-oxo-1-[3-(trifluoromethyl)phenyl]-3-pyridazinecarbonitrile," CAS Registry No. 400076-82-6, Entered STN: Mar. 11, 2002, Abstract only provided (1 page).

American Chemical Society (ACS), "1,6-dihydro-4-methoxy-1-(4-methylphenyl)-6-oxo-N-propyl-3-pyridazinecarboxamide," CAS Registry No. 921791-97-1, Entered STN: Feb. 19, 2007, Abstract only provided (1 page).

American Chemical Society (ACS), "1,6-dihydro-4-methoxy-6-oxo-1-[3-(trifluoromethyl)phenyl]-3-pyridazinecarbonitrile," CAS Registry No. 306976-47-6, Entered STN: Dec. 6, 2000, Abstract only provided (1 page).

American Chemical Society (ACS), "1,6-dihydro-6-oxo-4-phenoxy-1-phenyl-3-pyridazinecarbonitrile," CAS Registry No. 338748-44-0, Entered STN: May 29, 2001, Abstract only provided (1 page).

American Chemical Society (ACS), "1,6-dihydro-6-oxo-4-phenoxy-1-phenyl-3-pyridazinecarboxamide," CAS Registry No. 338405-11-1, Entered STN: May 25, 2001, Abstract only provided (4 pages).

American Chemical Society (ACS), "1,6-dihydro-6-oxo-4-phenoxy-1-phenyl-3-pyridazinecarboxylic acid hydrazide", CAS Registry No. 338405-08-6, Entered STN: May 25, 2001, Abstract only provided (3 pages).

American Chemical Society (ACS), "4-(4-chlorophenoxy)-1,6-dihydro-6-oxo-1-phenyl-3-pyridazinecarboxamide," CAS Registry No. 338756-29-9, Entered STN: May 29, 2001, Abstract only provided (1 page).

American Chemical Society (ACS), "4-amino-1,6-dihydro-6-oxo-1-phenyl-3-pyridazinecarboxamide," CAS Registry No. 339030-82-9, Entered STN: May 30, 2001, Abstract only provided (1 page).

American Chemical Society (ACS), "N-butyl-1-(4-fluorophenyl)-1,6-dihydro-4-methoxy-6-oxo-3-pyridazinecarboxamide," CAS Registry No. 921792-22-5, Entered STN: Feb. 19, 2007, Abstract only provided (1 page).

* cited by examiner

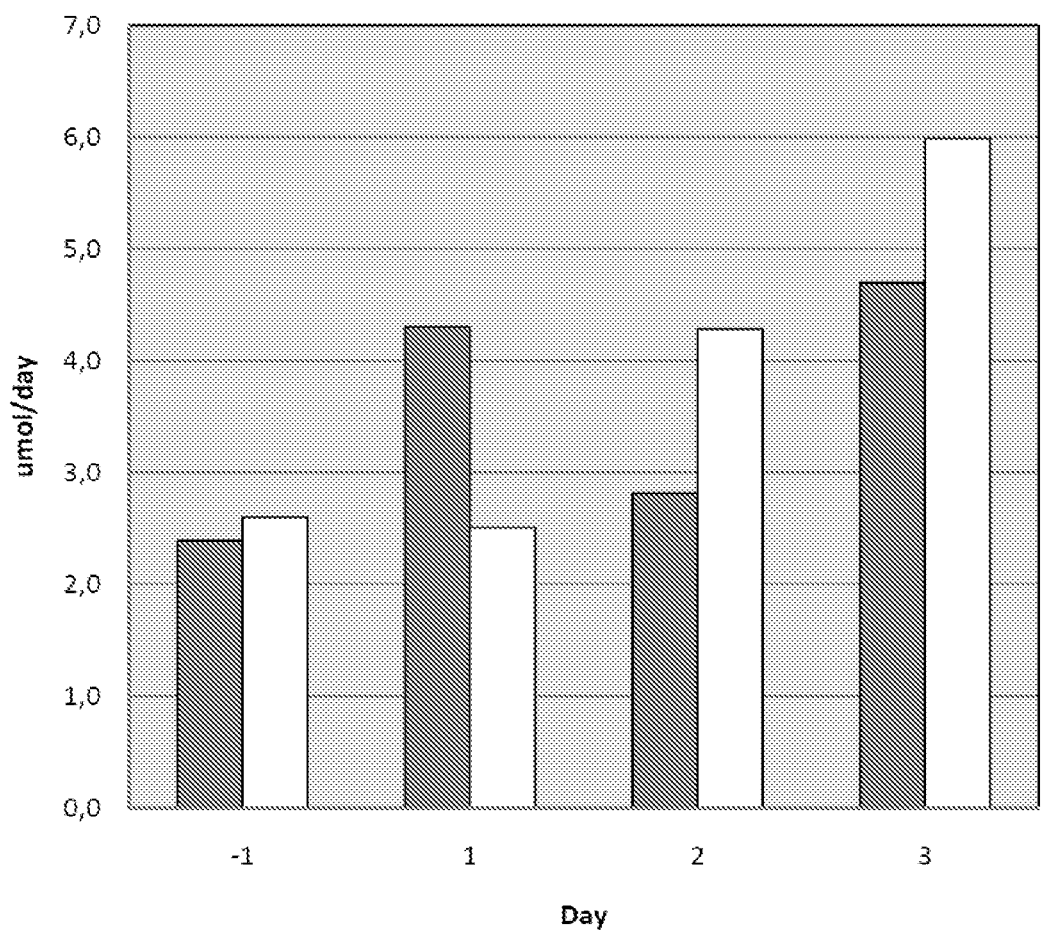

PYRIDAZINONE COMPOUNDS

CROSS REFERENCE TO RELATED APPLICATIONS

This application is the National Phase of PCT/FI2012/050220 filed on Mar. 6, 2012, which claims priority under 35 U.S.C. §119(e) to U.S. Provisional Application No. 61/450,352 filed on Mar. 8, 2011, and under 35 U.S.C. §119(a) to Patent Application No. 20115234 filed in Finland on Mar. 8, 2011, all of which are hereby expressly incorporated by reference into the present application.

FIELD OF THE INVENTION

The present invention is in the field of medicinal chemistry and relates to pyridazinone and pyridone compounds, pharmaceutically acceptable salts, hydrates, and solvates thereof, and their use as inhibitors of copper-containing amine oxidases. The present invention also relates to the preparation of the aforementioned compounds and to pharmaceutical compositions comprising as an active ingredient(s) one or more of the aforementioned compounds, pharmaceutically acceptable salts, hydrates, or solvates thereof.

BACKGROUND OF THE INVENTION

Semicarbazide sensitive amine oxidase (SSAO), also known as vascular adhesion protein-1 (VAP-1) and encoded by the human AOC3 gene, belongs to a family of copper-containing amine oxidases and is a human endothelial cell adhesion molecule with a dual function. On the one hand it has a unique and restricted expression pattern mediating lymphocyte binding to vascular endothelium. The level of SSAO/VAP-1 is upregulated in the vasculature at the sites of inflammation, specifically on the surface of vascular endothelia cells mediating leukocyte entry to inflammatory sites.

On the other hand SSAO/VAP-1 exhibits monoamine oxidase (MAO) activity which is present in the extracellular domain of the protein. SSAO/VAP-1 is distinguished from the widely distributed mitochondrial MAO-A and MAO-B flavoproteins with respect to amino acid sequence, 2,4,5-trihydrooxyphenylalanyl quinone (TPQ) cofactor, biological function, substrates, and subcellular distribution.

SSAO/VAP-1 located on the vascular endothelial cell surface catalyzes the oxidative deamination of primary aliphatic and aromatic monoamines with the following reaction pathway.

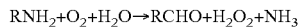

$$RNH_2+O_2+H_2O \rightarrow RCHO+H_2O_2+NH_3$$

The enzymatic reaction of the amine results in the formation of a corresponding aldehyde, $H_2O_2$, and ammonia, which generally are more cytotoxic than the substrates themselves. Products of SSAO/VAP-1 such as formaldehyde are mainly extracellular. The potential toxic effects of formaldehyde towards blood vessels may be amplified by the absence of formaldehyde dehydrogenase from the blood plasma, where SSAO/VAP-1 products are formed.

The physiological substrates of SSAO/VAP-1 in man have not been clearly identified, although methylamine and aminoacetone have been shown to be good substrates for SSAO/VAP-1. Methylamine is a product of various human biochemical pathways for the degradation of creatine, sarcosine, and adrenaline, and is found in various mammalian tissues and in blood. It can also be derived from the diet by gut bacterial degradation of dietary precursors or ingested in food and cigarette smoke. The concentration of methylamine in the blood can be increased in certain physiological and pathological situations such as diabetes.

SSAO/VAP-1 exists as a membrane-bound and a soluble form, which is present in the plasma, and its activity shows wide tissue distribution. The major sources of the enzyme are the endothelial cells, smooth muscle cells, and adipocytes. Since expression of SSAO/VAP-1 is especially remarkable in vascular smooth muscle, endothelium and plasma, cytotoxic effects associated with it may be pronounced in highly vascularised tissues, such as the kidneys and the retina. The amount of soluble SSAO/VAP-1 is elevated in both Type I and Type II diabetes and the increased level of toxic aldehydes and oxygen radicals in the local environment of the endothelial cell produced by the oxidative amination of these substrates could damage the vascular cells leading to vascular damage, which may explain late stage diabetic complications found in these patients. Increased levels of methylamine and aminoacetone have been reported in patients with Type I or Type II diabetes and it has been proposed that the vasculopathies such as retinopathy, neuropathy, and nephropathy and atherosclerosis seen in late stage diabetes could be treated with specific inhibitors of SSAO/VAP-1 activity.

The pathway of leukocyte adhesion to endothelial cells has been proposed to be directly involved with the SSAO/VAP-1 activity by a novel mechanism involving direct interaction with an amine substrate presented on a SSAO/VAP-1 ligand expressed on the surface of a leukocyte. Therefore inhibitors of SSAO/VAP-1 activity could be expected to reduce leukocyte adhesion in areas of inflammation by reducing leukocyte trafficking into the inflamed area and therefore the inflammatory process itself.

Additionally, in human clinical tissue samples the expression of SSAO/VAP-1 is induced at the sites of inflammation. This increased level of SSAO/VAP-1 can further lead to increased production of $H_2O_2$ by the oxidative deamination pathway. $H_2O_2$ is a known signalling molecule upregulating other adhesion molecules. This increased adhesion molecule expression may further lead to enhance leukocyte trafficking into areas where SSAO/VAP-1 is expressed. Thus inhibitors of the enzymatic activity of SSAO/VAP may serve as anti-inflammatory agents.

SSAO/VAP-1 has been proposed as a potential target for the treatment of obesity due to the observation that its expression is induced during adipogenesis. A role for SSAP/VAP-1 in apoptosis has also been proposed. In healthy humans the plasma activity of SSAO/VAP-1 is rather constant. Elevated SSAO/VAP-1 levels or over-expression of the enzyme have been observed in several pathological conditions and diseases including congestive heart failure, end-stage renal disease, multiple sclerosis, psoriasis, Alzheimer's disease, and myopathies and diabetes, inflammatory liver diseases and liver fibrosis.

Due to the proposed involvement of SSAO/VAP-1 in a number of inflammatory processes and various pathologies, inhibitors of SSAO/VAP-1 that can have therapeutic value in the prevention or the treatment of such disorders or diseases are in great demand. Several small-molecule inhibitors of SSAO/VAP-1 have been identified, including hydrazine derivatives, phenylallylhydrazines (WO2006/094201, WO2005/014530), hydrazine alcohols and hydrazine indanes (WO2002/0202090, WO2003/006003, WO2005/08319), arylalkylamines, propenyl- and propargylamines, oxazolidinones, haloalkylamines, 1,3,4-oxadiazines (WO2002/0202541), 4,5,6,7-tetrahydroimidazo-[4,5-c]pyridines (WO2002/0238153, WO2010/031789), pyrazolo[4,3-c]pyridines (WO2010/031791), imidazopyridines (WO2010/064020), thiazole derivates (WO2004/087138, WO2004/

067521, WO2004/067521, WO2006/028269, WO2006/011631), haloallylamines (WO2009/066152), compounds having an oxime moiety (WO2010/09373), and compounds disclosed in WO2005/082343.

Compounds for medicinal use comprising a pyridazinone or pyridinone moiety have been disclosed, including pirfenidone analogs and derivatives (WO2010/135470, US2009/0318455, US2010/0190731) and MEK inhibitors (US2005/0250782).

Known from CAPlus-database and available from commercial sources is 5-phenoxy-2-phenyl-6-(1H-1,2,4-triazol-3-yl)pyridazin-3(2H)-one which falls under the definition of the present invention. However, no field of use or identification data is given for this molecule.

BRIEF DESCRIPTION OF THE INVENTION

An object of the present invention is to provide compounds useful for treating a number of inflammatory processes and various pathologies associated with an elevated level or over-expression of SSAO/VAP-1. The objects of the invention are achieved by claimed pyridazinone and/or pyridone compounds, pharmaceutically acceptable salts, hydrates, or solvates thereof, and by their use as a medicament. The present invention further relates to a pharmaceutical composition comprising one or more of the aforementioned compounds, pharmaceutically acceptable salts, hydrates, or solvates thereof as an active ingredient, and to a process for the preparation of the aforementioned pyridazinones and/or pyridones.

The invention is based on the surprising findings that a specific group of compounds containing a pyridazinone or a pyridone backbone as disclosed in the present invention exhibit SSAO/VAP-1 inhibitory activity and may be used in treatment of vascular damage and inflammatory processes and various pathologies associated with an elevated level or over-expression of SSAO/VAP-1.

The present invention provides pyridazinone and/or pyridone compounds of formula (I) for use as a medicament.

The present invention provides novel pyridazinone and/or pyridone compounds of formula (I')

The present invention also provides pharmaceutical compositions comprising one or more pyridazinone or/and pyridone compound(s) of formula (I).

Additionally, there is provided a process for the preparation of novel pyridazinone and/or pyridone compounds of formula (I').

BRIEF DESCRIPTION OF THE DRAWINGS

In the following the invention will be described in greater detail by means of preferred embodiments with reference to the attached drawings, in which FIG. 1 is a graph showing the effect of compound 43 (grey column) and BTT-2079 (white column) on the daily urinary excretion of methylamine in transgenic mTIEhVAP1 mice.

DETAILED DESCRIPTION OF THE INVENTION

The present invention relates to pyridazinone and/or pyridone compounds having a general formula (I), and pharmaceutically acceptable salts, hydrates, or solvates thereof,

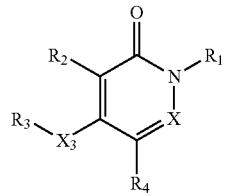

(I)

wherein
X is CH or N;
$R_1$ is phenyl, optionally substituted with $R_{11}$,
wherein $R_{11}$ is selected from the group consisting of halogen, halo-$C_{1-3}$-alkyl, and $C_{1-6}$-alkoxy;
$R_2$ is H or triazolyl;
(i) $X_3$ is O or S, and
$R_3$ is selected from the group consisting of H, $C_{1-6}$-alkyl, $C_{2-6}$-alkenyl, and phenyl, said phenyl being optionally substituted one or more times with $R_{31}$, each $R_{31}$ is independently selected from the group consisting of halogen, halo-$C_{1-3}$-alkyl and $C_{1-6}$-alkoxy; or
(ii) $X_3$ is $NR_3'$, and
$R_3$ and $R_3'$ together with the nitrogen, to which they are attached, form a 5 or 6 membered saturated heterocyclic ring, —$N_3$, or triazole, said triazole being optionally substituted with $R_{32}$, wherein $R_{32}$ is selected from the group consisting of phenyl, $C_{1-6}$-alkyl, and —$CO_2(C_{1-3}$-alkyl); or
$R_3'$ is H or $C_{1-3}$-alkyl, and
$R_3$ is selected from the group consisting of H; $C_{1-6}$-alkyl; $C_{2-6}$-alkenyl; $C_{2-6}$-alkynyl; $C_{3-6}$-cycloalkyl-$C_{1-6}$-alkyl; $C_{1-6}$-cycloalkyl; cyano-$C_{1-6}$-alkyl; amino-$C_{1-6}$-alkyl; benzyl; pyridyl; saturated 5 or 6 membered heterocyclic ring having 1 to 2 heteroatoms selected from N, O, and S, and wherein said N is optionally substituted with $C_{1-6}$-alkyl; $R_{33}R_{33}'N$—$C_{1-6}$-alkylenyl; and phenyl, said phenyl being optionally substituted 1 to 3 times with $R_{34}$;
wherein
$R_{33}$ and $R_{33}'$ are both $C_{1-3}$-alkyl, or $R_{33}$ and $R_{33}'$ together with the nitrogen, to which they are attached, form a saturated 5 or 6 membered heterocyclic ring optionally comprising one further heteroatom selected from N, O, and S;
each $R_{34}$ is independently selected from the group consisting of $NR_{35}R_{35}'$, hydroxy and $C_{1-6}$-alkoxy; or two adjacent $R_{34}$ together with the carbon atoms, to which they are attached, form a 5 or 6 membered fused heterocyclic ring comprising 1 or 2 heteroatom(s) each independently selected from N, O and S;
wherein $R_{35}$ and $R_{35}'$ are both H or $C_{1-6}$-alkyl; or $R_{35}$ and $R_{35}'$ together with the nitrogen, to which they are attached, form a 5 or 6 membered saturated heterocyclic ring optionally further comprising as a ring member O, S, N, or $NR_{36}$, wherein $R_{36}$ is H, $C_{1-6}$-alkyl or benzoyl;
$R_4$ is selected from the group consisting of —CN; —C(=O)$X_4R_{41}$; phenyl, wherein said phenyl is optionally substituted with $R_{42}$; and an 5 or 6 membered unsaturated heterocyclic ring having 1 to 4 heteroatoms each independently selected from N, O and S and being optionally substituted one or more times with $R_{43}$;
wherein
$X_4$ is O, S, or NH; and
$R_{41}$ is selected from the group consisting of H, $C_{1-6}$-alkyl, $R_{44}R_{44}'N$—$O_{1-6}$-alkylenyl, and —$NHR_{45}$,
wherein $R_{44}$ and $R_{44}'$ are both H or $C_{1-6}$-alkyl; or $R_{44}$ and $R_{44}'$ together with the nitrogen, to which they are attached, form a 5 or 6 membered saturated heterocyclic ring; and $R_{45}$ is H or imino-$C_{1-6}$-alkyl; or $X_4$ and $R_{41}$ taken together form —N=$CR_{46}R_{47}$, wherein
$R_{46}$ is H or methyl, and
$R_{47}$ is di($C_{1-3}$-alkyl)amino;

$R_{42}$ is selected from the group consisting of halogen, halo-$C_{1-3}$-alkyl, and $C_{1-6}$-alkoxy;

each $R_{43}$ is independently selected from the group consisting of —OH, —SH, and methyl;

for use as a medicament.

There is further provided according to the present invention novel pyridazinone and/or pyridone compounds of formula (I') and pharmaceutically acceptable salts, hydrates, or solvates thereof,

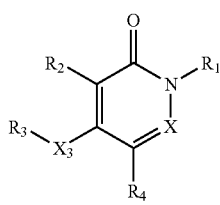

(I')

wherein

X is CH or N;

$R_1$ is phenyl, optionally substituted with $R_{11}$, wherein $R_{11}$ is selected from the group consisting of halogen, halo-$C_{1-3}$-alkyl, and $C_{1-6}$-alkoxy;

$R_2$ is H or triazolyl;

(i) $X_3$ is O or S, and $R_3$ is selected from the group consisting of H, $C_{1-6}$-alkyl, $C_{2-6}$-alkenyl, and phenyl, said phenyl being optionally substituted one or more times with $R_{31}$, each $R_{31}$ is independently selected from the group consisting of halogen, halo-$C_{1-3}$-alkyl and $C_{1-6}$-alkoxy; or (ii) $X_3$ is $NR_3'$, and $R_3$ and $R_3'$ together with the nitrogen, to which they are attached, form a 5 or 6 membered saturated heterocyclic ring, —$N_3$, or triazole, said triazole being optionally substituted with $R_{32}$, wherein $R_{32}$ is selected from the group consisting of phenyl, $C_{1-6}$-alkyl, and —$CO_2$($C_{1-3}$-alkyl); or $R_3'$ is H or $C_{1-3}$-alkyl, and $R_3$ is selected from the group consisting of H; $C_{1-6}$-alkyl; $C_{2-6}$-alkenyl; $C_{2-6}$-alkynyl; $C_{3-6}$-cycloalkyl-$C_{1-6}$-alkyl; $C_{1-6}$-cycloalkyl; cyano-$C_{1-6}$-alkyl; amino-$C_{1-6}$-alkyl; benzyl; pyridyl; saturated 5 or 6 membered heterocyclic ring having 1 to 2 heteroatoms selected from N, O, and S, and wherein said N is optionally substituted with $C_{1-6}$-alkyl; $R_{33}R_{33}'N$—$C_{1-6}$-alkylenyl; and phenyl, said phenyl being optionally substituted 1 to 3 times with $R_{34}$;

wherein $R_{33}$ and $R_{33}'$ are both $C_{1-3}$-alkyl, or $R_{33}$ and $R_{33}'$ together with the nitrogen, to which they are attached, form a saturated 5 or 6 membered heterocyclic ring optionally comprising one further heteroatom selected from N, O, and S;

each $R_{34}$ is independently selected from the group consisting of $NR_{35}R_{35}'$, hydroxy and $C_{1-6}$-alkoxy; or two adjacent $R_{34}$ together with the carbon atoms, to which they are attached, form a 5 or 6 membered fused heterocyclic ring comprising 1 or 2 heteroatom(s) each independently selected from N, O and S;

wherein $R_{35}$ and $R_{35}'$ are both H or $C_{1-6}$-alkyl; or $R_{35}$ and $R_{35}'$ together with the nitrogen, to which they are attached, form a 5 or 6 membered saturated heterocyclic ring optionally further comprising as a ring member O, S, N, or $NR_{36}$, wherein $R_{36}$ is H, $C_{1-6}$-alkyl or benzoyl;

$R_4$ is selected from the group consisting of —ON; —O(=O)$X_4R_{41}$; phenyl, wherein said phenyl is optionally substituted with $R_{42}$; and an 5 or 6 membered unsaturated heterocyclic ring having 1 to 4 heteroatoms each independently selected from N, O and S and being optionally substituted one or more times with $R_{43}$;

wherein $X_4$ is O, S, or NH; and $R_{41}$ is selected from the group consisting of H, $C_{1-6}$-alkyl, $R_{44}R_{44}'N$—$C_{1-6}$-alkylenyl, and —$NHR_{45}$, wherein $R_{44}$ and $R_{44}'$ are both H or $C_{1-6}$-alkyl; or $R_{44}$ and $R_{44}'$ together with the nitrogen, to which they are attached, form a 5 or 6 membered saturated heterocyclic ring; and $R_{45}$ is H or imino-$C_{1-6}$-alkyl; or $X_4$ and $R_{41}$ taken together form —N=$CR_{46}R_{47}$, wherein
$R_{46}$ is H or methyl, and
$R_{47}$ is di($C_{1-3}$-alkyl)amino;

$R_{42}$ is selected from the group consisting of halogen, halo-$C_{1-3}$-alkyl, and $C_{1-6}$-alkoxy;

each $R_{43}$ is independently selected from the group consisting of —OH, —SH, and methyl;

excluding 5-phenoxy-2-phenyl-6-(1H-1,2,4-triazol-3-yl)pyridazin-3(2H)-one.

Preferred compounds of formula (I) or (I') are those wherein X is nitrogen. Another group of preferred compounds of formula (I) or (I') are those wherein X is carbon.

Further preferred compounds of Formula (I) or (I') are those wherein $R_2$ is hydrogen. Also preferred compounds of Formula (I) or (I') are those where the $R_1$ phenyl is unsubstituted or substituted one or two times with $R_{11}$ selected from the group consisting of methoxy, trifluoromethyl, and halogen, said halogen being preferably o-F, m-F, p-Cl or m-Cl.

Preferred compounds of Formula (I) or (I') also include compounds of formula (I) wherein $X_3$ is O; further preferred are those where $X_3$ and $R_3$ form together a group selected from the group consisting of $C_{1-6}$-alkyloxy, such as methoxy or ethoxy; and optionally substituted phenoxy. Preferred $R_{31}$ include p-methoxy and p-Cl.

Preferred compounds of formula (I) or (I') also include those where $X_3$ is $NR_3'$; further preferred are those where $X_3$ and $R_3$ form together a group selected from the group consisting of N-methyl piperazinyl, pyrrolidinyl, optionally substituted 1,2,3-triazolyl, and —$NR_3R_3'$. Advantageously the said 1,2,3-triazolyl is substituted with $R_{32}$, which selected from the group consisting of phenyl, propyl, and —$CO_2$Me.

Further preferred compounds of formula (I) or (I') are those where $X_3$ is NH and $R_3$ is selected from the group consisting of H; $C_{1-6}$-alkyl, such as methyl, ethyl, or isopropyl; $C_{3-9}$-cycloalkyl, such as cyclohexyl; optionally substituted phenyl; benzyl; $R_{33}R_{33}'N$—$C_{1-6}$-alkylenyl, such as pyrrolidinyl ethylenyl or morpholinyl ethylenyl; and saturated heterocycle, such as pyrrolidine or N-methyl piperidine; phenyl substituted with $R_{34}$ preferably each $R_{34}$ being independently selected from the group consisting of dimethylamino, methoxy and saturated six membered heterocycles, such as piperidinyl, N-methyl or N-benzoyl piperazinyl, or morpholinyl. Further preferred compounds of formula (I) or (I') are those where when $X_3$ is $NR_3'$, the $R_3$ phenyl group is mono-substituted at the para-position with $R_{34}$, 1, 2 or 3 times with methoxy or two adjacent $R_{34}$ substituents form together an —O—$C_{1-3}$-alkylenyl-O-brige.

Another group of preferred compounds of formula (I) or (I') are those wherein $R_4$ is selected from the group consisting of 1,2,3-triazolyl and 1,2,4-triazolyl. Preferably the point of attachment of the triazolyl group is at a carbon atom of the triazolyl ring.

Further preferred compounds of formula (I) or (I') are those wherein X, $R_1$, $R_2$, $X_3$, $R_3$ and $R_4$ are each independently one to be found in any one of the examples or in an appropriate table.

Especially preferred compounds of formula (I) or (I') are those of formula (I-a)-(I-d)

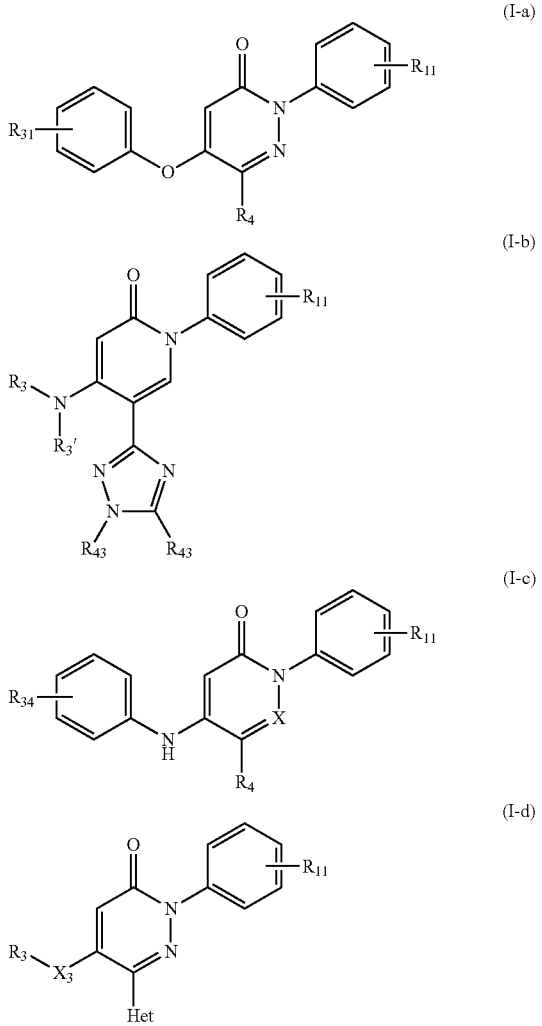

wherein $X_3$, $R_3$, $R_3'$, $R_4$, $R_{11}$, $R_{31}$, $R_{34}$, and $R_{43}$ are each independently as defined above or $R_{11}$, $R_{34}$, or/and $R_{43}$ is alternatively H, and Het is an 5 or 6 membered heterocyclic ring having 1 to 4 heteroatoms each independently selected from N, O and S, preferably having 2 to 3 N heteroatoms, and being optionally substituted one or more times with $R_{43}$.

Specific examples of preferred compounds of formula (I) or (I') are 2-(4-chlorophenyl)-5-phenoxy-6-(1H-1,2,4-triazol-3-yl)-3 (2H)-pyridazinone;

5-isopropylamino-2-phenyl-6-(1H-1,2,4-triazol-3-yl)-3 (2H)-pyridazinone;

5-cyclohexylamino-2-phenyl-6-(1H-1,2,4-triazol-3-yl)-3 (2H)-pyridazinone;

4-isopropylamino-1-phenyl-5-(1H-1,2,4-triazol-3-yl)-pyridin-2(1H)-one;

2-(4-chlorophenyl)-5-[(4-methoxyphenyl)amino]-6-(1H-1, 2,4-triazol-3-yl)-3(2H)-pyridazinone;

2-(4-chlorophenyl)-5-[(3,4-methylenedioxyphenyl)amino]-6-(1H-1,2,4-triazol-3-yl)-3(2H)-pyridazinone;

2-(4-chlorophenyl)-5-{[4-(4-methylpiperazine-1-yl)phenyl]amino}-6-(1H-1,2,4-triazol-3-yl)-3(2H)-pyridazinone;

2-(4-chlorophenyl)-5-{[4-(N,N-dimethylamino)phenyl]amino}-6-(1H-1,2,4-triazol-3-yl)-3(2H)-pyridazinone;

2-(4-chlorophenyl)-5-[(N-methylpiperidin-4-yl)amino]-6-(1H-1,2,4-triazol-3-yl)-3(2H)-pyridazinone;

2-(4-chlorophenyl)-5-{[4-(4-piperazine-1-yl)phenyl]amino}-6-(1H-1,2,4-triazol-3-yl)-3(2H)-pyridazinone;

1-(4-chlorophenyl)-4-{[4-(4-methylpiperazin-1-yl)phenyl]amino}-5-(1H-1,2,4-triazol-3-yl)-pyridin-2(1H)-one;

and pharmaceutically acceptable salts, hydrates, and solvates thereof.

The term "halogen" as used herein and hereafter by itself or as part of other groups refers to the Group VIIa elements and includes Cl, Br, F or I groups. Preferred halogen substituents are Cl and F.

The term "$C_{1-6}$-alkyl or $C_{1-3}$-alkyl" as used herein and hereafter as such or as part of haloalkyl, alkoxy or cycloalkyl group is an aliphatic linear or branched hydrocarbon group having suitably 1 to 6 or 1 to 3, respectively, carbon atoms, preferably 1 to 3, in the alkyl moiety and thus $C_{1-3}$-alkyl includes methyl, ethyl, n-propyl, isopropyl, and $C_{1-6}$-alkyl additionally includes n-butyl, sec-butyl, isobutyl, tert-butyl, and branched and straight chain pentyl and hexyl.

The term "alkylenyl" as used herein and hereafter, is a divalent group derived from a straight or branched chain hydrocarbon of having suitably 1 to 6 carbon atoms. Representative examples of alkylenyl include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, and —$CH_2CH(CH_3)CH_2$—.

The term "$C_{2-6}$-alkenyl" as used herein and hereafter is an unsaturated linear or branched hydrocarbon group having at least one olefinic double bond between any two carbon atoms, such as ethenyl, propenyl, butenyl, pentenyl, and hexenyl. Examples of preferred alkenyls groups include, but are not limited to, linear alkenyl groups having a terminal double bond such as vinyl and allyl groups.

The term "$C_{2-6}$-alkynyl" as used herein is an unsaturated linear or branched hydrocarbon group having at least one olefinic triple bond between any two carbon atoms, such as ethynyl, propynyl, butynyl, pentynyl, and hexynyl. Examples of preferred alkynyl groups include, but are not limited to, linear alkynyls groups having a terminal triple bond.

The term "$C_{3-9}$-cycloalkyl" as used herein and hereafter refers to cycloalkyl groups having 3 to 9 carbon atoms and thus includes cyclopropyl, cyclobutyl, cyclopentyl, cyclohexyl, cycloheptyl, cyclooctyl and cyclononyl.

The term "haloalkyl" as used herein and hereafter refers to any of the above alkyl groups substituted with one or more halogen, preferably F or Cl. Examples of haloalkyl groups include, but are not limited to, chloromethyl, fluoromethyl, trifluoromethyl and trichloromethyl. Preferred haloalkyl is trifluoromethyl (—$CF_3$).

The term "$C_{1-6}$-alkoxy" as used herein and hereafter refers to a —O—($C_{1-6}$-alkyl) group where the "$C_{1-6}$-alkyl" has the above-defined meaning. Examples of preferred alkoxy groups include, but are not limited to, methoxy, ethoxy, and iso-propyloxy.

The term "triazole" or "triazolyl" as used herein and hereafter refers to either one of a pair of isomeric compounds having unsaturated five-membered ring of two carbon atoms and three nitrogen atoms i.e. 1,2,3-triazole and 1,2,4-triazole and any tautomers thereof, e.g. 1H-1,2,4-triazole and 4H-1, 2,4-triazole. The triazole group may be attached at any nitrogen or carbon atom resulting in the creation of a stable structure and may be additionally further substituted at any carbon atom or nitrogen heteroatom suitable for substitution.

The term "optionally substituted" as used herein and hereafter in context of a phenyl group denotes phenyl that is either unsubstituted or substituted independently with one or more, preferably 1, 2, or 3, substituent(s) attached at any available atom to produce a stable compound, e.g. phenyl may be substituted once with a denoted substituent attached to o-, p- or m-position of the phenyl ring. In general "substituted" refers to a substituent group as defined herein in which one or more bonds to a hydrogen atom contained therein are replaced by a bond to a non-hydrogen atom unless otherwise denoted.

The term "cyano-$C_{1-6}$-alkyl" as used herein and hereafter refers to refers to $C_{1-6}$-alkyl groups containing a cyano group (—CN) where the "alkyl" has the above-defined meaning. The cyano group may be attached at any carbon atom of the alkyl chain which results in the creation of a stable structure, preferably the terminal carbon of the alkyl chain.

The term "amino-$C_{1-6}$-alkyl" as used herein and hereafter refers to $C_{1-6}$-alkyl groups containing a primary amine group (—$NH_2$) where the "alkyl" has the above-defined meaning. The amine group may be attached at any carbon atom of the alkyl chain which results in the creation of a stable structure, preferably the terminal carbon of the alkyl chain. Examples of useful alkylamine groups include, but are not limited to, aminomethyl, 2-amino-n-ethyl, and 3-amino-n-propyl.

The term "pyridyl" as used herein and hereafter refers to six membered unsaturated heterocyclic ring containing one nitrogen atom know as pyridine. The pyridyl ring may be attached via any carbon atom. Preferably the pyridyl group is attached via C3 or C4.

The term "5 or 6 membered heterocyclic ring" as used herein and hereafter represents a stable 5 to 6 membered monocyclic ring which may be saturated or unsaturated, unless otherwise denoted, and which consists of carbon atoms and from 1 to 4, preferably 1 to 2 in the case of saturated heterocyclic rings, heteroatom(s) each independently selected from the group consisting of N, O, and S, wherein N when applicable represents NH or may be otherwise further substituted. The heterocyclic ring may be attached via any heteroatom or carbon atom resulting in the creation of a stable structure unless otherwise denoted. The heterocyclic ring may be further substituted at any carbon atom or nitrogen heteroatom suitable for substitution, wherein the substituent is preferably hydroxyl, thiol, benzyloxy, or an afore-defined alkyl, more preferably methyl.

Examples of unsaturated heterocyclic rings include pyrrolyl, furanyl, and thiophenyl (thienyl), imidazolyl, imidazonlinyl, pyrazolyl, dihydropyrazolyl, oxazolyl, isoxazolyl, dioxolanyl thiazolyl, and isothiazolyl, triazolyl as defined above, tetrazolyl, and pyridinyl, and regioisomers, tautomers and optionally substituted derivates thereof. Examples of preferred saturated heterocyclic rings include, but are not limited to, pyrrolidinyl, piperidinyl, N-methyl piperidinyl, piperazinyl, N-methyl piperazinyl, and morpholinyl.

The term "di($C_{1-6}$-alkyl)amino" used herein and hereafter refers to a tertiary amine group, wherein the nitrogen atom is connected to two $C_{1-6}$-alkyl groups where the "$C_{1-6}$-alkyl" has the above-defined meaning and which two alkyl groups may optionally be fused together to form together with the nitrogen atom they are attached to a 5 to 6 membered saturated heterocyclic ring which has the above-defined meaning.

The term "imino-$C_{1-6}$-alkyl" used herein and hereafter refers to $C_{1-6}$-alkyl groups containing a primary aldimine group where the "$C_{1-6}$-alkyl" has the above defined meaning. The said aldimine group can be attached to any carbon atom of the said alkyl chain, preferably the terminal carbon.

When compounds described herein contain olefinic double bonds or other centres of geometric asymmetry, and unless specified otherwise, it is intended to include both E and Z geometric isomers. Further some of the compounds disclosed herein may contain one or more asymmetric centres and may thus give rise to enantiomers, diastereomers, other steroisomeric forms, and crystalline and non-crystalline forms. The present invention is also meant to encompass racemic and/or steroisomeric mixtures, resolved forms, and mixtures thereof in all proportions, as well as the individual enantiomers and/or diastereomers that may be separated according to methods that are known to those skilled in the art. The present invention is further meant to include any eventual metabolite, prodrug, and tautomeric forms of the compounds of the present invention.

When any variable occurs more than one time in any constituent or in Formula (I) or (I'), its definition on each occurrence is independent of its definition at every other occurrence. Further, combinations of substituents and/or variables are permissible only if such combination results a stable compound.

"Optional" or "optionally" denotes that the subsequently described event or circumstance may but need not occur, and that the description includes instances where the event or circumstance occurs and instances in which it does not. "Comprises" or "comprising" denotes that the subsequently described set may but need not include other elements.

The compounds of this invention are also useful in the form of acid addition salts, hydrates, or solvates thereof. Preferred are compounds of formula (I) or (I') as defined herein and pharmaceutically acceptable salts thereof. The expression "pharmaceutically acceptable" represents being useful in the preparation a pharmaceutical composition that is generally safe, non-toxic, and neither biologically nor otherwise undesirable, and includes being useful for both veterinary use as well as human pharmaceutical use.

The expression "acid addition salt" includes any non-toxic organic and inorganic acid addition salts that the compounds (I) or (I') can form. Illustrative inorganic acids, which form suitable salts, include, but are not limited to, hydrogen chloride, hydrogen bromide, sulphuric and phosphoric acids. Illustrative organic acids, which form suitable salts, include, but are not limited to, acetic acid, lactic acid, malonic acid, succinic acid, glutaric acid, fumaric acid, malic acid, tartaric acid, citric acid, ascorbic acid, maleic acid, benzoic acid, phenylacetic acid, cinnamic acid, methane sulfonic acid, salicylic acid, and the like. The term "acid addition salt" as used herein also comprises solvates which the compounds and salts thereof are able to form, such as, for example, hydrates, alcoholates, and the like. These salts also include salts useful for the chiral resolution of racemates.

Illustrative, but not limiting, examples of compounds (I) and (I') of the present invention are those presented in the following Table 1.

TABLE 1

| Number | Structure | Formula. | m.p. (° C.) |
| --- | --- | --- | --- |
| 1 | (6-oxo-1-phenyl-4-phenoxy-3-(1-methyl-1H-pyrazol-5-yl)pyridazine) | C₂₀H₁₆N₄O₂ | 118-119 |
| 3 | (6-oxo-1-phenyl-4-hydroxy-3-(1H-1,2,4-triazol-3-yl)pyridazine) | C₁₂H₉N₅O₂ | 218-220 |
| 4 | (6-oxo-1-phenyl-4-phenoxy-pyridazine-3-carboxamide with N-(2-(dimethylamino)ethyl)) · HCl | C₂₁H₂₃ClN₄O₃ | 138-141 |
| 5 | (6-oxo-1-phenyl-4-phenoxy-pyridazine-3-carboxamide with N-(2-(pyrrolidin-1-yl)ethyl)) · HCl | C₂₃H₂₅ClN₄O₃ | 175-178 |
| 6 | (methyl 6-oxo-1-phenyl-4-(4-phenyl-1H-1,2,3-triazol-1-yl)pyridazine-3-carboxylate) | C₂₀H₁₅N₅O₃ | 240-248 |
| 7 | (methyl 4-(4-(ethoxycarbonyl)-1H-1,2,3-triazol-1-yl)-6-oxo-1-phenyl-pyridazine-3-carboxylate) | C₁₇H₁₅N₅O₅ | 165-170 |

TABLE 1-continued

| Number | Structure | Formula. | m.p. (° C.) |
|---|---|---|---|
| 8 | 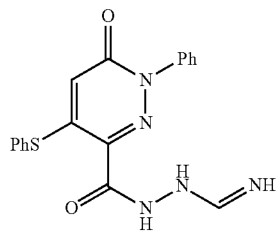 | $C_{18}H_{15}N_5O_2S$ | 236-238 |
| 9 | 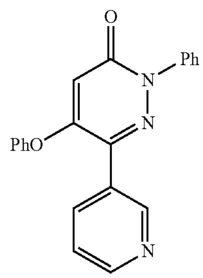 [SMILES: O=c1cc(Oc2ccccc2)c(-c2cccnc2)nn1-c1ccccc1] | $C_{21}H_{15}N_3O_2$ | 155-157 |
| 10 | 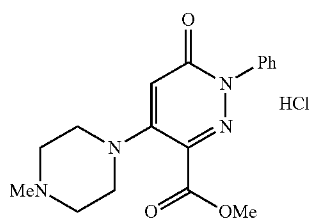 [SMILES: COC(=O)c1nn(-c2ccccc2)c(=O)cc1N1CCN(C)CC1 ; Cl] | $C_{17}H_{21}ClN_4O_3$ | 138-142 |
| 11 | 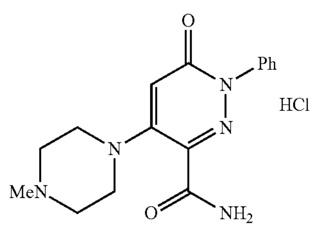 [SMILES: CN1CCN(c2cc(=O)n(-c3ccccc3)nc2C(N)=O)CC1 ; Cl] | $C_{16}H_{19}N_5O_2$ | 248-250 |
| 12 | 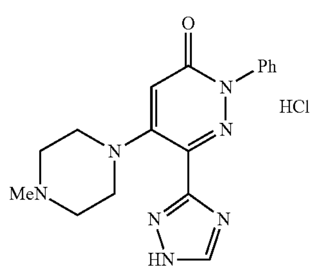 [SMILES: CN1CCN(c2cc(=O)n(-c3ccccc3)nc2-c2nc[nH]n2)CC1 ; Cl] | $C_{17}H_{20}ClN_7O$ | 215-218 |
| 13 | 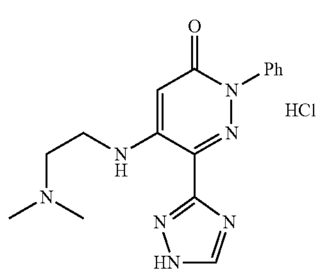 [SMILES: CN(C)CCNc1cc(=O)n(-c2ccccc2)nc1-c1nc[nH]n1 ; Cl] | $C_{16}H_{20}ClN_7O$ | 211-214 |

TABLE 1-continued

| Number | Structure | Formula | m.p. (° C.) |
|---|---|---|---|
| 14 | 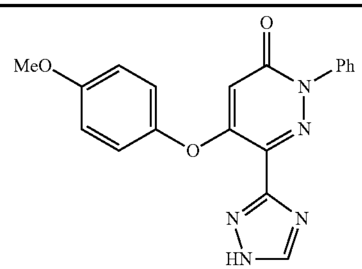 | $C_{19}H_{15}N_5O_3$ | 253-257 |
| 15 | 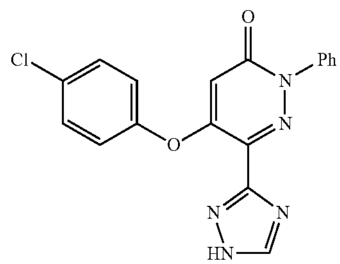 [SMILES: O=c1cc(Oc2ccc(Cl)cc2)c(-c2nc[nH]n2)nn1-c1ccccc1] | $C_{18}H_{12}ClN_5O_2$ | 235-240 |
| 16 | 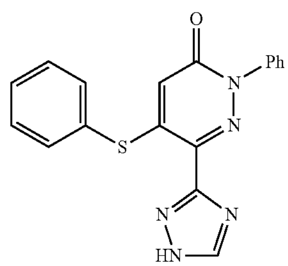 [SMILES: O=c1cc(Sc2ccccc2)c(-c2nc[nH]n2)nn1-c1ccccc1] | $C_{18}H_{13}N_5OS$ | 245-250 |
| 17 | 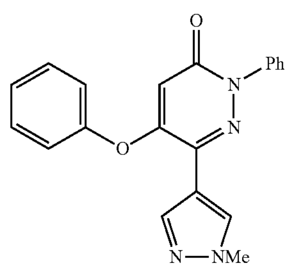 [SMILES: Cn1cc(-c2nn(-c3ccccc3)c(=O)cc2Oc2ccccc2)cn1] | $C_{20}H_{16}N_4O_2$ | 195-197 |
| 18 | 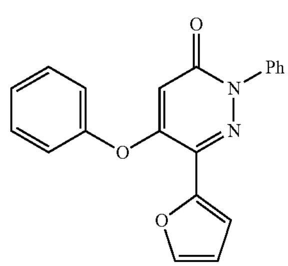 [SMILES: O=c1cc(Oc2ccccc2)c(-c2ccco2)nn1-c1ccccc1] | $C_{20}H_{14}N_2O_3$ | 232-234 |
| 19 | 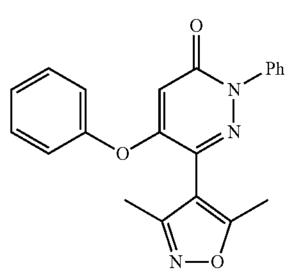 [SMILES: Cc1noc(C)c1-c1nn(-c2ccccc2)c(=O)cc1Oc1ccccc1] | $C_{21}H_{17}N_3O_3$ | 122-124 |

TABLE 1-continued

| Number | Structure | Formula. | m.p. (° C.) |
| --- | --- | --- | --- |
| 20 | 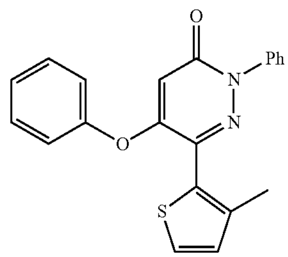 [SMILES: Cc1ccsc1-c1nn(-c2ccccc2)c(=O)cc1Oc1ccccc1] | $C_{21}H_{16}N_2O_2S$ | 212-214 |
| 21 | 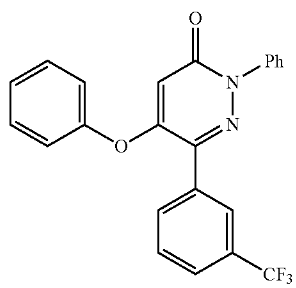 [SMILES: O=c1cc(Oc2ccccc2)c(-c2cccc(C(F)(F)F)c2)nn1-c1ccccc1] | $C_{23}H_{15}F_3N_2O_2$ | 146-148 |
| 22 | 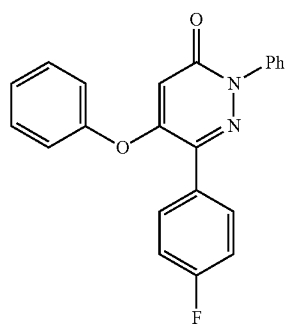 [SMILES: O=c1cc(Oc2ccccc2)c(-c2ccc(F)cc2)nn1-c1ccccc1] | $C_{22}H_{15}FN_2O_2$ | 146-148 |
| 23 | 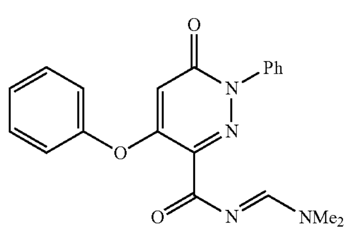 [SMILES: CN(C)/C=N/C(=O)c1nn(-c2ccccc2)c(=O)cc1Oc1ccccc1] | $C_{20}H_{18}N_4O_3$ | 175-176 |
| 24 | 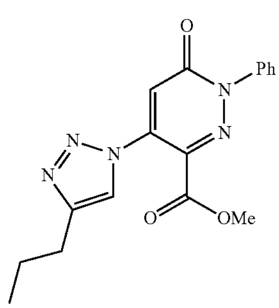 [SMILES: CCCc1cn(-c2cc(=O)n(-c3ccccc3)nc2C(=O)OC)nn1] | $C_{17}H_{17}N_5O_3$ | 146-148 |

TABLE 1-continued

| Number | Structure | Formula | m.p. (° C.) |
| --- | --- | --- | --- |
| 25 | 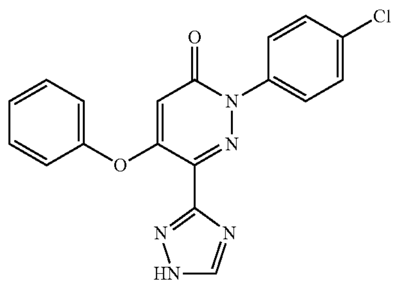 [SMILES: O=c1cc(Oc2ccccc2)c(-c2nc[nH]n2)nn1-c1ccc(Cl)cc1] | $C_{18}H_{12}ClN_5O_2$ | 246-247 |
| 26 | 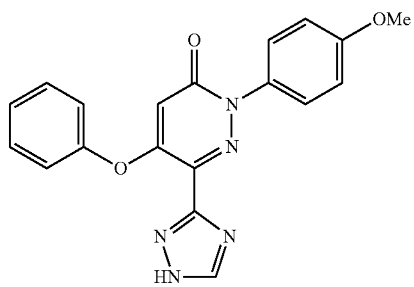 [SMILES: COc1ccc(-n2nc(-c3nc[nH]n3)c(Oc3ccccc3)cc2=O)cc1] | $C_{19}H_{15}N_5O_3$ | 284-286 |
| 27 | 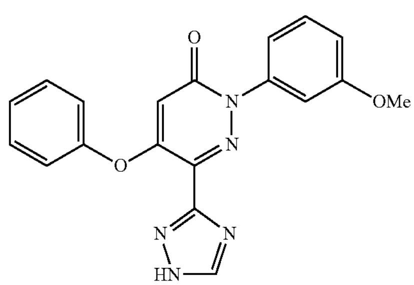 [SMILES: COc1cccc(-n2nc(-c3nc[nH]n3)c(Oc3ccccc3)cc2=O)c1] | $C_{19}H_{15}N_5O_3$ | 253-254 |
| 28 | 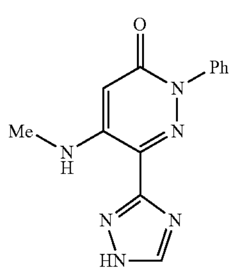 [SMILES: CNc1cc(=O)n(-c2ccccc2)nc1-c1nc[nH]n1] | $C_{13}H_{12}N_6O$ | 245-247 |
| 29 | 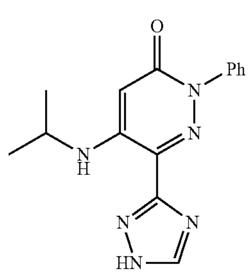 [SMILES: CC(C)Nc1cc(=O)n(-c2ccccc2)nc1-c1nc[nH]n1] | $C_{15}H_{16}N_6O$ | 203-205 |

TABLE 1-continued

| Number | Structure | Formula. | m.p. (° C.) |
|---|---|---|---|
| 30 | 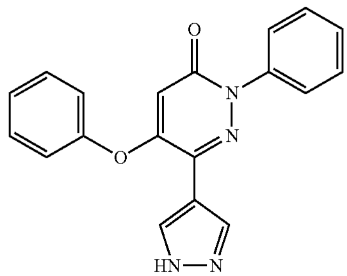 [SMILES: O=c1cc(Oc2ccccc2)c(-c2cn[nH]c2)nn1-c1ccccc1] | $C_{19}H_{14}N_4O_2$ | 245-247 |
| 31 | 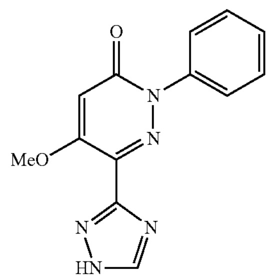 [SMILES: COc1cc(=O)n(-c2ccccc2)nc1-c1nc[nH]n1] | $C_{13}H_{11}N_5O_2$ | 235-240 |
| 32 | 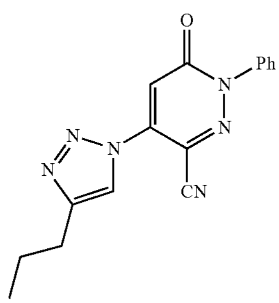 [SMILES: CCCc1cn(-c2cc(=O)n(-c3ccccc3)nc2C#N)nn1] | $C_{16}H_{14}N_6O$ | 192-195 |
| 33 | 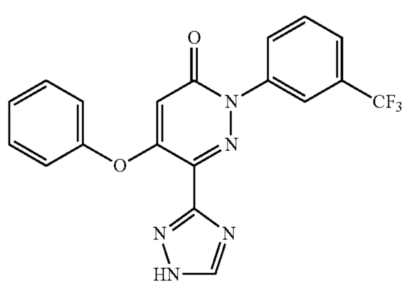 [SMILES: O=c1cc(Oc2ccccc2)c(-c2nc[nH]n2)nn1-c1cccc(C(F)(F)F)c1] | $C_{19}H_{12}F_3N_5O_2$ | 257-258 |
| 34 | 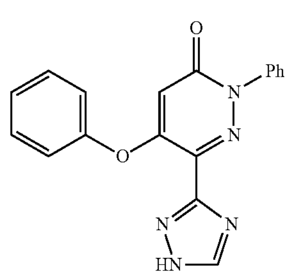 | $C_{19}H_{14}N_4O_2$ | 275-276 |

TABLE 1-continued

| Number | Structure | Formula | m.p. (° C.) |
| --- | --- | --- | --- |
| 35 | 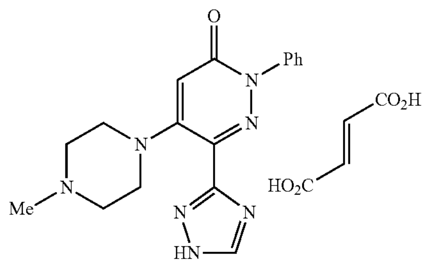 [SMILES: CN1CCN(c2cc(=O)n(-c3ccccc3)nc2-c2nc[nH]n2)CC1 ; O=C(O)/C=C/C(=O)O] | $C_{22}H_{24}N_6O_5$ | 236-239 |
| 36 | 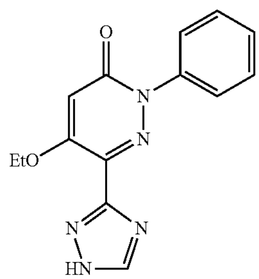 [SMILES: CCOc1cc(=O)n(-c2ccccc2)nc1-c1nc[nH]n1] | $C_{14}H_{13}N_5O_2$ | 195-197 |
| 37 | 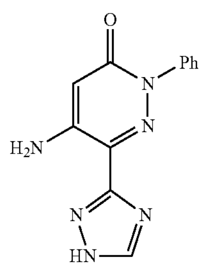 [SMILES: Nc1cc(=O)n(-c2ccccc2)nc1-c1nc[nH]n1] | $C_{13}H_{11}N_5O$ | 245-247 |
| 38 | 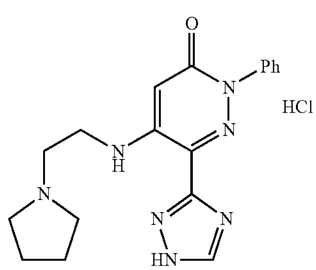 [SMILES: O=c1cc(NCCN2CCCC2)c(-c2nc[nH]n2)nn1-c1ccccc1 ; Cl] | $C_{18}H_{22}ClN_7O$ | 281-284 |
| 39 | 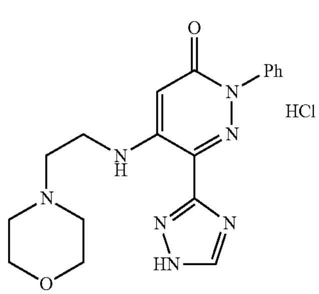 [SMILES: O=c1cc(NCCN2CCOCC2)c(-c2nc[nH]n2)nn1-c1ccccc1 ; Cl] | $C_{18}H_{22}ClN_7O_2$ | 251-258 |

TABLE 1-continued

| Number | Structure | Formula. | m.p. (° C.) |
|---|---|---|---|
| 40 | 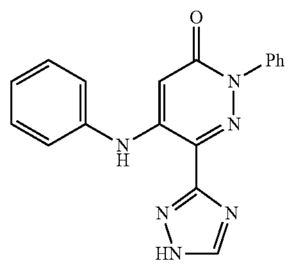 [SMILES: O=c1cc(Nc2ccccc2)c(-c2nc[nH]n2)nn1-c1ccccc1] | $C_{18}H_{14}N_6O$ | 287-290 |
| 41 | 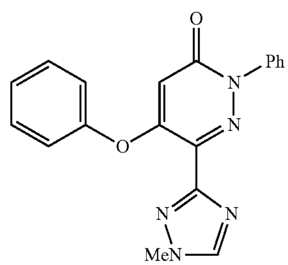 [SMILES: Cn1cnc(-c2nn(-c3ccccc3)c(=O)cc2Oc2ccccc2)n1] | $C_{19}H_{15}N_5O_2$ | 235-237 |
| 42 | 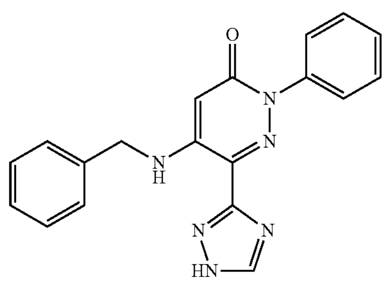 [SMILES: O=c1cc(NCc2ccccc2)c(-c2nc[nH]n2)nn1-c1ccccc1] | $C_{19}H_{16}N_6O$ | 192-193 |
| 43 | 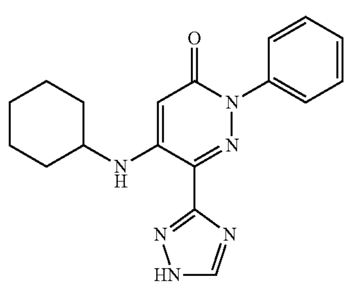 [SMILES: O=c1cc(NC2CCCCC2)c(-c2nc[nH]n2)nn1-c1ccccc1] | $C_{18}H_{20}N_6O$ | 225-227 |
| 44 | 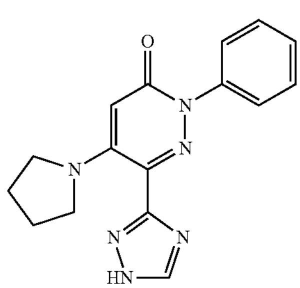 [SMILES: O=c1cc(N2CCCC2)c(-c2nc[nH]n2)nn1-c1ccccc1] | $C_{16}H_{16}N_6O$ | 301-303 |

TABLE 1-continued

| Number | Structure | Formula. | m.p. (° C.) |
|---|---|---|---|
| 45 | 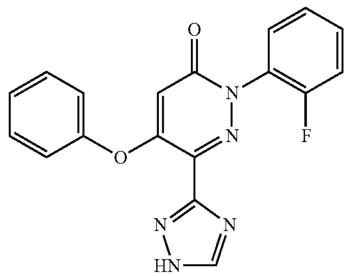 [SMILES: O=c1cc(Oc2ccccc2)c(-c2nc[nH]n2)nn1-c1ccccc1F] | $C_{18}H_{12}FN_5O_2$ | 265-267 |
| 46 | 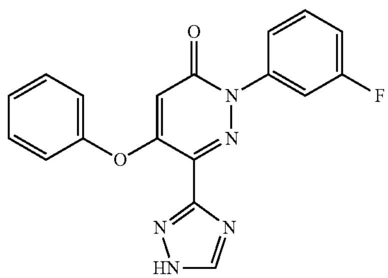 [SMILES: O=c1cc(Oc2ccccc2)c(-c2nc[nH]n2)nn1-c1cccc(F)c1] | $C_{18}H_{12}FN_5O_2$ | 262-264 |
| 47 | 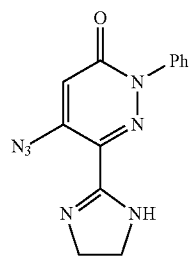 [SMILES: [N-]=[N+]=Nc1cc(=O)n(-c2ccccc2)nc1C1=NCCN1] | $C_{13}H_{11}N_7O$ | 238-240 |
| 51 | 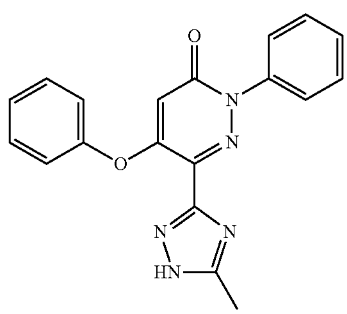 [SMILES: Cc1nc(-c2nn(-c3ccccc3)c(=O)cc2Oc2ccccc2)n[nH]1] | $C_{19}H_{15}N_5O_2$ | 245-247 |
| 52 | 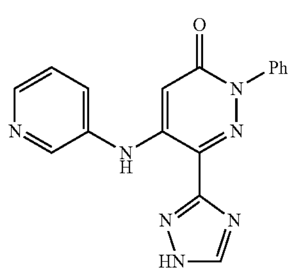 [SMILES: O=c1cc(Nc2cccnc2)c(-c2nc[nH]n2)nn1-c1ccccc1] | $C_{17}H_{13}N_7O$ | 172-174 |

TABLE 1-continued

| Number | Structure | Formula. | m.p. (° C.) |
|---|---|---|---|
| 53 | 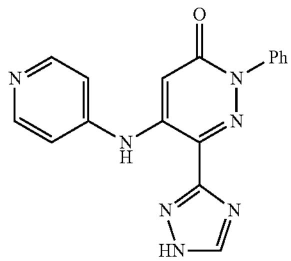 [SMILES: O=c1cc(Nc2ccncc2)c(-c2nc[nH]n2)nn1-c1ccccc1] | C₁₇H₁₃N₇O | 342-344 |
| 54 | 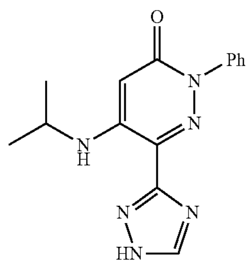 [SMILES: CC(C)Nc1cc(=O)n(-c2ccccc2)nc1-c1nc[nH]n1] | C₁₆H₁₇N₅O | 307-310 |
| 56 | 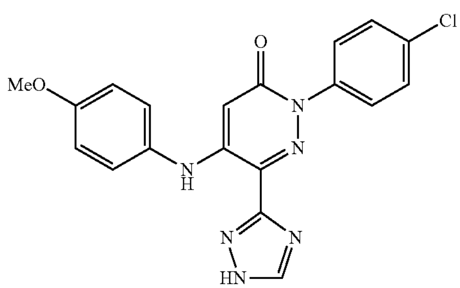 [SMILES: COc1ccc(Nc2cc(=O)n(-c3ccc(Cl)cc3)nc2-c2nc[nH]n2)cc1] | C₂₀H₁₆ClN₅O₂ | 305-307 |
| 57 | 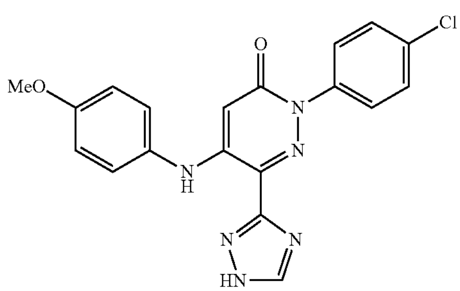 [SMILES: COc1ccc(Nc2cc(=O)n(-c3ccc(Cl)cc3)nc2-c2nc[nH]n2)cc1] | C₁₉H₁₅ClN₆O₂ | 251-252 |
| 58 | 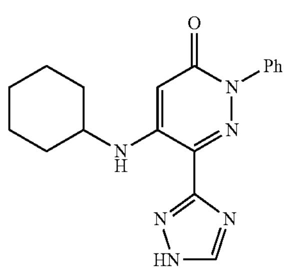 [SMILES: O=c1cc(NC2CCCCC2)c(-c2nc[nH]n2)nn1-c1ccccc1] | C₁₉H₂₁N₅O | 269-270 |

TABLE 1-continued

| Number | Structure | Formula. | m.p. (° C.) |
|---|---|---|---|
| 59 | 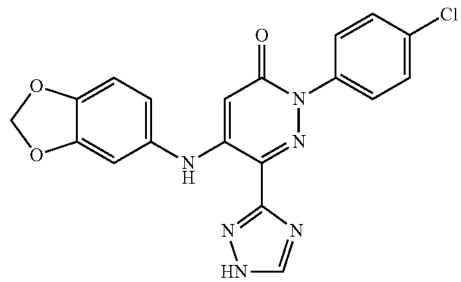 [SMILES: O=c1cc(Nc2ccc3c(c2)OCO3)c(-c2nc[nH]n2)nn1-c1ccc(Cl)cc1] | $C_{19}H_{13}ClN_6O_3$ | 270-273 |
| 60 | 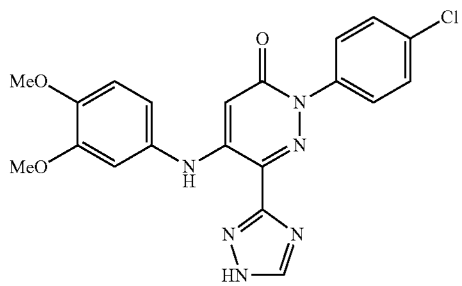 [SMILES: COc1ccc(Nc2cc(=O)n(-c3ccc(Cl)cc3)nc2-c2nc[nH]n2)cc1OC] | $C_{20}H_{17}ClN_6O_3$ | 227-230 |
| 61 | 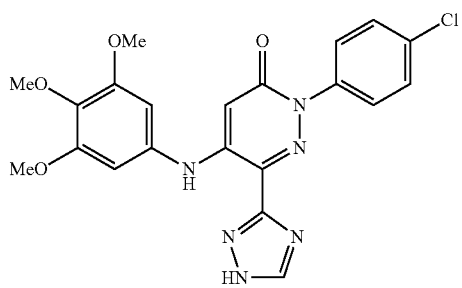 [SMILES: COc1cc(Nc2cc(=O)n(-c3ccc(Cl)cc3)nc2-c2nc[nH]n2)cc(OC)c1OC] | $C_{21}H_{19}ClN_6O_4$ | 238-241 |
| 62 | 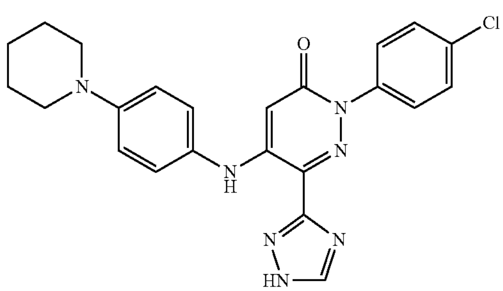 [SMILES: O=c1cc(Nc2ccc(N3CCCCC3)cc2)c(-c2nc[nH]n2)nn1-c1ccc(Cl)cc1] | $C_{23}H_{22}ClN_7O$ | 240-242 |
| 63 | 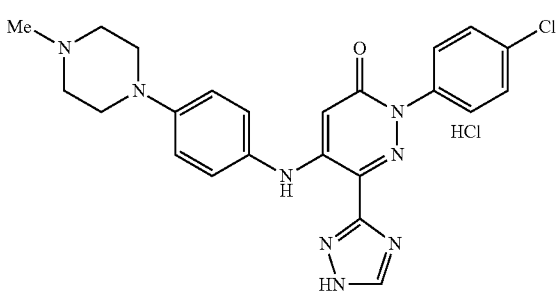 [SMILES: CN1CCN(c2ccc(Nc3cc(=O)n(-c4ccc(Cl)cc4)nc3-c3nc[nH]n3)cc2)CC1 ; Cl] | $C_{23}H_{24}Cl_2N_8O$ | 227-229 |

TABLE 1-continued

| Number | Structure | Formula | m.p. (° C.) |
|---|---|---|---|
| 64 | 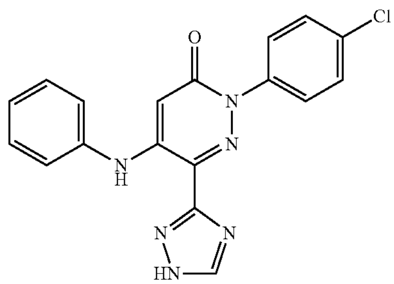 [SMILES: O=c1cc(Nc2ccccc2)c(-c2nc[nH]n2)nn1-c1ccc(Cl)cc1] | $C_{18}H_{13}ClN_6O$ | 244-246 |
| 65 | 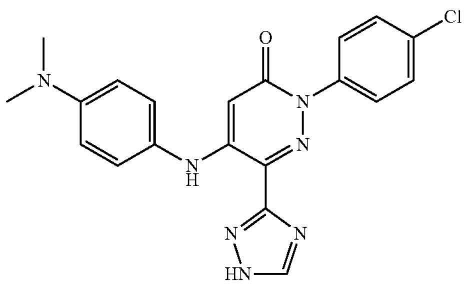 [SMILES: CN(C)c1ccc(Nc2cc(=O)n(-c3ccc(Cl)cc3)nc2-c2nc[nH]n2)cc1] | $C_{20}H_{18}ClN_7O$ | 276-279 |
| 66 | 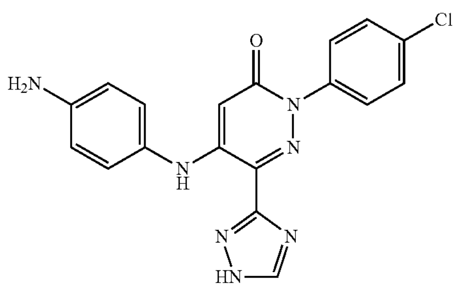 [SMILES: Nc1ccc(Nc2cc(=O)n(-c3ccc(Cl)cc3)nc2-c2nc[nH]n2)cc1] | $C_{18}H_{14}ClN_7O$ | 278-281 |
| 67 | 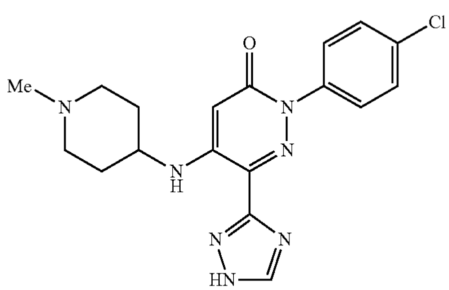 [SMILES: CN1CCC(Nc2cc(=O)n(-c3ccc(Cl)cc3)nc2-c2nc[nH]n2)CC1] | $C_{18}H_{20}ClN_7O$ | 270-272 |
| 68 | 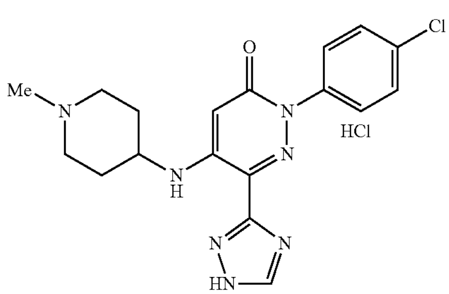 [SMILES: CN1CCC(Nc2cc(=O)n(-c3ccc(Cl)cc3)nc2-c2nc[nH]n2)CC1 ; Cl] | $C_{18}H_{21}Cl_2N_7O$ | 227-230 |

TABLE 1-continued

| Number | Structure | Formula. | m.p. (° C.) |
|---|---|---|---|
| 69 | 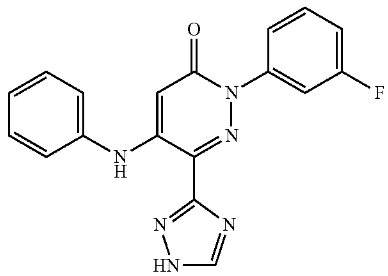 [SMILES: O=c1cc(Nc2ccccc2)c(-c2nc[nH]n2)nn1-c1cccc(F)c1] | $C_{18}H_{13}FN_6O$ | 233-235 |
| 70 | 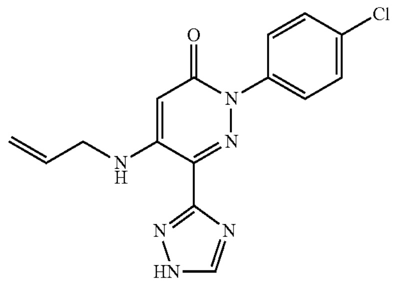 [SMILES: C=CCNc1cc(=O)n(-c2ccc(Cl)cc2)nc1-c1nc[nH]n1] | $C_{15}H_{13}ClN_6O$ | 212-215 |
| 71 | 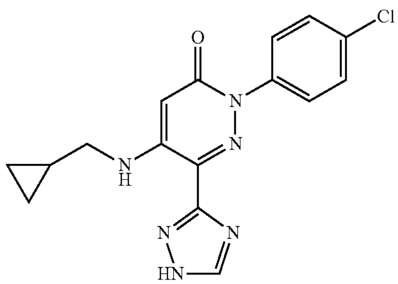 [SMILES: O=c1cc(NCC2CC2)c(-c2nc[nH]n2)nn1-c1ccc(Cl)cc1] | $C_{16}H_{15}ClN_6O$ | 255-257 |
| 72 | 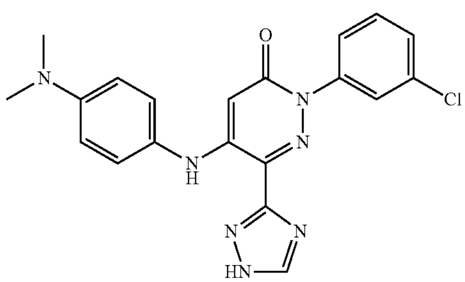 [SMILES: CN(C)c1ccc(Nc2cc(=O)n(-c3cccc(Cl)c3)nc2-c2nc[nH]n2)cc1] | $C_{20}H_{18}ClN_7O$ | 243-245 |
| 73 | 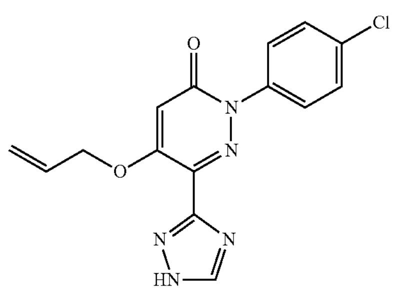 [SMILES: C=CCOc1cc(=O)n(-c2ccc(Cl)cc2)nc1-c1nc[nH]n1] | $C_{15}H_{12}ClN_5O_2$ | 172-175 |

TABLE 1-continued

| Number | Structure | Formula. | m.p. (° C.) |
|---|---|---|---|
| 74 | 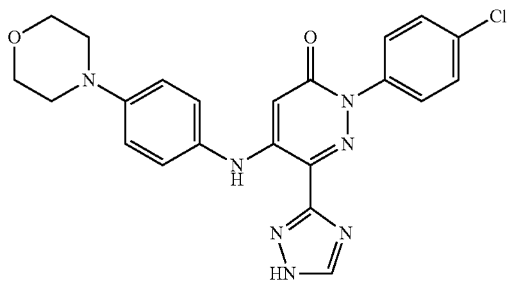 [SMILES: O=c1cc(Nc2ccc(N3CCOCC3)cc2)c(-c2nc[nH]n2)nn1-c1ccc(Cl)cc1] | C$_{22}$H$_{20}$ClN$_7$O$_2$ | 248-250 |
| 75 | 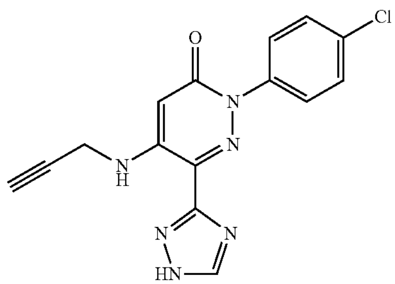 [SMILES: C#CCNc1cc(=O)n(-c2ccc(Cl)cc2)nc1-c1nc[nH]n1] | C$_{15}$H$_{11}$ClN$_6$O | 252-254 |
| 76 | 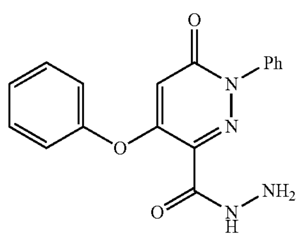 [SMILES: NNC(=O)c1nn(-c2ccccc2)c(=O)cc1Oc1ccccc1] | C$_{17}$H$_{14}$N$_4$O$_3$ | 80-82 |
| 77 | 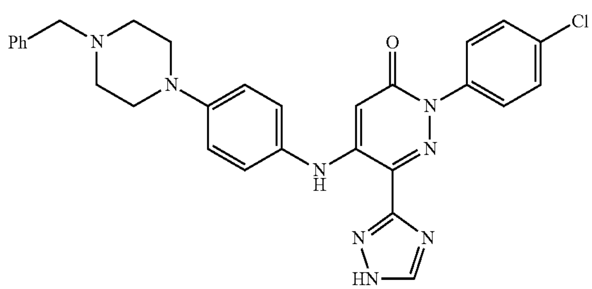 [SMILES: O=c1cc(Nc2ccc(N3CCN(Cc4ccccc4)CC3)cc2)c(-c2nc[nH]n2)nn1-c1ccc(Cl)cc1] | C$_{29}$H$_{27}$ClN$_8$O | 248-251 |
| 78 | 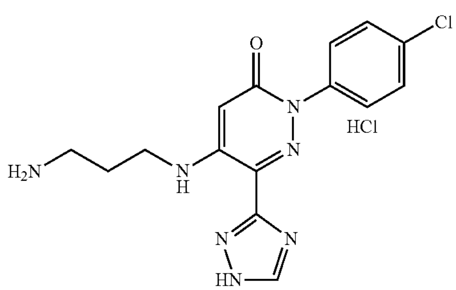 [SMILES: NCCCNc1cc(=O)n(-c2ccc(Cl)cc2)nc1-c1nc[nH]n1 ; Cl] | C$_{15}$H$_{17}$Cl$_2$N$_7$O | 285-290 |

TABLE 1-continued

| Number | Structure | Formula. | m.p. (° C.) |
|---|---|---|---|
| 79 | 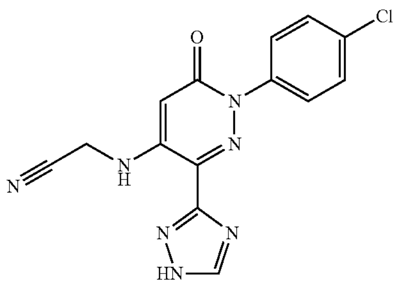 [SMILES: N#CCNc1cc(=O)n(-c2ccc(Cl)cc2)nc1-c1nc[nH]n1] | C₁₄H₁₀ClN₇O | 303-306 |
| 80 | 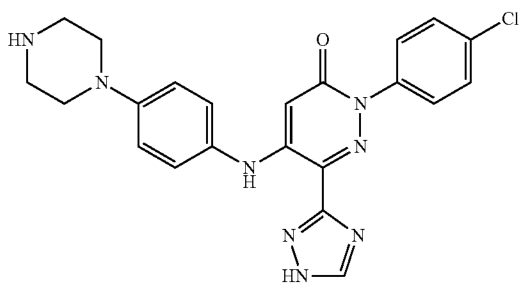 [SMILES: O=c1cc(Nc2ccc(N3CCNCC3)cc2)c(-c2nc[nH]n2)nn1-c1ccc(Cl)cc1] | C₂₂H₂₁ClN₈O | 212-224 |
| 81 | (HCl) | C₂₄H₂₅Cl₂N₇O | 218-221 |
| 82 | 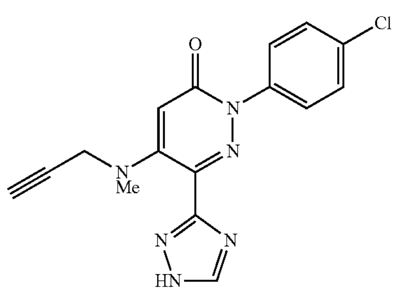 [SMILES: C#CCN(C)c1cc(=O)n(-c2ccc(Cl)cc2)nc1-c1nc[nH]n1] | C₁₆H₁₃ClN₆O | 210-212 |
| 83 | 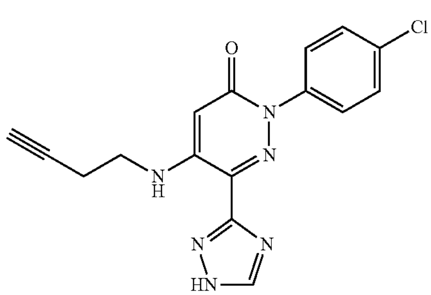 [SMILES: C#CCCNc1cc(=O)n(-c2ccc(Cl)cc2)nc1-c1nc[nH]n1] | C₁₆H₁₃ClN₆O | 176-177 |

The compounds of the present invention can be prepared by methods known in the art. For example compounds of formula (I) or (I') can be prepared by one of the following routes A-E.

Route A:

The compounds of formula (I) or (I'), where $R_2$ is triazolyl, may be prepared by reacting a compound of formula (IIa)

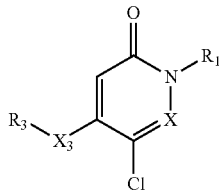

(IIa)

with triazole in the presence of NaH.

Route B:

The compounds of formula (I) or (I'), wherein X, $R_1$, and $X_3$ and $R_3$ are as defined above, $R_2$ is H, and $R_4$ is optionally substituted phenyl or 5 to 6 membered heterocyclic ring may be prepared by reacting a compound of formula (IIb)

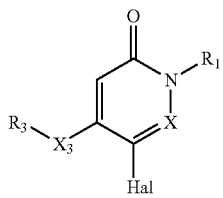

(IIb)

with a compound of formula (IIIb),

Het-B(OR')$_2$ (IIIb)

wherein R' is alkyl and Het is optionally substituted phenyl or 5 to 6 membered heterocyclic ring.

Route C:

The compounds of formula (I) or (I'), wherein X is N and $R_1$ is as defined above, $R_2$ is H, $X_3$ is O and $R_3$ is H and $R_4$ is —C(=O)$X_4R_{41}$ as defined above, may be prepared by reacting a compound of formula (IV),

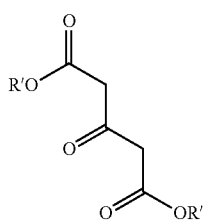

(IV)

wherein R' is alkyl, with a compound of formula (IIIc),

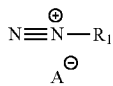

(IIIc)

wherein $R_1$ is as defined above and A is anion, and heating the obtained compound, to obtain a first compound of formula (I) wherein $X_4$ is O and $R_{41}$ is alkyl, and, if desired, reacting the obtained compound with acid, to obtain a second compound of formula (I) or (I') wherein $X_4$ is O and $R_{41}$ is H, and, if further desired, reacting the said second compound with a compound of formula (V), $R_{41}$—NH$_2$ (V)

wherein $R_{41}$ is as defined above, to obtain a third compound of formula (I'), wherein $X_4$ is NH and $R_{41}$ is as defined above, or alternatively reacting the said second compound with compound of formula (VI), $R_{41}$—$X_4$H (VI)

wherein $X_4$ is O or S, and $R_{41}$ is as defined above, to obtain a fourth compound of formula (I) or (I'), wherein $X_4$ is O or S and $R_{41}$ is as defined above.

Route D:

The compounds of formula (I) or (I'), wherein X, $R_1$, $R_2$, and $R_4$ are as defined above and $R_3$ is $X_3R_{31}$, $N_3$ or $NR_{32}R_{33}$ may be prepared by reacting a compound of formula (IId),

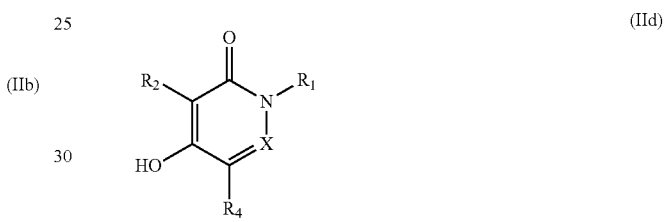

(IId)

wherein X, $R_1$, $R_2$, and $R_4$ are as defined above, with POCl$_3$ and reacting the thus obtained compound with NaN$_3$ or with a compound of formula (IIId), $R_3$—$X_3$H (IIId)

wherein $X_3$ is O or S and $R_3$ are as defined above, to obtain a first compound of formula (I) or (I'), wherein $X_3$ and $R_3$ taken together is $N_3$ or $X_3$ is O or S and $R_3$, is as defined above, respectively, and, if desired, reacting the latter said first compound, wherein X3 and $R_3$ taken together is alkoxy with a compound of formula (VIId), $R_3R_3$'NH (VIId)

wherein $R_3$ and $R_3$' are as defined above when $X_3$ is N, to obtain a second compound of formula (I) or (I'), wherein X3 is NR$_3$'.

Route E:

The compounds of formula (I) or (I'), wherein X is CH and $R_1$ is as defined above, $R_2$ is H, $X_3R_3$ is OH and $R_4$ is —C(=O)$X_4R_{41}$ as defined above, may be prepared by reacting compound of formula (IV),

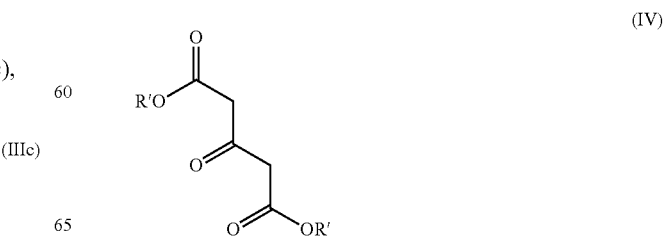

(IV)

wherein R' is alkyl with compound of formula (IIIe),

wherein $R_1$ is as defined above, and treating the obtained compound with acid, to obtain a first compound of formula (I) or (I') wherein $X_4$ is O and $R_{41}$ is H, and, if desired, reacting the said first compound with compound of formula (VI),

wherein $X_4$ is O or S, and $R_{41}$ is as defined above, to obtain a second compound of formula (I) or (I'), wherein $X_4$ is O or S and $R_{41}$ is as defined above, and, if further desired, reacting the said second compound of formula (I) wherein $X_4$ is O and $R_{41}$ is alkyl, with a compound of formula (V)

wherein $R_{41}$ is as defined above, to obtain a third compound of formula (I), wherein $X_4$ is NH and $R_{41}$ is as defined above.

The reactions may be carried out in conventional manner using method well-known to a person skilled in the art.

The pyridazinone and pyridone compounds of Formula (I) or (I') can be used as a medicament, preferably in the treatment or prevention of inflammation, a disease caused by inflammation, or a disease which causes inflammation, or immune or autoimmune disorder. The compounds of present invention can especially be used SSAO/VAP-1 related diseases such as inflammatory diseases or conditions, diseases related to carbohydrate metabolism and complications thereof, diseases related to aberrations in adipocyte differentiation or function, vascular diseases and fibrotic conditions.

Examples of inflammatory diseases and conditions include, but are not limited to, connective tissue inflammatory conditions and diseases such as ankylosing spondylitis, Reiter's syndrome, arthritis, rheumatoid arthritis, systemic juvenile rheumatoid arthritis, osteoarthritis, psoriatic arthritis, synovitis, vasculitis, Sjögren's syndrome, Bechçet's syndrome, relapsing polychondritis, systemic lupus erythematosus, discoid lupus erythematosus, systemic sclerosis, eosinophilic fasciitis, polymyositis, dermatomyositis, polymyalgia rheumatica, temporial arteritis, polyarteritis nodosa, Wegener's granulomatosis, and mixed connective tissue disease; gastrointestinal inflammatory diseases and conditions including Crohn's disease, ulcerative colitis, inflammatory bowel disease and irritable bowel syndrome (spastic colon), fibrotic conditions of the liver, inflammation of the oral mucosa (stomatitis), and recurrent aphtous stomatitis; central nervous system inflammatory diseases and conditions such as multiple sclerosis, epilepsy, Alzheimer's disease, vascular dementia, and ischemia-reperfusion injury associated with ischemic stroke; pulmonary inflammatory diseases and conditions including asthma, chronic obstructive pulmonary disease and acute respiratory distress syndrome and adult respiratory distress syndrome; inflammatory diseases and conditions of the skin such as contact dermatitis, atopic dermatitis, psoriasis, pityriasis rosea, lichen planus and pityriasis rubra pilaris; f[iota]brotic diseases including idiopathic pulmonary fibrosis, cardiac fibrosis and systemic sclerosis (scleroderma); systemic inflammatory response syndrome (sepsis); and inflammatory and/or autoimmune diseases and conditions of the liver including autoimmune hepatitis, primary biliary cirrhosis, alcoholic liver disease, sclerosing cholangitis, and autoimmune cholangitis.

The compounds of the present invention can also be used to treat diseases related to carbohydrate metabolism, such as diabetes, both type I and II, and complications thereof including, but not limited to, atherosclerosis, vascular retinopathies, retinopathy, nephropathy, nephritic syndrome, polyneuropathy, mononeuropathies, autonomic neuropathy, foot ulcers, joint problems, and increased risk of infection; diseases related to or caused by aberrations in adipocyte differentiation or function or smooth cell function such as atherosclerosis and obesity; and vascular diseases such as chronic heart failure, congestive heart failure, atheromatous arteriosclerosis, nonatheromatous arteriosclerosis, ischemic heart disease, myocardial infraction, stroke, ischemia-reperfusion injury, peripheral arterial occlusion, thromboangiitis obiliterans (Buerger's disease), and Raynaud's disease and phenomenon.

Examples of the fibrotic condition include, but are not limited to, liver fibrosis and the inflammatory conditions which predispose to it i.e. acute and chronic hepatitis, biliary disease and toxic liver injury, pulmonary fibrosis, renal fibrosis, including that resulting from diabetic nephropathy, myelofibrosis, pancreatic fibrosis, scleroderma, connective tissue diseases, scarring, skin fibrosis, cardiac fibrosis, organ transplant, vascular stenosis, restenosis, arterial fibrosis, arthrofibrosis, breast fibrosis, muscle fibrosis, retroperitoneal fibrosis, thyroid fibrosis, lymph node fibrosis, bladder fibrosis, pleural fibrosis and COPD, a disease in which airway walls are fibrotic with the accumulation of myofibroblasts and collagen, and like all fibrotic tissues, are contracted.

"Treatment or prevention" as used herein includes prophylaxis, or prevention of, as well as lowering the individual's risk of falling ill with the named disorder or condition, or alleviation, amelioration, elimination, or cure of the said disorder once it has been established.

The compounds of the present invention may be administered in an effective amount within the dosage range of about 0.1 µg/kg to about 300 mg/kg, preferably between 1.0 µg/kg to 10 mg/kg body weight. Compounds of the present invention may be administered in a single daily dose, or the total daily dosage may be administered in divided doses of two, three or four times daily.

"An effective amount" refers to an amount of a compound that confers a therapeutic effect on the treated subject. The therapeutic effect may be objective (i.e. measurable by some test or marker) or subjective (i.e. subject gives an indication of or feels an effect). Such treatment need not necessarily completely ameliorate the condition of disease. Further, such treatment or prevention can be used in conjunction with other traditional treatments for reducing the condition known to those skilled in the art.

There is also provided as a further aspect of this invention a pharmaceutical composition comprising an effective amount of one or more pyridazinone and/or pyridone compound(s) of formula (I) or (I') of the present invention in combination with one or more pharmaceutically acceptable carrier, i.e. one or more pharmaceutically acceptable carrier substances (or vehicles) and/or additives (or excipients) and/or other active ingredients.

The pharmaceutical compositions can contain one or more of the pyridazinone and/or pyridone compounds of the invention. The pharmaceutical compositions of the present invention can be administered to any animal that can experience the beneficial effects of the compounds of the invention. Foremost among such animals are humans, although the invention is not intended to be so limited. Product comprising one or more compounds of the invention and one or more other active ingredient may be used as combined preparation for simultaneous, separate or sequential use in therapy.

The pharmaceutical compositions of the present invention can be administered by any means that achieve their intended purpose. Examples of such administrations include, but are not limited to, parenteral, subcutaneous, intravenous, intraarticular, intrathecal, intramuscular, intraperitoneal, and by intradermal injections, and via transdermal, rectal, buccal, oromucosal, nasal, ocular routes and via inhalation and via implant. Alternatively, or concurrently, administration can be by the oral route. Particularly preferred is oral administration. The dosage administered will be dependent upon the severity of the condition of the recipient, for example and the age, health, sex, medical history and weight of the recipient, kind of concurrent treatment, if any, frequency of treatment, and the nature of the effect desired. The dose can also vary depending upon whether it is to be administered in a veterinary setting to an animal or to a human patient.

In addition to the pharmacologically active compounds, the pharmaceutical compositions of the compounds can contain suitable pharmaceutically acceptable carriers comprising excipients and auxiliaries that facilitate processing of the active compounds into preparations that can be used pharmaceutically. The pharmaceutical compositions of the present invention are manufactured in a manner that is, itself, know, for example, by means of conventional mixing, granulating, dragee-making, dissolving, lyophilizing, or similar process. Thus, pharmaceutical compositions of oral use can be obtained by combining the active compounds with solid excipients, optionally grinding the resulting mixture and processing the mixture of granules, after adding suitable auxiliaries, if desired or necessary, to obtain tablet or dragee cores.

Such excipients are, in particular, fillers such as saccharides, for example, lactose or sucrose, mannitol or sorbitol, cellulose and/or starch preparations and/or calcium phosphates, for example, tricalcium phosphate or calcium hydrogen phosphate, as well as binders, such as starches and their derivatives and/or pastes, using, for example, maize starch, wheat starch, rice starch, potato starch, gelatine, tragachant, methyl cellulose, hydroxypropylmethyl cellulose, sodium carboxymethyl cellulose, and/or polyvinyl pyrrolidone, derivatives, and/or, if desired, disintegrating agents, such as the above-mentioned starches and also carboxymethyl starch, cross-linked polyvinyl pyrrolidone, agar, or alginic acid or a salt thereof, such as sodium alginate. Auxiliaries are, above all, flow-regulating agents and lubricants, for example, silica, talc, stearic acid, or salts thereof, such as magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures, but also film coating using e.g. cellulose derivatives, polyethylene glycols and/or PVP derivatives may be used. In order to produce coatings resistant to gastric juices, solutions of suitable cellulose preparations such as acetyl cellulose phthalate or hydroxypropylmethyl cellulose phthalate, are used for coating. Slow-release and prolonged-release compositions may be used with particular excipients such as methacrylic acid—ethylacrylate copolymers and methacrylic acid—methyl methylacrylate copolymers. Dyestuffs or pigments may be added to the tablets or dragee coatings or to coatings for example, for identification or in order to characterize different combinations of active compound doses.

Other pharmaceutical compositions that can be used orally include push-fit capsules made of gelatine, as well as soft, sealed capsules made of gelatine and a plasticizer such as glycerol or sorbitol. The push-fit capsules can contain the active compounds in the form of granules that may be mixed with fillers such as lactose, binders such as starches, and/or lubricants such as talc or magnesium stearate and, optionally stabilizers. In soft capsules, the active compounds are preferably dissolved or suspended in suitable liquids such as fatty oils or liquid paraffin. In addition, stabilizers may be added.

Suitable compositions for parenteral administration include sterile aqueous and non-aqueous solvents. The compounds of the present invention may also be administered parenterally by using suspensions and emulsion as pharmaceutical forms. Examples of useful non-aqueous solvents include propylene glycol, polyethylene glycol, vegetable oil, fish oil, and injectable organic esters. Examples of aqueous carriers include water, water-alcohol solutions, emulsions, or suspensions, including saline and buffered medical parenteral vehicles including sodium chloride solution, Ringer's dextrose solution, dextrose plus sodium chloride solution, Ringer's solution containing lactose, or fixed oils. Examples of solubilizers and co-solvents to improve the aqueous properties of the active compounds to form aqueous solution to form parenteral pharmaceutical dosage forms are propylene glycol, polyethylene glycols and cyclodextrins. Examples of intravenous infusion vehicles include fluid and nutrient replenishers, electrolyte replenishers, such as those based upon Ringer's dextrose and the like.

Injectable preparation, such as solutions, suspensions, or emulsions, may be formulated according to known art, using suitable dispersing or wetting agents and suspending agents, as needed. When the active compounds are in water-soluble form, for example, in the form of water soluble salts, the sterile injectable preparation may employ a non-toxic parenterally acceptable diluent or solvent as, for example, water for injection. When the active compounds are in a non-water soluble form, sterile, appropriate lipophilic solvents or vehicles, such as fatty oil, for example, sesame oil, or synthetic fatty acid esters, for example, ethyl oleate, triglycerides or polyethylene glycol, are used. Alternatively, aqueous injection suspensions can contain substances which increase the viscosity, for example, sodium carboxymethyl cellulose, sorbitol, and/or dextran. Optionally, the suspension may also contain stabilizers.

Furthermore, the compounds of formula (I') can be used as synthesis intermediates for the preparation of other compounds, in particular of other pharmaceutically active ingredients, which are obtainable from the compounds of formula (I'), for example by introduction of substituents or modification of functional groups.

Pharmacological Tests
In Vitro Inhibition of VAP-1 SSAO Activity

VAP-1 SSAO activity was measured using the coupled colorimetric method essentially as described for monoamine oxidase and related enzymes (Holt, A., et al., *Anal. Biochem.* 244:384-392 (1997)). Recombinant human VAP-1 SSAO expressed in Chinese Hamster Ovary (CHO) cells was used as a source of VAP-1 SSAO for activity measurements. Native CHO cells have negligible SSAO activity. These cells and their culture have previously been described (Smith, D. J., et al., *J. Exp. Med.* 188:17-27 (1998)). A cell lysate was prepared by suspending approximately $3.6 \times 10^8$ cells in 25 ml lysis buffer (150 mM NaCl, 10 mM Tris-Base pH 7.2, 1.5 mM $MgCl_2$, 1% NP40) and incubating at 4° C. overnight on a rotating table. The lysate was clarified by centrifugation at 18 000 g for 5 min at room temperature and the supernatant used directly in the assay. The VAP-1 SSAO assay was performed in 96 well microtitre plates as follows. To each well was added a predetermined amount of inhibitor if required. The amount of inhibitor varied in each assay but was generally at a final concentration of between 1 nM and 50 μM. Controls lacked inhibitor. The inhibitor was in a total volume of 20 μl in water.

The following reagents were then added. 0.2 M potassium phosphate buffer pH 7.6 to a total reaction volume of 200 µl, 50 µl of freshly made chromogenic solution containing 1 mM vanillic acid, 500 µM 4-aminoantipyrine and 8 U/ml horseradish peroxidase and an amount of CHO cell lysate containing VAP-1 SSAO that caused a change of 0.6 $A_{490}$ per h. This was within the linear response range of the assay. The plates were incubated for 30 min at 37° C. and the background absorbance measured at 490 nm using a Wallac Victor II multilabel counter. To initiate the enzyme reaction 20 µl 10 mM benzylamine (final concentration=1 mM) was added and the plate incubated for 1 h at 37° C. The increase in absorbance, reflecting VAP-1 SSAO activity, was measured at 490 nm. Inhibition was presented as percent inhibition compared to control after correcting for background absorbance and $IC_{50}$ values calculated using GraphPad Prism.

Comparison of VAP-1 SSAO Activity Versus Total Rat MAO Activity

Rat MAO was prepared from rat liver by rinsing the 1 g liver sample several times in 14 ml KCl-EDTA-solution to remove all blood. Then 1 g liver sample was homogenized in 4 ml ice-cold potassium phosphate buffer (0.1 M, pH 7.4) with an Ultra-Turrax homogenizer (setting 11 000 rpm, 4× 10 s). After centrifugation at 500 g for 10 min at 4° C. the supernatant was carefully withdrawn and was centrifuged at 12 300 g for 15 min at 4° C. The supernatant was discharged and sedimented mitochondria were resuspended in 4 ml fresh phosphate buffer and centrifuged as previously. The mitochondria were suspended in 4 ml phosphate buffer and homogenized with an Ultra-Turrax homogenizer (setting 11 000 rpm, 2×10 s). Mitochondrial preparate was aliquoted and stored at −70° C. Total MAO activity was measured in a similar way as for VAP-1 SSAO except that SSAO enzyme was replaced by MAO enzyme. To each well was added a predetermined amount of inhibitor if required. The amount of inhibitor varied in each assay but was generally at a final concentration of between 10 nM and 800 µM. Controls lacked inhibitor. The inhibitor was in a total volume of 20 µl in water. The following reagents were then added. 0.2 M potassium phosphate buffer pH 7.6 for a total reaction volume of 200 µl, 50 µl of freshly made chromogenic solution (as above) and 50 µl of MAO preparation (or needed amount of MAO). The plates were incubated for 30 min at 37° C. and the background absorbance measured at 490 nm using a Wallac Victor II multilabel counter. To initiate the enzyme reaction 20 µl of 5 mM tyramine (final concentration 0.5 mM) was added and the plate incubated for 1 h at 37° C. The increase in absorbance, reflecting MAO activity, was measured at 490 nm. Inhibition was presented as percent inhibition compared to control after correcting for background absorbance and $IC_{50}$ values calculated using GraphPad Prism. Clorgyline and pargyline (inhibitors of MAO-A and -B respectively) at 0.5 µM were added to some wells as positive controls for MAO inhibition.

The ability of compounds of Examples 13 to 83 to inhibit VAP-1 SSAO activity with specificity for VAP-1 SSAO over rat MAO is shown in Table 2. The results indicate that the compounds of the invention are specific inhibitors of human VAP-1 SSAO activity. The compounds of the present invention are therefore expected to have therapeutic utility in the treatment of diseases and conditions in which the SSAO activity of the human adhesion molecule VAP-1 plays a role.

TABLE 2

POTENCY AND SPECIFICITY OF EXAMPLE COMPOUNDS

| Compound code | VAP-1 SSAO Inhibitory activity $IC_{50}$ (µM) | Total MAO Inhibitory activity (%) |
| --- | --- | --- |
| 13 | 15 | 0% at 100 µM |
| 14 | 0.37 | 0% at 100 µM |
| 16 | 0.64 | 24% at 100 µM |
| 17 | 236 | 22% at 100 µM |
| 22 | ~60 | 0% at 100 µM |
| 25 | 0.35 | 0% at 100 µM |
| 27 | 2.0 | 3% at 100 µM |
| 28 | 3.6 | 10% at 100 µM |
| 29 | 0.27 | 9% at 100 µM |
| 34 | 1.60 | 24% at 100 µM |
| 36 | 16 | 3% at 100 µM |
| 39 | 2.0 | 8% at 100 µM |
| 42 | 0.72 | 2% at 100 µM |
| 43 | 0.078 | 5% at 100 µM |
| 46 | 0.34 | 9% at 100 µM |
| 52 | 3.5 | 9% at 100 µM |
| 54 | 0.28 | 0% at 100 µM |
| 57 | 0.044 | 5% at 100 µM |
| 58 | 0.17 | 5% at 100 µM |
| 59 | 0.080 | 14% at 250 µM |
| 61 | 0.30 | 17% at 250 µM |
| 62 | 0.28 | 21% at 250 µM |
| 63 | 0.070 | 5% at 50 µM |
| 65 | 0.063 | 8% at 250 µM |
| 68 | 0.18 | 6% at 250 µM |
| 70 | 0.14 | 18% at 50 µM |
| 71 | 0.17 | 16% at 50 µM |
| 73 | 2.2 | 0% at 50 µM |
| 74 | 0.10 | 0% at 50 µM |
| 75 | 0.22 | 0% at 50 µM |
| 77 | 0.35 | 24% at 50 µM |
| 78 | 0.80 | 3% at 50 µM |
| 81 | 0.031 | 5% at 50 µM |
| 83 | 0.073 | 0% at 50 µM |

TEST EXAMPLES

All animal experiments are performed in transgenic mice expressing human VAP-1/SSAO. Such mice can be made, for instance, crossing human AOC3 (hAOC3) knock-in mice, in which the native mouse AOC3 gene function has been eliminated by replacing the mouse AOC3 gene with the human AOC3 gene using gene targeting technology by homologous recombination in embryonic stem cells which are then injected into blastocytes generating chimeric mice from which homozygous hAOC3 transgenic knockout mice can be derived by breeding and selection for mice contain the hAOC3 transgene, with mice with a desired genotype and selecting for progeny which contain the hAOC3 knock-in gene on a desired background.

All animal experiments are performed in accordance with standards of ethical conduct and appropriate institutional animal care and use policies.

Test Example 1

In Vivo Effects of SSAO Inhibitors on Excretion of Urinary Methylamine

This study was performed in order to determine the activity of the present SSAO inhibitors in vivo. To this end, the excretion of methylamine, a natural SSAO substrate, in the urine of transgenic mTIEhVAP1 mice expressing full length human VAP-1 in endothelial tissues under mouse TIE-1 promoter was determined. The mTIEhVAP1 mice were produced as described by Stolen et al. in Circulation Research 2004; 95:50-57.

Transgenic mice were administered with either the present SSAO inhibitors (5 mg/kg i.p.) on study days 1 and 2, or with a known hydrazine SSAO inhibitor, namely (1S,2R)-2-(1-methylhydrazino)-1,2-diphenylethanol (BTT-2079) disclosed e.g. by Nurminen et al. in J. Med. Chem. 2011 (in press), (5 mg/kg i.p.) on study day 1. Urine was collected pre-dose and after dosing in 0-24 h, 42-48 h and 48-72 h fractions. Urinary methylamine was measured as described elsewhere (Am. J. Pathology 168 (2006) 718-726, Analytical Biochem 384 (2009) 20-26 and J. Pharm. Pharmacol. 1989, 41: 97-100). The measured concentrations in the collected fractions were used to calculate the total urinary excretion of each mouse.

The effect of Compound 43 (grey column) and BTT-2079 (white column) on the daily urinary excretion of methylamine is shown in FIG. 1. Similar results are obtained with other SSAO inhibitors disclosed herein.

Test Example 2

Renoprotective Effects of SSAO/VAP-1 Inhibitors in Mouse Model of Diabetic Kidney Disease Diabetes can cause diabetic nephropathy (DN) associated with progressive renal fibrosis, eventually reducing functioning renal mass. To assess the effect of SSAO inhibitors on renal fibrosis, a well-established Db/db diabetic mouse model for diabetic kidney disease is employed.

Diabetic db/db mice and db/m control mice are further made transgenic with human VAP-1. Such mice can be made crossing human AOC3 (hAOC3) knock-in mice obtained as described above, in which the native mouse AOC3 gene function has been eliminated, with db/db mice and selecting for hAOC3 db/db or hAOC3 db/m progeny which contain the hAOC3 knock-in gene on either a db/db or db/m background.

All aspects of these experiments (housing, experimentation and disposal of animals) are performed in general accordance with the Guide for the Care and Use of Laboratory Animals (National Academy Press, Washington, D.C., 1996).

A test substance is evaluated for possible renoprotective effect in a mouse model of diabetic nephropathy. The test substance and a vehicle are administered intraperitoneally (IP) once daily for 42 consecutive days to male db/db mice (BKS Cg-Lepr db/Lepr db) at the age of 15 weeks when non-insulin dependent diabetes mellitus is fully established. Db/m mice serve as lean normal controls. The db/db mice show elevated plasma creatinine, signifying impaired kidney function, as well as hyperglycemia and dyslipidemia (LDL, total cholesterol and triglycerides) in comparison to db/m mice. The diabetic mice are associated with obesity, polyuria, albuminuria and increased fractional urinary $Na^+$ excretion (FENa), indicating impaired tubular $Na^+$ reabsorption. The endogenous creatinine clearance (CCr), an estimate of glomerular filtration rate, tends to be lower in the diabetic mice vs db/m mice.

At the completion of the in-life phase necropsies are performed, including collecting and preserving tissues. The right kidney from all animals is fixed in 10% neutral buffered formalin. Longitudinal sections are trimmed and processed to paraffin blocks, sectioned at 3 microns and stained by periodic acid Schiff (PAS) for evaluation by light microscopy. Mesangial matrix expansion is scored in 50 glomeruli per kidney according to the semi-quantitative scoring scheme outlined in the protocol below.

Fifty glomeruli from each kidney are scored for mesangial matrix expansion according to the following system.

Minimal: grade 1, 0-25% of glomerular volume occupied by matrix
Mild: grade 2, 25-50% of glomerular volume occupied by matrix
Moderate: grade 3, 50-75% of glomerular volume occupied by matrix
Severe: grade 4, 75-100% of glomerular volume occupied by matrix Little glomerular mesangial matrix is be seen in normal animals but expansion of the mesangial matrix is characteristic of a variety of disease states such as diabetes mellitus. The mesangial matrix includes the basement membrane and associated polyanionic proteoglycans and other molecules which are stained red to purple by the periodic acid Schiff (PAS) method. Thus, the amount of PAS positive material in the glomerulus is a measure of the amount of mesangial matrix present.

Fifty glomeruli from each animal are evaluated at a magnification of 200× and scored for expanded mesangial matrix using the scoring system described above. Mean group mesangial matrix expansion scores are calculated by summing the scores for each glomerulus evaluated for each animal. The mesangial matrix expansion scores for all animals in the group are then summed and divided by the number of animals per group to obtain the mean group mesangial matrix expansion score.

The present SSAO inhibitors result in a dose-related reduction in the mesangial matrix expansion score as compared to the mesangial matrix expansion score in the non-treated db/db non-insulin dependent diabetes mellitus mice.

Test Example 3

Unilateral Uretreal Obstruction

Renal Fibrosis Model

Transgenic mTIEhVAP1 mice obtained as described in Example 1 are dosed with a vehicle or test substance intraperitoneally five days pre-operatively and 7 days post-operatively. The inhibitor and vehicle is injected every second day at an appropriate amount to inhibit SSAO. All animals are given normal laboratory chow and water ad libitum.

Male mice aged 6-7 weeks (20-25 g body weight) are anesthetised with isoflurane (2-chloro-2-(difluoromethoxy)-1,1,1-trifluoro-ethane) inhalation and injected subcutaneously with 0.05-0.1 mg/kg buprenorphine pre-operatively. The mice are subjected to unilateral ureteral obstruction (UUO) or a sham operation. In UUO operated mice, the left ureter is ligated with a 4-0 silk suture at two points and cut between the ligatures in order to prevent retrograde urinary tract infection. The mice are sacrificed 7 days post-operatively.

Renal injury is assessed biochemically, by measuring the urine albumin excretion and creatinine clearance, and further, histologically by Masson trichrome and Periodic acid Schiff staining.

One-way ANOVA and Dunnett's tests are used in all studies to ascertain significant differences between treated and vehicle groups. Differences are considered significant at *$P<0.05$.

A reduction in renal fibrosis, as evidenced by statistically significant reductions in scoring in comparison to controls, can be shown.

Test Example 4

Effects of VAP-1 Inhibitors on Neointimal and Medial Fibrosis in the Vascular Wall Neointimal and medial thickening is an early and essential stage in the development of atherosclerotic lesions and an essential component of restenosis. It is accompanied by fibrotic changes in the neointima and media of the vascular wall. This study evaluates the role of blocking SSAO in fibrotic disease by evaluating the effect of systemic delivery (by daily ip injection) of a test substance (a small molecule SSAO inhibitor) on cuff-induced neointimal thickening (cuff-induced stenosis) in the femoral artery of ApoE3 Leiden mice containing a human AOC3 gene instead of the native mouse AOC3 gene (an hAOC3 knock-in mouse made as described above) that received a moderate western type diet.

Methods: 40 male hAOC3 ApoE3*Leiden mice (age 12 weeks) are fed a mildly hypercholesterolemic diet for 3 weeks prior to surgical cuff placement. Treatment was daily ip injections with 1) vehicle; 2) dexamethasone in drinking water at 9 mg/l; 3) daily ip injections of the test substance at 10 mg/kg; 4) the substance at 30 mg/kg, all started one day prior to surgery and continued during the experimental period. At day 0 surgery is performed, i.e. a non-constricting cuff (2-3 mm in length) is placed around both femoral arteries of the mice. 10 mice of each group are sacrificed after 2 weeks for histomorphometric analysis to quantify the inhibition of accelerated atherosclerotic lesions and neointima formation. A significant reduction in media and neointima formation in the dexamethasone-treated positive control group and both test substance-treated groups compared to the NaCl 0.9% treated control group is seen. This is reflected in the increased lumen size in examples of HPS stained vessel segments in SSAO inhibitor treated groups when compared to a control group. Vascular integrity is not affected.

These studies show that systemic dosing with SSAO inhibitors results in less neointimal thickening (neointimal fibrosis) in the ApoE 3 Leiden mice cuff model when compared with a control treated group.

Test Example 5

Liver Fibrosis

Mice on a methionine choline deficient (MCD) diet develop profound steatosis (fatty liver) with inflammation at 6-8 weeks and subsequently fibrosis. This is an accepted model of NASH (non-alcoholic steatohepatitis) and may thus be used to study the effect of a test substance on reducing features of NASH such as hepatic inflammation and fibrosis (collagen and connective tissue content).

C57Bl/6 mice containing a human AOC3 gene instead of the native mouse AOC3 gene (an hAOC3 knock-in mouse) are made by replacing the mouse AOC3 gene with the human AOC3 gene using gene targeting technology by homologous recombination in embryonic stem cells which are then injected into blastocytes generating chimeric mice from which homozygous hAOC3 transgenic knockout mice can be derived by breeding and selection for mice contain the hAOC3 transgene.

Two groups of 4 to 8 C57Bl/6 hAOC3 mice are each fed an MCD diet for 6 weeks. One group receives the test substance at appropriate dosing intervals and via an appropriate route and the other receives vehicle only. After six weeks the mice are sacrificed and the collagen and connective tissue content of the livers of the two groups can be assessed and compared by Van Gieson staining and quantification of the degree of staining in the two groups. The degree of inflammation in the livers of the two groups can be assessed and compared by staining liver sections with H&E stain and microscopically counting inflammatory foci. Appropriate statistical tests are used in all studies to ascertain significant differences between treated and vehicle groups. Differences are considered significant at *P<0.05.

A reduction in fibrosis and inflammation, as evidenced by statistically significant reductions in scoring in comparison to controls, can be shown.

Test Example 6

Inhibition of Collagen-Induced Arthritis in Mouse

Mouse collagen-induced arthritis (CIA) is a frequently used model both for studying the basic mechanisms of autoimmune arthritis and in assessing the efficacy of potential antiarthritic agents.

The study is conducted with groups of 14 mice to obtain statistically valid results. DBA/1 mice are further made transgenic with human VAP-1. Such mice can be made crossing human AOC3 (hAOC3) knock-in mice, in which the native mouse AOC3 gene has been replaced with a human AOC3 gene, with DBA/1 mice and selecting for hAOC3 DBA/1 progeny which contain the hAOC3 knock-in gene on a DBA/1 background.

For arthritis induction hAOC3 DBA/1 mice (male, aged 10-12 weeks, approximate weight 25 g, disclosed e.g. in U.S. Pat. No. 6,624,202) are immunized with bovine type II collagen (100 µg) emulsified in Freund's complete adjuvant by four subcutaneous injections in the back. At day 21, animals are boosted with an i.p. injection of 100 µg collagen type II diluted in PBS. This strain is highly susceptible to CIA induced with bovine type II collagen. After the second immunization, polyarthritis starts to develop in 1 to 2 weeks, with a disease incidence of approx. 80% at day 38 (Joosten et al., J. Immunol. 159:4094-4102. 1997). Arthritis development is scored from day 21 onwards. Animals are treated for 2.5 weeks starting after the second booster but before the arthritis onset (day 23). Intraperitoneal medication with the present compounds (10 mg kg-1 twice daily) is initiated at day 23 and continued until day 37.

A reduction in the cumulative score (p<0.05 by Dunn's test following Kruskal-Wallis test) is detected.

Test Example 7

Experimental Autoimmune Encephalitis

Relapsing-remitting experimental autoimmune encephalomyelitis (EAE) is a commonly used model of multiple sclerosis (MS). It is induced in SJL/J mice by immunization with myelin proteolipid protein peptide 139-151 (PLP 139-151) in complete Freund's adjuvant (CFA). The SJL/J mice are further made transgenic with human VAP-1. Such mice can be made crossing human AOC3 (hAOC3) knock-in mice, in which the native mouse AOC3 gene has been replaced with a human AOC3 gene, with SJL/J mice and selecting for hAOC3 SJL/J progeny which contain the hAOC3 knock-in gene on a SJL/J background.

This immunization induces a cell-mediated immune response targeting central nervous system (CNS) white matter resulting in paralysis that occurs 10-12 days later. The majority of mice recover from the initial attack of disease within 5-7 days but then go on to develop one or more relapses of paralysis. The relapses are thought to be caused by the activation of cell-mediated immunity to new myelin peptide epitopes, a process referred to as epitope spreading. This model has many features in common with multiple sclerosis including: (1) polyclonal activation of myelin peptide specific T-cells, (2) relapsing-remitting disease course mediated by epitope spreading, (3) involvement of proinflammatory cytokines in the pathogenesis of disease such as TNF-α, IFN-γ, IL-2, and IL-17, (4) neuronal degeneration, (5) and sensitivity to suppression by marketed MS disease modifying agents.

To induce EAE, an emulsion is prepared by mixing equal volumes of PLP 139-151peptide solution (1.5 mg/ml in PBS) with complete Freund's adjuvant (CFA) containing 2 mg/ml of heat-killed *Mycobacterium tuberculosis* strain H37RA (MTB). The complete Freund's adjuvant is prepared by dissolving MTB in incomplete Freund's adjuvant so that a concentration of 2 mg/ml is reached.

For the emulsion of MTB and PLP 139-151 peptide, three 5 ml-batches are prepared containing 2.5 ml CFA and 2.5 ml of PLP 139-151 peptide solution. The mixture is blended on ice for 15-20 min in 5 ml-batches using an Ultra-Turrax T25 dispersing instrument (IKA-Labortechnik, 17 000 rpm). The emulsion is aspirated into 1 ml syringes prior to injection.

Female SJL/J mice containing a human AOC3 gene instead of the native mouse AOC3 gene (an hAOC3 knock-in mouse) are anesthetized by inhalation with isoflurane prior to shaving their hindquarters. Each mouse is subcutaneously injected at 4 sites equally spaced across the rear flank with 50 μl of the PLP 139-151/CFA emulsion (200 μl total). The mice are observed daily and their weight is recorded. Typically, the first clinical signs of EAE became apparent between day 10-12 after immunization. The majority of mice recover from the initial attack of disease within 5-7 days but then go on to develop one or more relapses of paralysis. The severity of EAE is evaluated every day for 40 days using a published and well established scoring regime (Bebo et al., 2001, J. Immunol. 166(3):2080-2089).

All dosing solutions are administrated orally or subcutaneous injection on days 0-15. The dose of the test items is from 5 to 80 mg/kg and dose volume 10 ml/kg (oral) or 20 ml/kg (s.c.).

Clinical symptoms of encephalomyelitis are suppressed by the present SSAO inhibitors. Evaluation is primarily based on the values for disability scoring and of body weight. Where appropriate, analysis of the data by two way ANOVA with Tukey analysis is applied to determine significance of treatment effects.

Test Example 8

LPS-Induced Lung Inflammation

Lipopolysaccharide (LPS)-Induced Acute Lung Inflammation model and resulting Bronchoalveolar Lavage (BAL) Cell Counts as described e.g. in Yu et al., 2006, Am. J. Pathol. 168:718-726 are used to demonstrate a therapeutic activity of the present SSAO inhibitors.

mTIEVAP-1 transgenic mice prepared as described in Example 1 or mice containing a human AOC3 gene instead of the native mouse AOC3 gene (an hAOC3 knock-in mouse made as described above) are anesthetized with halothane. The mice are administered with 50 μl of LPS (2 μg/animal) through the nose with a micropipette. Such a dose is known to produce a maximal neutrophil accumulation in the alveolar space. Control animals receive vehicle only. The mice are sacrificed 24 hours after LPS instillation. BAL is obtained using subsequent washes of 1 ml of saline. Retrieved aliquots are centrifuged and total cell counts are measured combined aliquots resuspended in phosphatebuffered saline (PBS) with a grid hematocytometer. Diff-Quick stain is also used for microscopic examination of the BAL cells. The first cell-free aliquot of BAL fluid is used for biochemical analyses.

The SSAO inhibitors significantly reduce the LPS-induced increase in the BAL cell counts and in TNF-α levels in the BAL fluid.

General Procedures

The following examples illustrate the preparation of compounds of Formula (I) or (I').

General Procedure 1. Synthesis of General Structure (v)

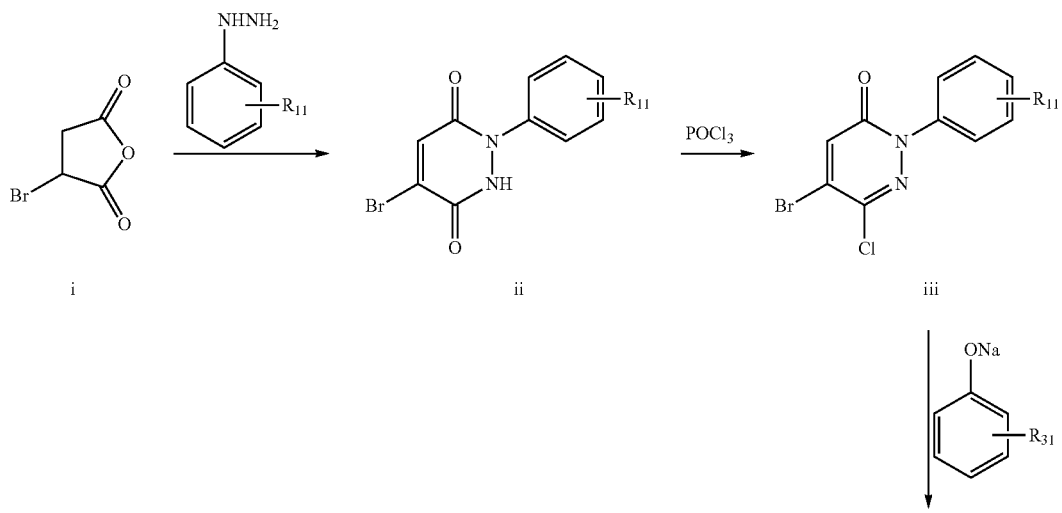

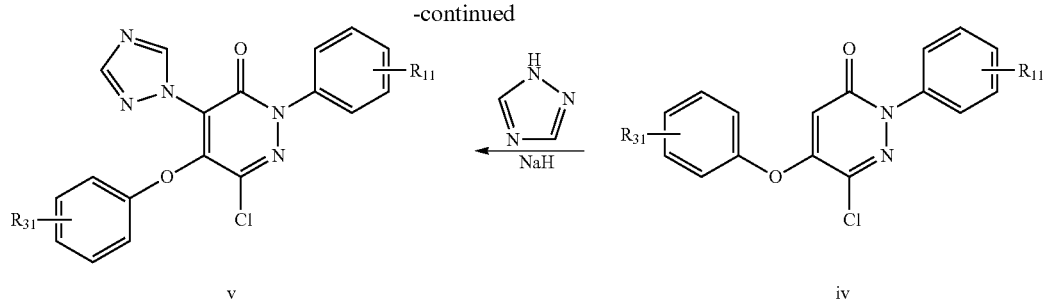

wherein $R_{11}$ is as defined above or H and $R_{31}$ is as defined above or H.

1-Aryl-4-bromo1-phenylpyridazin-3,6(1H,2H)-diones (ii) were prepared from the corresponding arylhydrazines and bromomaleic anhydride (i) (Meier, K.; Ringier, B. H.; Druey, J. *Helv. Chim. Acta* 1954, 37, 523). The bromo→aryloxy exchange was accomplished by using the corresponding phenolates (Balonak, S.; Ostrowicz, A. *Polish J. Chem.* 1990, 64, 741) to yield iv from iii. The attempted exchange of the 6-chloro substituent of iv with 1H-1,2,4-triazole in the presence of NaH took place via a rearrangement reaction to furnish 4-(1H-1,2,4-triazol-1-yl)-substituted derivatives (v).

General Procedure 2. Synthesis of General Structure (viii), (ix), and (x)

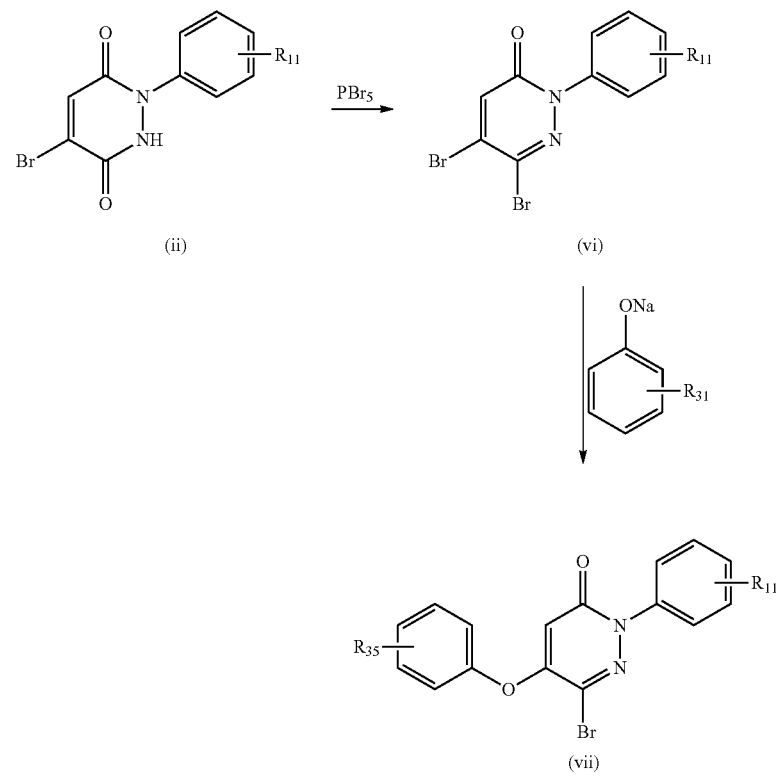

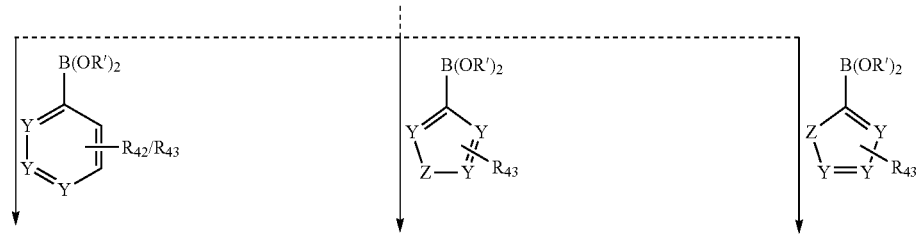

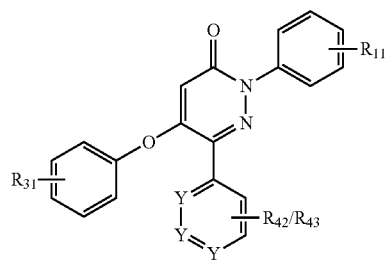
(viii)

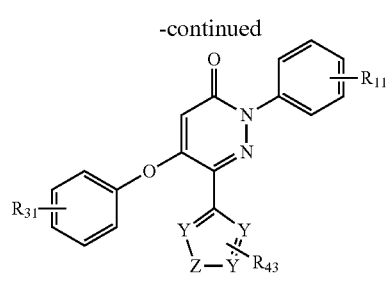
(ix)

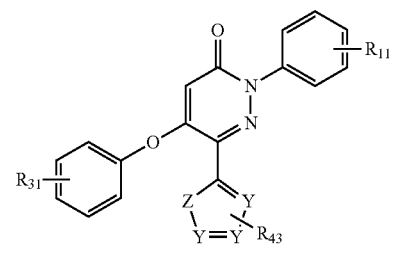
(x)

wherein $R_{11}$, $R_{31}$, $R_{42}$ and $R_{43}$ are independently as defined above or H and each Y is independently CH or N; and Z is O, S, NH or $NR_{43}$.

2-Aryl-5,6-dibromopyridazin-3(2H)-ones (vi) were prepared starting from bromomaleic anhydride (i) via ii (Meier, K.; Ringier, B. H.; Druey, J. *Helv. Chim. Acta* 1954, 37, 523). The substitution reaction of vi with phenolates took place regioselectively resulting in the 5-aryloxy-substituted derivatives (vii). In the Suzuki reactions of vii with various aryl and heteroaryl boronic acid derivatives (Collot, V.; Dallemagne, P.; Bovy, P. R.; Rault S. *Tetrahedron* 1999, 55, 6917) 6-aryl and 6-heteroaryl-substituted pyridazinones (viii-x) were obtained.

General Procedure 3. Synthesis of General Structure xiii-xviii

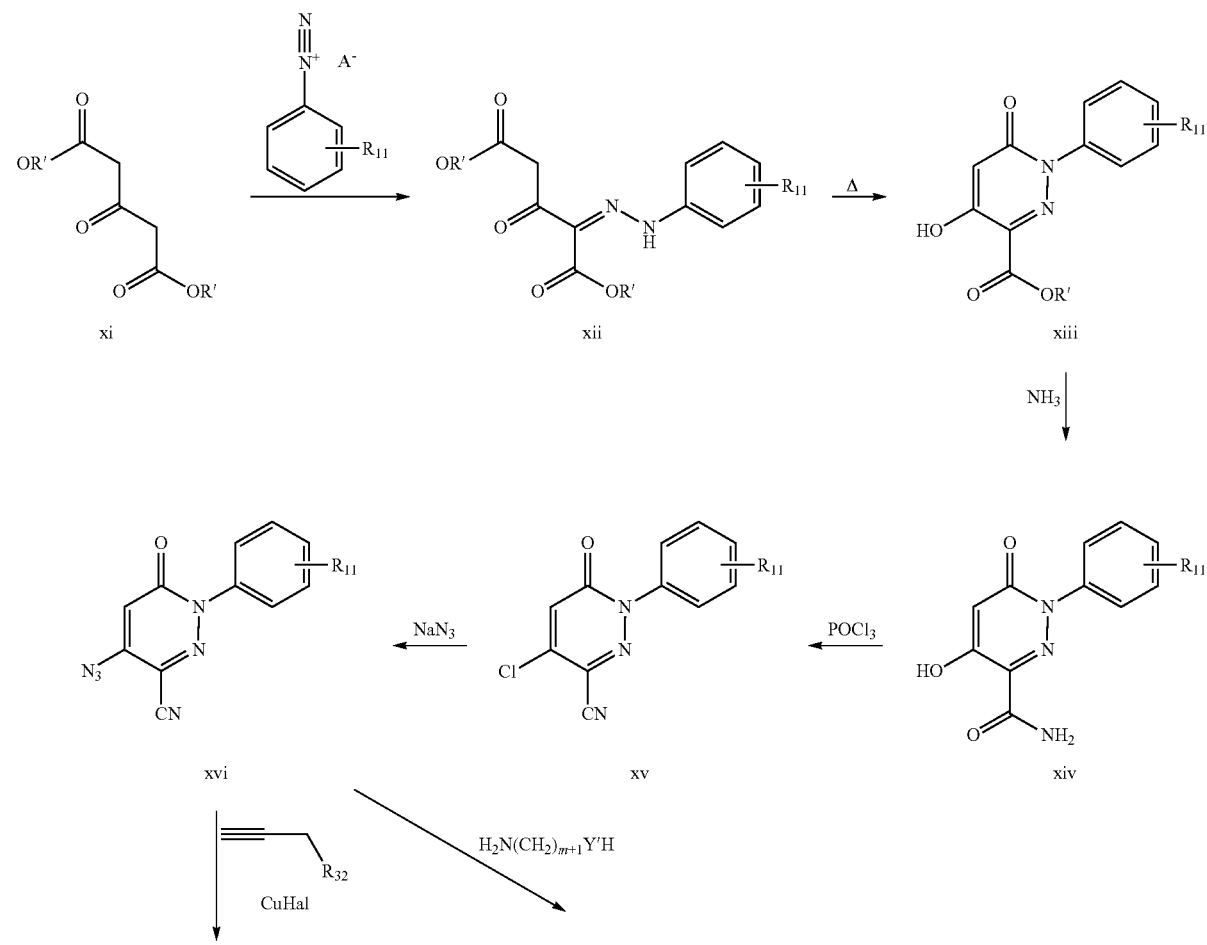

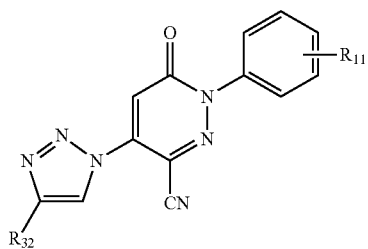

xvii

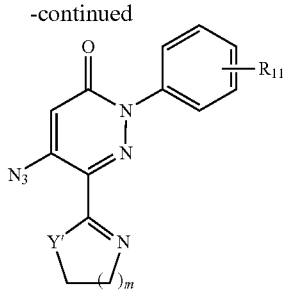

xviii wherein $R_{11}$ is as defined above or H, Y' is NH or $CH_2$, Hal is halogen, m is 1 or 2, and R' is alkyl and A is any anion.

Alkyl 1-aryl-4-hydroxy-6-oxo-1,6-dihydropyridazine-3-carboxylates (xiii) were prepared in two steps via xii starting from dialkyl acetonedicarboxylates (xi) (Schober, B. D.; Megyeri, G.; Kappe, T. J. *Heterocyclic Chem.* 1989, 26, 169). Conventional transformations of the enolic OH of and the carboxylic amide functions of xiv via xv led to azido nitriles xvi. Click reaction of xvi with alkynes resulted in (1H-1,2,3-triazol-1-yl)-substituted pyridazinones (xvii), while the condensations of the cyano group with various 1,2- and 1,3-difunctional compounds led to the pyridazinone derivatives bearing a 1,3-heterocyclic unit in position 6 (xviii).

General Procedure 4. Synthesis of General Structure xx-xxvi

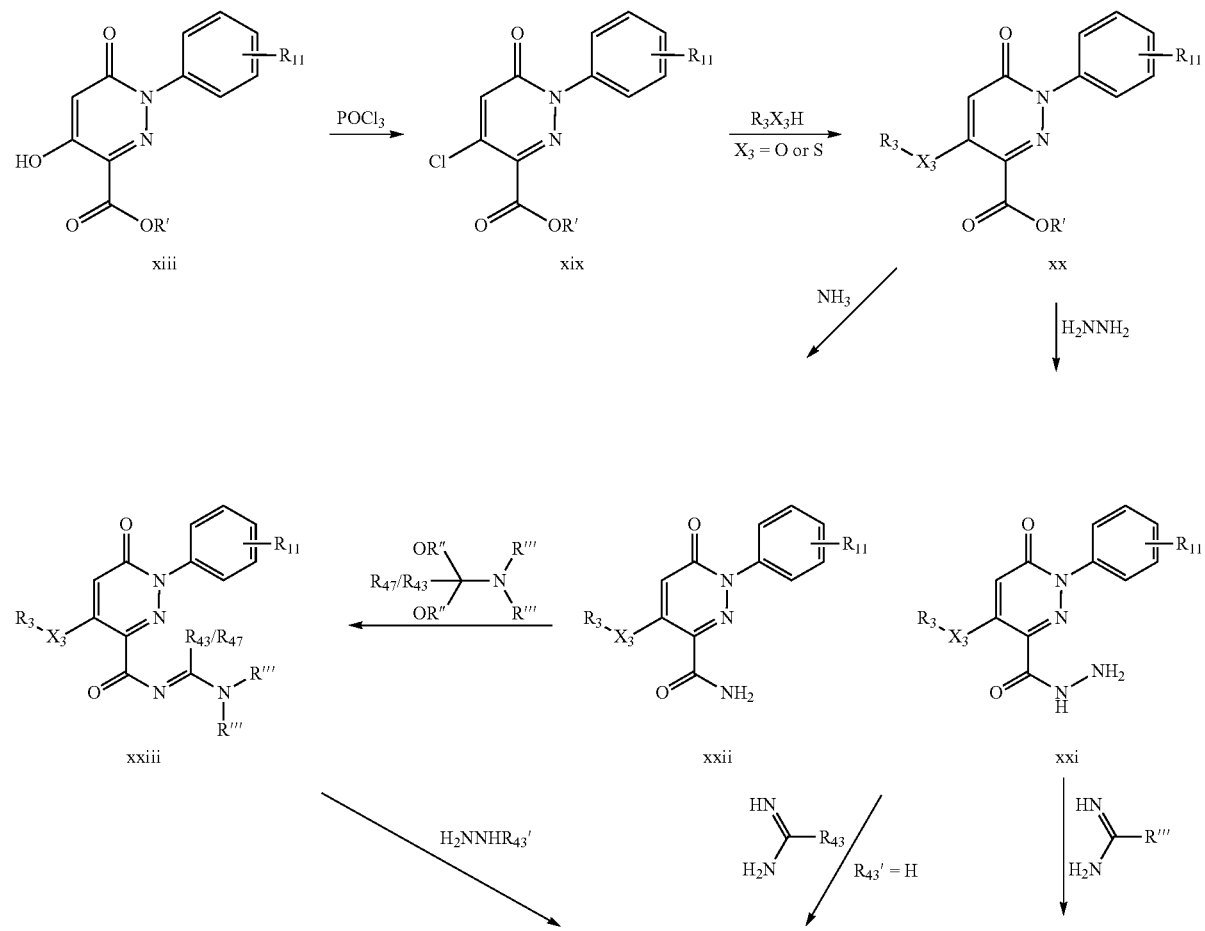

-continued

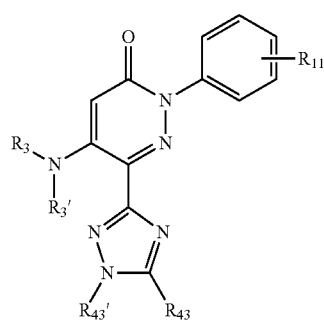

xxv

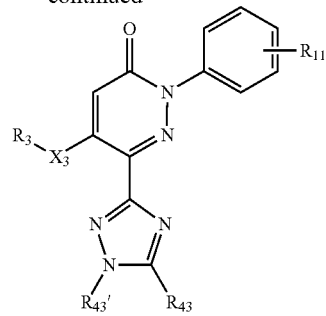

xxiv

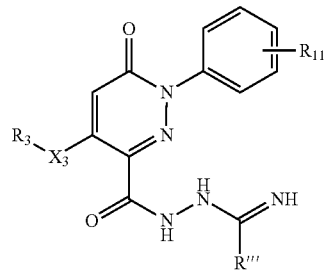

xxvi wherein $R_{11}$ is as defined above or H, $R_{43}=R_{43}'$ are independently as defined above or H, and $R_3$, $X_3$, $R_{47}$, $R_{32}$ and $R_{33}$ are as defined above and each R', R" and R'" is independently alkyl.

Alkyl 1-aryl-4-chloro-6-oxo-1,6-dihydropyridazine-3-carboxylates (xix) were obtained from xiii according to the literature method (Schober, B. D.; Megyeri, G.; Kappe, T. *J. Heterocyclic Chem.* 1990, 27, 471). Substitutions of the 4-chloro substituents were accomplished by using the corresponding phenolates (Dajka-Halász, B. et al. *Tetrahedron* 2004, 60, 2283), or alcohol, thiophenol, thiol, amine or aniline derivatives, respectively (Marlow, A. L. et al. US Patent Application Publication No. US 2005/0256123; Marlow, A. L. et al. PCT International Publication No. WO 2007/044084) to render xx. Carbohydrazides xxi and carboxamides xxii were prepared by using conventional transformations. The reactions of xxii with amide dialkyl acetals furnished acylamidines xxiii which were converted to the corresponding 1,2,4-triazole derivatives xxiv with hydrazines (Lin, Y.; Lang, Jr., S. A.; Lovell, M. F.; Perkinson, N. A. *J. Org. Chem.* 1979, 44, 4160). In the reactions of xxi with amidines, either substituted hydrazide (xxvi) or 1,2,4-triazole derivatives (xxiv) were formed, depending on the reaction conditions (Fukui, K.; Kakeya, N.; Taguchi, M. U.S. Pat. No. 4,578,479). The 5-phenoxy derivatives xxiv ($R^3X$=PhO) underwent to convenient substitution reactions with various amines to furnish compounds xxv.

General Procedure 5. Synthesis of General Structure xxvii-xxix

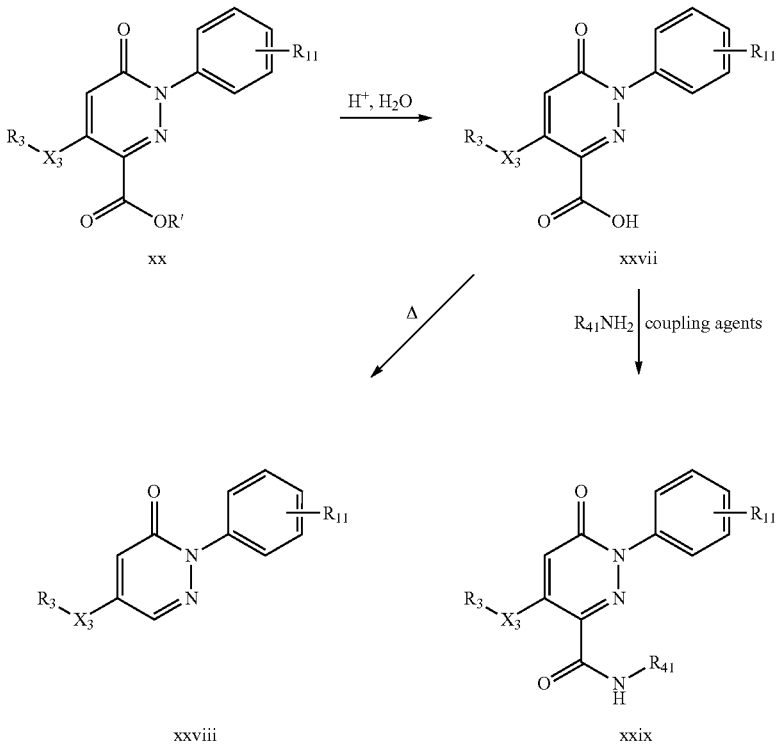

wherein $R_{11}$ is as defined above or H and $R_3$, $X_3$ and $R_{41}$ are as defined above and R' is alkyl.

Hydrolysis of the ester function of xx gave the corresponding carboxylic acid derivatives (xxvii), decarboxylations of which resulted in the 6-unsubstituted pyridazinones (xxviii). Couplings of xxvii with various amines gave carboxamides xxix.

General Procedure 6. Synthesis of General Structure
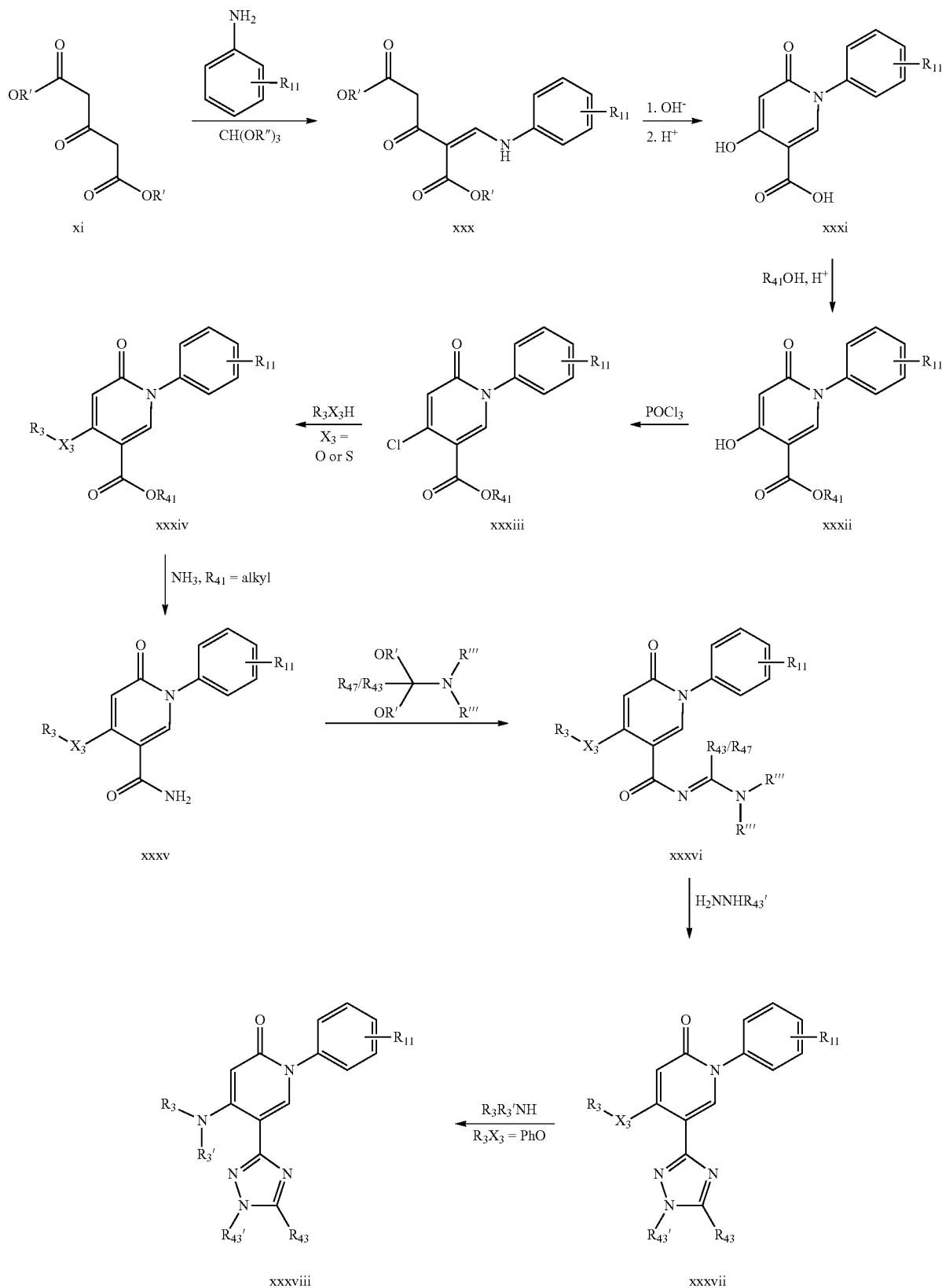

wherein $R_{11}$ and $R_{43}'=R_{43}$ are independently as defined above or H, $X_3$, $R_3$, $R_3'$, $R_{41}$, and $R_{47}$ are as defined above, and each R', R", and R'" is independently alkyl.

Preparation of 1-aryl-4-hydroxy-6-oxo-1,6-dihydropyridine-3-carboxylic acids (xxxi) were accomplished starting from dialkyl 3-oxo-2-[(arylamino)methylene]glutarates (xxx) (Wolfbeis, O. S. *Chem. Ber.* 1981, 114, 3471) by using the reaction conditions applied for the synthesis of the corresponding aza-analogue pyridazinecarboxylic acids (Schober, B. D.; Megyeri, G.; Kappe, T. *J. Heterocyclic Chem.* 1989, 26, 169). Esterifications of xxxi resuited in xxxii. In the further transformations of xxxii towards compounds xxxiii-xxxviii, the procedures of the preparation of the corresponding pyridazine analogues (see Scheme 4) were applied.

Example 1

Synthesis of 5-phenoxy-2-phenyl-6-[(3-trifluoromethyl)phenyl]pyridazin-3(2H)-one (compound 21)

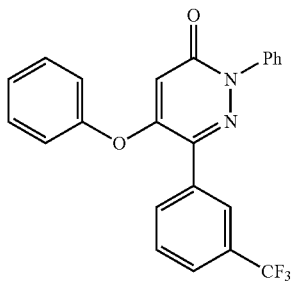 [SMILES: O=c1cc(Oc2ccccc2)c(-c2cccc(C(F)(F)F)c2)nn1-c1ccccc1]

Step A. Preparation of 6-bromo-5-phenoxy-2-phenylpyridazin-3(2H)-one: 5,6-dibromo-2-phenylpyridazin-3(2H)-one (Meier, K.; Ringier, B. H.; Druey, J. *Helv. Chim. Acta* 1954, 37, 523) (6.01 g, 18.2 mmol) and sodium phenolate (3.25 g, 19.1 mmol) were dissolved in dry MeCN (280 mL) and the solution was stirred for 0.5 h at room temperature. After evaporation, the crude product was dissolved in CHCl₃ (400 mL), extracted with saturated NaHCO₃ solution (200 mL). The organic phase was dried (Na₂SO₄) and evaporated. The crude product was purified by column chromatography on silica gel (n-hexane:EtOAc=4:1) resulting in the title compound (5.05 g, 81%).

Step B. Preparation of 5-phenoxy-2-phenyl-6-[(3-trifluoro-methyl)phenyl]pyridazin-3(2H)-one: To a stirred mixture of 6-bromo-5-phenoxy-2-phenylpyridazin-3(2H)-one (207 mg, 0.60 mmol), Pd(PPh₃)₄ (35 mg, 0.03 mmol) and degassed DME (9 mL), 3-(trifluoromethyl)phenylboronic acid (137 mg, 0.72 mmol), and subsequently, a solution of NaHCO₃ (102 mg, 1.2 mmol) in H₂O (2.1 mL) were added. The reaction mixture was heated with vigorous stirring under Ar atmosphere at 80° C. for 12 h. The mixture was then evaporated under reduced pressure and the residue was purified by column chromatography on silica gel (n-hexane:EtOAc=2:1) to yield the desired compound as a white crystalline solid (210 mg, 86%). Mp 146-148° C., ¹H NMR (400 MHz, CDCl₃) δ 6.18 (s, 1H, H-4), 7.15-7.20 (m, 2H), 7.32-7.43 (m, 2H), 7.47-7.53 (m, 4H), 7.60 (t, 1H, J=7.6 Hz), 7.62-7.67 (m, 2H), 7.72 (d, 1H, J=7.5 Hz), 8.11 (d, 1H, J=8.1 Hz), 8.16 (s, 1H) ppm.

Example 2

Synthesis of 6-(1-methyl-1H-pyrazol-4-yl)-5-phenoxy-2-phenylpyridazin-3(2H)-one (compound 17)

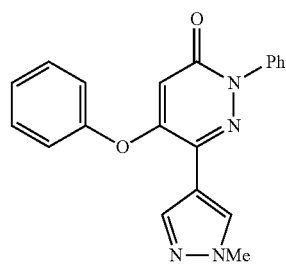 [SMILES: Cn1cc(-c2nn(-c3ccccc3)c(=O)cc2Oc2ccccc2)cn1]

To a stirred mixture of 6-bromo-5-phenoxy-2-phenylpyridazin-3(2H)-one (see Example 2) (207 mg, 0.60 mmol), Pd(PPh₃)₄ (35 mg, 0.03 mmol) and degassed DME (9 mL), 1-methylpyrazole-4-boronic acid pinacol ester (150 mg, 0.72 mmol), and subsequently, a solution of NaHCO₃ (102 mg, 1.2 mmol) in H₂O (2.1 mL) were added. The reaction mixture was heated with vigorous stirring under Ar atmosphere at 80° C. for 12 h. The mixture was then evaporated under reduced pressure and the residue was purified by column chromatography on silica gel (n-hexane:EtOAc=1:1) to yield the desired compound as a white crystalline solid (61 mg, 29%). Mp 195-197° C., ¹H NMR (400 MHz, CDCl₃) δ 3.97 (s, 3H, CH₃), 6.10 (s, 1H, H-4), 7.20 (d, 2H, J=7.6 Hz, C₆H₅), 7.33-7.55 (m, 6H, 2×C₆H₅), 7.64 (d, 2H, J=7.6 Hz, C₆H₅), 8.03 (s, 1H, NCH), 8.11 (s, 1H, NCH) ppm.

Example 3

Synthesis of 6-oxo-1-phenyl-4-(4-propyl-1H-1,2,3-triazol-1-yl)-1,6-dihydropyridazine-3-carbonitrile (compound 32)

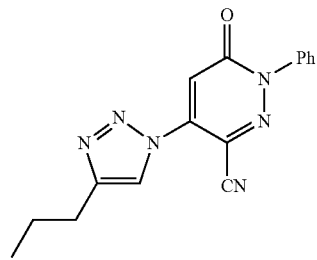 [SMILES: CCCc1cn(-c2cc(=O)n(-c3ccccc3)nc2C#N)nn1]

Step A. Preparation of 4-hydroxy-6-oxo-1-phenyl-1,6-dihydropyridazine-3-carboxamide: Methyl 4-hydroxy-6-oxo-1-phenyl-1,6-dihydropyridazine-3-carboxylate (Schober, B. D.; Megyeri, G.; Kappe, T. *J. Heterocyclic Chem.* 1989, 26, 169) (2.00 g, 8.1 mmol) was dissolved in 25% methanolic NH₃ solution (25 mL) and the mixture was kept at room temperature for 3 days. Then the formed solid was filtered off, washed with Et₂O and dried giving a white-yellow solid (1.60 g, 85%).

Step B. Preparation of 4-chloro-6-oxo-1-phenyl-1,6-dihydropyridazine-3-carbonitrile: To 4-hydroxy-6-oxo-1-phenyl-1,6-dihydropyridazine-3-carboxamide (500 mg, 2.16 mmol) POCl₃ was added (5 mL) and the mixture was stirred at 80° C. for 3 h. Then the mixture was poured into ice-cold water (50 ml) and extracted with EtOAc (2×15 mL). The organic phases were dried (Na₂SO₄) and evaporated. The residue was purified by column chromatography on silica gel (n-hexane:EtOAc=3:1) giving a white solid (190 mg, 38%).

Step C. Preparation of 4-azido-6-oxo-1-phenyl-1,6-dihydropyridazine-3-carbonitrile: To a solution of 4-chloro-6-oxo-1-phenyl-1,6-dihydropyridazine-3-carbonitrile (120 mg, 0.52 mmol) in DMF (5 mL), NaN₃ (101 mg, 1.55 mmol) was added and the mixture was stirred at 20° C. for 2 h. Then the mixture was poured into H₂O (25 mL) and the formed precipitate was collected by filtration giving a white solid (101 mg, 82%).

Step D. Preparation of 6-oxo-1-phenyl-4-(4-propyl-1H-1,2,3-triazol-1-yl)-1,6-dihydropyridazine-3-carbonitrile: To a solution of 4-azido-6-oxo-1-phenyl-1,6-dihydropyridazine-3-carbonitrile (300 mg, 1.26 mmol) in MeCN (5 mL) 1-pentyne (86 mg, 1.26 mmol) and CuI (50 mg) were added and then the mixture was stirred under reflux. After 4 h the mixture was evaporated in vacuo and purified by column chromatography on silica gel (n-hexane:EtOAc=2:1) giving a yellowish white solid (312 mg, 81%). Mp 192-195° C., ¹H NMR (400 MHz, DMSO-d₆) δ 0.97 (t, 3H, J=7.2 Hz, CH₃), 1.67-1.76 (m, 2H, CH₂), 2.70-2.78 (t, 3H, J=7.2 Hz, CH₂), 7.52-7.64 (m, 5H, C₆H₅), 7.69 (s, 1H, H-5), 8.67 (s, 1H, CH-triazole) ppm.

Example 4

5-Azido-6-(4,5-dihydro-1H-imidazol-2-yl)-2-phenylpyridazin-3(2H)-one (compound 47)

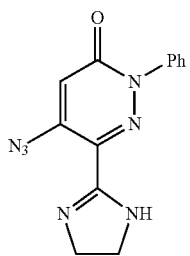 [SMILES: [N-]=[N+]=Nc1cc(=O)n(-c2ccccc2)nc1C1=NCCN1]

To a solution of 4-azido-6-oxo-1-phenyl-1,6-dihydropyridazine-3-carbonitrile (see Example 4) (200 mg, 0.84 mmoles) in toluene (10 mL) ethylenediamine (50 mg, 0.84 mmol) and pTsOH (145 mg, 0.84 mmol) were added. The mixture was stirred at ambient temperature for 14 h and then was evaporated in vacuo. The residue was purified by column chromatography on silica gel (n-hexane:EtOAc=1:4) giving a yellowish white solid (78 mg, 33%). Mp 238-240° C., ¹H NMR (400 MHz, DMSO-d₆) δ 3.28-3.36 (m, 2H, CH₂), 3.83-3.95 (m, 2H, CH₂), 5.76 (s, 1H, CH), 6.89 (br s, 1H, N—H), 7.38-7.43 (m, 1H, C₆H₅), 7.48-7.53 (m, 2H, C₆H₅), 7.61-7.67 (m, 2H, C₆H₅) ppm.

Example 5

Synthesis of N,N-dimethyl-N'-[(6-oxo-4-phenoxy-1-phenyl-1,6-dihydropyridazin-3-yl)carbonyl]formamidine (compound 23)

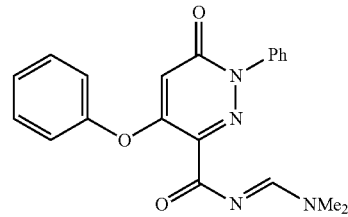 [SMILES: CN(C)/C=N/C(=O)c1nn(-c2ccccc2)c(=O)cc1Oc1ccccc1]

Step A. Preparation of methyl 6-oxo-4-phenoxy-1-phenyl-1,6-dihydropyridazine-3-carboxylate: A mixture of methyl 4-chloro-6-oxo-1-phenyl-1,6-dihydropyridazine-3-carboxylate (Schober, B. D.; Megyeri, G.; Kappe, T. *J. Heterocyclic Chem.* 1990, 27, 471) (8.06 g, 30.4 mmol), sodium phenolate trihydrate (5.18 g, 30.4 mmol) and DMF (150 mL) was stirred at room temperature for 20 h. The solvent was evaporated in vacuo and the residue was partitioned between water (200 mL) and EtOAc (200 mL). The organic phase was separated and the aqueous phase was extracted with EtOAc (2×100 mL). The combined organic extracts were washed successively with cold 3% NaOH (2×100 mL) and with cold water (2×100 mL) and then were dried (Na₂SO₄) and evaporated in vacuo. Et₂O (50 mL) was added to the solid residue and the beige crystalline product (7.05 g, 72%) was filtered off and washed with Et₂O (50 mL).

Step B. Preparation of 6-oxo-4-phenoxy-1-phenyl-1,6-dihydropyridazine-3-carboxamide: To a solution of methyl 6-oxo-4-phenoxy-1-phenyl-1,6-dihydropyridazine-3-carboxylate (10.00 g, 31 mmol) in MeOH (100 mL), cold 25% methanolic ammonia solution (200 mL) was added. The mixture was stirred at room temperature for 45 min and then the ammonia was removed at room temperature in vacuo. The solvent was then evaporated at 40-50° C. in vacuo and the solid residue was dissolved in EtOAc (50 mL). A precipitation of a beige crystalline product was occurred when Et₂O (150 mL) was added to the solution. The crystals (7.25 g, 76%) were filtered off and washed with Et₂O (30 mL).

Step C. Preparation of N,N-dimethyl-N'-[(6-oxo-4-phenoxy-1-phenyl-1,6-dihydropyridazin-3-yl)carbonyl]formamidine: A mixture of 6-oxo-4-phenoxy-1-phenyl-1,6-dihydropyridazine-3-carboxamide (1.45 g, 4.7 mmol) and N,N-dimethylformamide dimethyl acetal (2.50 g, 21 mmol) was stirred at 90° C. for 15 min. Then the mixture was cooled down to room temperature, Et₂O (30 mL) was added and the crystalline product was filtered and washed with Et₂O (2×20 mL) to yield beige crystals (1.44 g, 84%). Mp 175-176° C., ¹H NMR (400 MHz, CDCl₃) δ 3.22 (s, 3H, NCH₃), 3.24 (s, 3H, NCH₃), 6.13 (s, 1H, H-5), 7.18-7.24 (m, 2H, C₆H₅), 7.29-7.36 (m, 1H, C₆H₅), 7.37-7.43 (m, 1H, C₆H₅), 7.45-7.52 (m, 4H, C₆H₅), 7.60-7.66 (m, 2H, C₆H₅), 8.71 (s, 1H, N=CH) ppm.

Example 6

Synthesis of 5-phenoxy-2-phenyl-6-(5-methyl-1H-1,2,4-triazol-3-yl)-3(2H)-pyridazinone (compound 51)

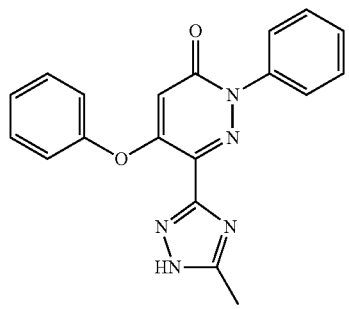 [SMILES: Cc1nc(-c2nn(-c3ccccc3)c(=O)cc2Oc2ccccc2)n[nH]1]

Step A. Preparation of N,N-dimethyl-N'-[(6-oxo-4-phenoxy-1-phenyl-1,6-dihydropyridazin-3-yl)carbonyl]acetamidine: A mixture of 6-oxo-4-phenoxy-1-phenyl-1,6-dihydropyridazine-3-carboxamide (see Example 6) (0.60 g, 1.95 mmol), N,N-dimethylacetamide dimethyl acetal (1.80 g, 13.5 mmol) and toluene (5 mL) was stirred at 50° C. for 45 min. Then the mixture was cooled down to room temperature, Et$_2$O (30 mL) was added and the crystalline product was filtered and washed with Et$_2$O (2×20 mL) to yield beige crystals (0.58 g, 79%).

Step B. Preparation of 5-Phenoxy-2-phenyl-6-(5-methyl-1H-1,2,4-triazol-3-yl)-3(2H)-pyridazinone: A mixture of hydrazine hydrate (82 mg, 1.6 mmol), glacial acetic acid (2.3 g) and N,N-dimethyl-N'-[(6-oxo-4-phenoxy-1-phenyl-1,6-dihydropyridazin-3-yl)carbonyl]acetamidine (557 mg, 1.5 mmol) was stirred at 90° C. for 1.5 h. After the mixture was cooled down to room temperature, Et$_2$O (20 mL) was added the precipitated solid was filtered off and washed with Et$_2$O (2×20 mL). The crude product was recrystallized from a mixture of EtOAc and n-hexane to yield the title compound as beige crystals (395 mg, 77%). Mp 245-247° C., $^1$H NMR (400 MHz, DMSO-d$_6$) δ 2.41 (s, 3H, CH$_3$), 5.88 (s, 1H, H-5), 7.26-7.60 (m, 10H, 2×C$_6$H$_5$) ppm.

Example 7

Synthesis of 5-benzylamino-2-phenyl-6-(1H-1,2,4-triazol-3-yl)-3(2H)-pyridazinone (compound 42)

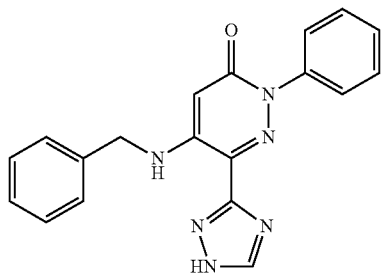 [SMILES: O=c1cc(NCc2ccccc2)c(-c2nc[nH]n2)nn1-c1ccccc1]

Step A. Preparation of 5-phenoxy-2-phenyl-6-(1H-1,2,4-triazol-3-yl)-3(2H)-pyridazinone: A mixture of hydrazine hydrate (246 mg, 4.9 mmol), AcOH (6.5 mL) and N,N-dimethyl-N'-[(6-oxo-4-phenoxy-1-phenyl-1,6-dihydropyridazin-3-yl)carbonyl]formamidine (see Example 6) (1628 mg, 4.5 mmol) was stirred at 90° C. for 1.5 h. After the mixture was cooled down to room temperature, Et$_2$O (30 mL) was added and the precipitated solid was filtered off and washed with Et$_2$O (2×25 mL) to afford the desired compound as a beige crystalline product (1240 mg, 83%).

Step B. 5-Benzylamino-2-phenyl-6-(1H-1,2,4-triazol-3-yl)-3(2H)-pyridazinone: A mixture of 5-phenoxy-2-phenyl-6-(1H-1,2,4-triazol-3-yl)-3(2H)-pyridazinone (100 mg, 0.3 mmol) and benzylamine (200 mg, 1.9 mmol) was stirred at 200° C. for 30 min under N$_2$ atmosphere. The oily mixture was cooled down to room temperature, and was crystallized on treatment with Et$_2$O (20 mL). The solid product was filtered off, washed with Et$_2$O (2×20 ml) and dissolved in EtOAc (100 mL). The solution was washed successively with 5% aqueous AcOH (3×30 mL) and water (3×30 mL). The organic phase was dried (Na$_2$SO$_4$) and evaporated. The crude product was recrystallized from a mixture of iPr$_2$O and EtOAc to yield the title compound as a white crystalline substance (78 mg, 75%). Mp 192-193° C., $^1$H NMR (400 MHz, DMSO-d$_6$) δ 4.54 (d, 2H, J=5.6 Hz, CH$_2$), 5.80 (s, 1H, H-5), 7.28-7.72 (m, 10H, 2×C$_6$H$_5$), 8.24 (br s, 1H) 8.86 (br s, 1H), 14.70 (br s, 1H) ppm.

Example 8

Synthesis of 5-isopropylamino-2-phenyl-6-(1H-1,2,4-triazol-3-yl)-3(2H)-pyridazinone (compound 29)

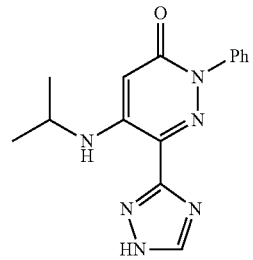

5-Phenoxy-2-phenyl-6-(1H-1,2,4-triazol-3-yl)-3(2H)-pyridazinone (see Example 8) (140 mg, 0.42 mmol), isopropylamine (355 mg, 6 mmol) and EtOH (4 mL) were placed in a 10 mL pressurized reaction vial. The mixture was heated by microwave irradiation at 150° C. for 60 min. The solvent was then evaporated off and the residue was crystallized on treatment with Et$_2$O (15 mL). The crude product was filtered off and recrystallized from a 3:2 mixture of EtOH and Et$_2$O (10 mL) to yield a white crystalline substance (94 mg, 76%). Mp 203-205° C., $^1$H NMR (400 MHz, DMSO-d$_6$) δ 1.27 (d, 6H, J=6.3 Hz, CH$_3$), 3.71-3.77 (m, 1H, CH(CH$_3$)$_2$), 5.83 (s, 1H, H-4), 7.37-7.66 (m, 5H, C$_6$H$_5$), 8.32 (br s, 1H), 8.46 (br s, 1H) ppm.

Example 9

Synthesis of 2-(4-chlorophenyl)-5-[(4-methoxyphenyl)amino]-6-(1H-1,2,4-triazol-3-yl)-3(2H)-pyridazinone (compound 57)

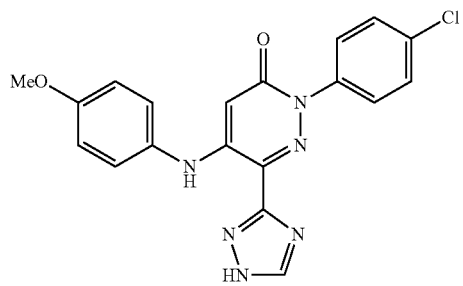

Step A. Preparation of methyl 1-(4-chlorophenyl)-4-[(4-methoxyphenyl)amino]-6-oxo-1,6-dihydropyridazine-3-carboxylate: A mixture of methyl 4-chloro-1-(4-chlorophenyl)-6-oxo-1,6-dihydropyridazine-3-carboxylate (Schober, B. D.; Megyeri, G.; Kappe, T. *J. Heterocyclic Chem.* 1990, 27, 471) (20.00 g, 0.067 mol), p-anisidine (16.66 g, 0.135 mol) and EtOH (200 mL) was refluxed for 16 h and then cooled to room temperature. The precipitate was filtered off, washed with cold EtOH (50 mL). The crude product was recrystallized from EtOH to yield beige crystals (23.5 g, 91%).

Step B. Preparation of 1-(4-chlorophenyl)-4-[(4-methoxyphenyl)amino]-6-oxo-1,6-dihydropyridazine-3-carbohydrazide: A mixture of methyl 1-(4-chlorophenyl)-4-[(4-methoxyphenyl)amino]-6-oxo-1,6-dihydropyridazine-3-carboxylate (20.0 g, 0.052 mol), hydrazine hydrate (5.40 g, 0.108 mol) and EtOH (200 mL) was refluxed for 16 h and then cooled to room temperature. The precipitate was filtered off, washed with cold EtOH (30 mL) and dried to yield beige crystals (18.2 g, 91%).

Step C. Preparation of 2-(4-chlorophenyl)-5-[(4-methoxyphenyl)amino]-6-(1H-1,2,4-triazol-3-yl)-3(2H)-pyridazinone: A mixture of 1-(4-chlorophenyl)-4-[(4-methoxyphenyl)amino]-6-oxo-1,6-dihydropyridazine-3-carbohydroazide (10.0 g, 0.026 mol), formamidine acetate (3.64 g, 0.035 mol) and n-PrOH (150 mL) was refluxed 1 h. The solvent was then evaporated in vacuo and the residue was purified by column chromatography on neutral $Al_2C_3$, using first EtOAc then a mixture of $CHCl_3$ and MeOH (4:1) as eluent. The requested fractions were evaporated and the residue was recrystallized from a mixture of THF and MeOH to yield beige crystals (5.9 g, 58%). Mp 251-252° C., $^1$H-NMR (DMSO-$d_6$) δ 3.80 (s, 1H, H-Me), 5.87 (s, 1H, H-4), 6.95-7.84 (m, 8H, 2×$C_6H_4$), 8.49 (br s, 1H, Ar—NH), 9.99 (br s, 1H, 1,2,4-triazole-H), 14.80 (br s, 1H, 1,2,4-triazole) ppm.

Example 10

Synthesis of 2-phenyl-5-phenylsulfanyl-6-(1H-1,2,4-triazol-3-yl)-3(2H)-pyridazinone (compound 16)

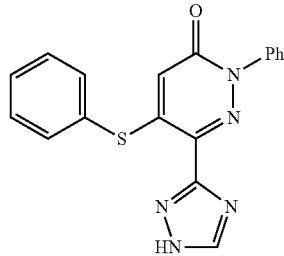

Step A. Preparation of methyl 6-oxo-1-phenyl-4-phenylsulfanyl-1,6-dihydropyridazine-3-carboxylate: To a solution of 4-chloro-6-oxo-1-phenyl-1,6-dihydropyridazine-3-carboxylate (Schober, B. D.; Megyeri, G.; Kappe, T. *J. Heterocyclic Chem.* 1990, 27, 471) (1.32 g, 5 mmol) in dry DMF (15 mL), with thiophenol (0.55 g, 5 mmol) and $K_2CO_3$ (2.07 g, 15 mmol) were added. The mixture was stirred for 1 h and then was poured into ice-cold water (40 mL). The precipitated crude product was filtered off and recrystallized from a mixture of EtOAc and MeOH to afford a pale-yellow crystalline substance (1.31 g, 78%).

Step B. Preparation of 6-oxo-1-phenyl-4-phenylsulfanyl-1,6-dihydropyridazine-3-carboxamide: In a 25-mL pressurized reaction vial, a mixture of methyl 6-oxo-1-phenyl-4-phenylsulfanyl-1,6-dihydropyridazine-3-carboxylate (338 mg, 1 mmol) and 25% methanolic ammonia solution (10 mL) was stirred at room temperature for 4 h. The solvent was evaporated off and the solid residue was recrystallized from EtOH to yield a pale-yellow crystalline substance (249 mg, 77%).

Step C. Preparation of N,N-dimethyl-N'-[(6-oxo-1-phenyl-4-phenylsulfanyl-1,6-dihydropyridazin-3-yl)carbonyl]formamidine: A mixture of 6-oxo-1-phenyl-4-phenylsulfanyl-1,6-dihydropyridazine-3-carboxamide (193 mg, 0.6 mmol) and N,N-dimethylformamide dimethyl acetal (1 mL) was stirred at 120° C. for 1 h and then evaporated in vacuo. The residue was crystallized on treatment with $Et_2O$ (10 mL) to yield the desired product as a white crystalline substance (196 mg, 88%).

Step D. Preparation of 2-phenyl-5-phenylsulfanyl-6-(1H-1,2,4-triazol-3-yl)-3(2H)-pyridazinone: To a solution of hydrazine hydrate (30 mg, 0.6 mmol) in AcOH (1 mL), N,N-dimethyl-N'-[(6-oxo-1-phenyl-4-phenylsulfanyl-1,6-dihydropyridazin-3-yl)carbonyl]formamidine (189 mg, 0.5 mmol) was added. The reaction mixture was stirred at 90° C. for 1 h, and the evaporated in vacuo. The oily residue was crystallized on treatment with $Et_2O$ (10 mL). The solid was recrystallized from EtOH to afford a white crystalline product (120 mg, 70%). Mp 245-250° C., $^1$H NMR (400 MHz, DMSO-$d_6$) δ 5.92 (s, 1H, H-4), 7.43-7.70 (m, 10H, 2×$C_6H_5$), 8.78 (s, 1H, 1,2,4-triazole) ppm.

Example 11

Synthesis of $N^2$-iminomethyl-6-oxo-4-phenylsulfanyl-1-phenyl-1,6-dihydropyridazin-3-carbohydrazide (compound 8)

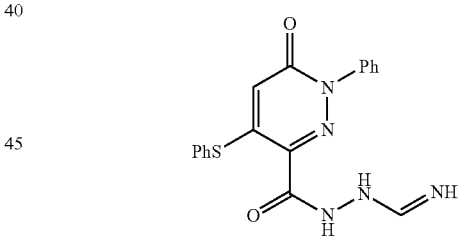

Step A. Preparation of 6-oxo-4-phenylsulfanyl-1-phenyl-1,6-dihydropyridazin-3-carbohydrazide: A mixture of methyl 6-oxo-1-phenyl-4-phenylsulfanyl-1,6-dihydropyridazine-3-carboxylate (see Example 11) (0.51 g, 1.5 mmol), EtOH (20 mL) and hydrazine hydrate (0.15 g, 3 mmol) was refluxed for 6 h. The product precipitated on cooling as a white crystalline substance (0.39 g, 73%).

Step B. Preparation of $N^2$-iminomethyl-6-oxo-4-phenylsulfanyl-1-phenyl-1,6-dihydropyridazin-3-carbohydrazide: A mixture of formamidine acetate (156 mg, 1.5 mmol), NaOEt (102 mg, 1.5 mmol), EtOH (20 mL) and 6-oxo-4-phenylsulfanyl-1-phenyl-1,6-dihydropyridazin-3-carbohydrazide (310 mg, 1 mmol) was stirred at room temperature for 10 h. The title compound was precipitated as a white crystalline substance (277 mg, 76%), which was filtered off and washed with cold EtOH. Mp 236-238° C., $^1$H NMR (400

MHz, DMSO-$d_6$) δ 5.84 (s, 1H, H-6), 6.15 (s, 1H, NH), 7.05 (s, 1H, NH), 7.41-7.78 (m, 11H, 2×$C_6H_5$, NH) ppm.

Example 12

Synthesis of N-[2-(dimethylamino)ethyl]-6-oxo-4-phenoxy-1-phenyl-1,6-dihydropyridazin-3-carboxamide hydrochloride (compound 4)

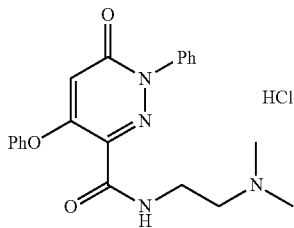 [SMILES: CN(C)CCNC(=O)c1nn(-c2ccccc2)c(=O)cc1Oc1ccccc1 ; Cl]

The mixture of 6-oxo-4-phenoxy-1-phenyl-1,6-dihydropyridazine-3-carboxylic acid (see Example 14) (100 mg, 0.65 mmol), 1-hydroxybenzotriazole hydrate (90 mg, 0.66 mmol) and 2-dimethylaminoethylamine (45 mg, 0.71 mmol) in DMF (10 mL) was stirred at 0° C. for 30 min and then N,N'-diisopropylcarbodiimide (90 mg, 0.71 mmol) of was added. The mixture was left to warm up to the room temperature and stirred for additional 20 h. The solvent was removed under reduced pressure and the crude product was purified by column chromatography on silica gel ($CHCl_3$: MeOH=9:1). The collected fractions were concentrated to dryness under reduced pressure. The residue was dissolved in EtOH (5 mL) and the solution was treated with 22% ethanolic HCl (1 mL) and $Et_2O$ (15 mL) to yield the desired product as white crystalline substance (226 mg, 84%). Mp 138-141° C., $^1$H NMR (400 MHz, $D_2O$) δ 2.99 (s, 6H, $NCH_3$), 3.44 (t, 2H, J=5.2 Hz, $CH_2$), 3.86 (t, 2H, J=5.8 Hz, $CH_2$), 6.35 (s, 1H, H-4), 7.35 (d, 2H, J=8.0 Hz, $C_6H_5$), 7.48-7.72 (m, 8H, 2×$C_6H_5$) ppm.

Example 13

Synthesis of 4-phenoxy-5-(1H-1,2,4-triazol-3-yl)-1-phenylpyridin-2(1H)-one (compound 34)

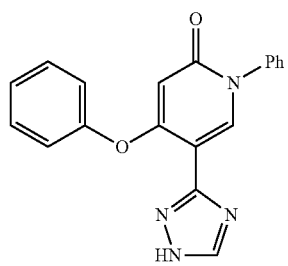

Step A. Preparation of 4-hydroxy-6-oxo-1-phenyl-1,6-dihydropyridine-3-carboxylic acid: Dimethyl 3-oxo-2-[(phenylamino)methylene]glutarate (Wolfbeis, O. S. Chem. Ber. 1981, 114, 3471) (10.0 g, 36 mmol) was dissolved in 2 M NaOH (180 mL). The solution was filtered and acidified by addition of conc. hydrochloric acid under ice-cooling and with vigorous stirring. The product was filtered off and washed with cold water (2×100 mL) to yield the title compound as a beige solid (8.10 g, 97%).

Step B. Preparation of methyl 4-hydroxy-6-oxo-1-phenyl-1,6-dihydropyridine-3-carboxylate: A mixture of 4-hydroxy-6-oxo-1-phenyl-1,6-dihydropyridine-3-carboxylic acid (8.00 g, 34.6 mmol), MeOH (300 mL) and conc. $H_2SO_4$ (3 mL) was refluxed for 20 h. The solution was evaporated in vacuo and the residue was dissolved in EtOAc (200 mL) and ice-cold water (50 mL). The organic phase was separated, washed with ice-cold water (2×50 mL), dried ($Na_2SO_4$) and evaporated. The crude product was recrystallized from MeOH to yield the title compound as a beige crystalline substance (4.10 g, 48%).

Step C. Preparation of methyl 4-chloro-6-oxo-1-phenyl-1,6-dihydropyridine-3-carboxylate: A mixture of methyl 4-hydroxy-6-oxo-1-phenyl-1,6-dihydropyridine-3-carboxylate (4.00 g, 16.3 mmol) and $POCl_3$ (12 mL) was refluxed for 3 h. The solution was evaporated in vacuo and the residue was dissolved in EtOAc (200 mL) and ice-cold water (50 mL). The organic phase was separated, washed with ice-cold water (2×50 mL), dried ($Na_2SO_4$) and evaporated. The crude product was purified by column chromatography on silica gel (EtOAc) to afford the desired product as a beige solid (1.18 g, 27%).

Step D. Preparation of methyl 6-oxo-4-phenoxy-1-phenyl-1,6-dihydropyridine-3-carboxylate: A mixture of methyl 4-chloro-6-oxo-1-phenyl-1,6-dihydropyridine-3-carboxylate (6.10 g, 23.1 mmol), sodium phenolate trihydrate (5.12 g, 30.1 mmol) and DMF (50 mL) was stirred at 120° C. for 4 h. When the mixture was cooled down to room temperature water (250 mL) was added and the separated beige solid (3.5 g, 47%) was filtered off and washed with cold water (3×50 mL).

Step E. Preparation of 6-oxo-4-phenoxy-1-phenyl-1,6-dihydropyridine-3-carboxamide: To a solution of methyl 6-oxo-4-phenoxy-1-phenyl-1,6-dihydropyridine-3-carboxylate (4.00 g, 12.4 mmol) in MeOH (40 mL), 25% methanolic ammonia solution (100 mL) was added and the mixture was left to stand at room temperature for 15 h. The solvent was then evaporated and the solid residue was purified by column chromatography on silica gel (EtOAc) to afford the title compound as a pale beige solid (3.40 g, 89%).

Step F. Preparation of N,N-dimethyl-N'-[(6-oxo-4-phenoxy-1-phenyl-1,6-dihydropyridin-3-yl)carbonyl]formamidine: A mixture of 6-oxo-4-phenoxy-1-phenyl-1,6-dihydropyridine-3-carboxamide (195 mg, 0.64 mmol) and N,N-dimethylformamide dimethyl acetal (270 mg, 2.3 mmol) was stirred at 120° C. for 90 min. Then the mixture was cooled down to room temperature and evaporated in vacuo. The residue was crystallized on treatment with $Et_2O$ (15 mL). The solid product was filtered and washed with $Et_2O$ (2×10 mL) to yield the title compound as beige crystals (190 mg, 82%).

Step G. Preparation of 4-phenoxy-5-(1H-1,2,4-triazol-3-yl)-1-phenylpyridin-2(1H)-one: A mixture of hydrazine hydrate (29 mg, 0.58 mmol), glacial acetic acid (1.05 g) and N,N-dimethyl-N'-[(6-oxo-4-phenoxy-1-phenyl-1,6-dihydropyridin-3-yl)carbonyl]formamidine (190 mg, 0.53 mmol) was stirred at 90° C. for 1.5 h. Then the mixture was cooled down to room temperature and evaporated in vacuo. The residue was crystallized on treatment with $Et_2O$ (15 mL). The solid product was filtered off and purified by column chromatography on silica gel (EtOAc) to afford the title compound as a white solid (75 mg, 43%). Mp 275-276° C., $^1$H NMR (400 MHz, DMSO-$d_6$) δ 5.41 (s, 1H, H-3), 7.28-7.60 (m, 10H, 2×$C_6H_5$), 8.20 (s, 1H, N—CH), 8.23 (s, 1H, N—CH) ppm.

Example 14

Synthesis of 4-(4-methylpiperazin-1-yl)-5-(1H-1,2,4-triazol-3-yl)-1-phenylpyridin-2(1H)-one hydrogenfumarate (compound 35)

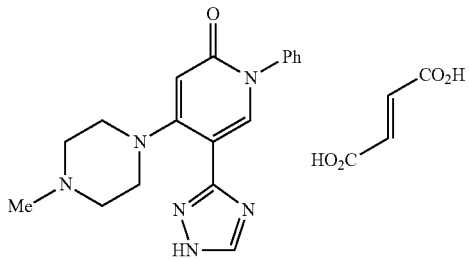 [SMILES: CN1CCN(c2cc(=O)n(-c3ccccc3)cc2-c2nc[nH]n2)CC1 ; O=C(O)/C=C/C(=O)O]

A mixture of 4-phenoxy-5-(1H-1,2,4-triazol-3-yl)-1-phenylpyridin-2(1H)-one (see example 16) (100 mg, 0.6 mmol) and N-methylpiperazine (300 mg, 3 mmol) was heated by microwave irradiation in a 10 mL pressurized reaction vial at 150° C. for 60 min. The mixture was cooled down to room temperature, and was crystallized on treatment with $Et_2O$ (5 mL). The crystals were filtered off, washed with $Et_2O$ (2×5 mL) and dissolved in EtOH (10 ml). An equivalent amount of fumaric acid and $Et_2O$ (25 mL) were added to the solution. The separated crystalline product (55 mg, 40%) was filtered off and washed with $Et_2O$ (2×5 mL). Mp 236-239° C., $^1$H NMR (400 MHz, $D_2O$) δ 3.01 (s, 3H, $CH_3$), 3.17-3.33 (m, 4H, 2×$NCH_2$), 3.44-3.64 (m, 4H, 2×$NCH_2$), 6.26 (s, 1H, H-3), 6.79 (s, 2H, CH=CH), 7.44-7.53 (m, 2H, $C_6H_5$), 7.59-7.71 (m, 3H, $C_6H_5$), 7.97 (s, 1H, N—CH), 8.57 (s, 1H, N—CH) ppm.

The invention claimed is:

1. A pyridazinone compound of general formula (I'), or pharmaceutically acceptable salt, hydrate, or solvate thereof,

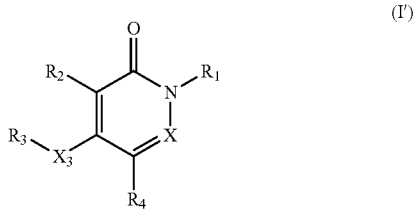

(I')

wherein
X is N;
$R_1$ is phenyl, optionally substituted with $R_{11}$,
wherein $R_{11}$ is selected from the group consisting of halogen, halo-$C_{1-3}$-alkyl, and $C_{1-6}$-alkoxy;
$R_2$ is H or triazolyl;
(i) $X_3$ is O or S, and
$R_3$ is selected from the group consisting of $C_{2-6}$-alkenyl, and phenyl, said phenyl being optionally substituted one or more times with $R_{31}$, each $R_{31}$ is independently selected from the group consisting of halogen, halo-$C_{1-3}$-alkyl and $C_{1-6}$-alkoxy; or (ii) $X_3$ is $NR_3'$, and
$R_3$ and $R_3'$ together with the nitrogen, to which they are attached, form a 5 or 6 membered saturated heterocyclic ring, —$N_3$, or triazole, said triazole being optionally substituted with $R_{32}$, wherein $R_{32}$ is selected from the group consisting of phenyl, $C_{1-6}$-alkyl, and —$CO_2(C_{1-3}$-alkyl); or
$R_3'$ is H or $C_{1-3}$-alkyl, and
$R_3$ is selected from the group consisting of H; $C_{1-6}$-alkyl; $C_{2-6}$-alkenyl; $C_{2-6}$-alkynyl; $C_{3-6}$-cycloalkyl-$C_{1-6}$-alkyl; $C_{3-6}$-cycloalkyl; cyano-$C_{1-6}$-alkyl; amino-$C_{1-6}$-alkyl; benzyl; pyridyl saturated 5 or 6 membered heterocyclic ring having 1 to 2 heteroatoms selected from N, O, and S, and wherein said N is optionally substituted with $C_{1-6}$-alkyl; $R_{33}R_{33}'N$—$C_{1-6}$-alkylenyl; and phenyl, said phenyl being optionally substituted 1 to 3 times with $R_{34}$; wherein
$R_{33}$ and $R_{33}'$ are both $C_{1-3}$-alkyl, or $R_{33}$ and $R_{33}'$ together with the nitrogen, to which they are attached, form a saturated 5 or 6 membered heterocyclic ring optionally comprising one further heteroatom selected from N, O, and S;
each $R_{34}$ is independently selected from the group consisting of $NR_{35}R_{35}'$, hydroxy and $C_{1-6}$-alkoxy; or two adjacent $R_{34}$ together with the carbon atoms, to which they are attached, form a 5 or 6 membered fused heterocyclic ring comprising 1 or 2 heteroatom(s) each independently selected from N, O and S;
wherein $R_{35}$ and $R_{35}'$ are both H or $C_{1-6}$-alkyl; or $R_{35}$ and $R_{35}'$ together with the nitrogen, to which they are attached, form a 5 or 6 membered saturated heterocyclic ring optionally further comprising as a ring member O, S, N, or $NR_{36}$, wherein $R_{36}$ is H, $C_{1-6}$-alkyl or benzoyl;
$R_4$ is selected from the group consisting of —CN; —C(=O)$X_4R_{41}$; phenyl, wherein said phenyl is optionally substituted with $R_{42}$; and an 5 or 6 membered unsaturated heterocyclic ring having 1 to 4 heteroatoms each independently selected from N, O and S and being optionally substituted one or more times with $R_{43}$;
wherein
$X_4$ is NH; and
$R_{41}$ is selected from the group consisting of H, $C_{1-6}$-alkyl, $R_{44}R_{44}'N$—$C_{1-6}$-alkylenyl, and —$NHR_{45}$,
wherein $R_{44}$ and $R_{44}'$ are both H or $C_{1-6}$-alkyl; or $R_{44}$ and $R_{44}'$ together with the nitrogen, to which they are attached, form a 5 or 6 membered saturated heterocyclic ring; and
$R_{45}$ is H or imino-$C_{1-6}$-alkyl; or
$X_4$ and $R_{41}$ taken together form —N=$CR_{46}R_{47}$, wherein
$R_{46}$ is H or methyl, and
$R_{47}$ is di($C_{1-3}$-alkyl)amino;
$R_{42}$ is selected from the group consisting of halogen, halo-$C_{1-3}$-alkyl, and $C_{1-6}$-alkoxy;
each $R_{43}$ is independently selected from the group consisting of —OH, —SH, and methyl;
excluding 5-phenoxy-2-phenyl-6-(1H-1,2,4-triazol-3-yl)pyridazin-3(2H)-one.

2. The pyridazinone compound according to claim 1, wherein $R_2$ is hydrogen, or pharmaceutically acceptable salt, hydrate, or solvate thereof.

3. The pyridazinone compound according to claim 1, wherein $R_1$ is unsubstituted phenyl, or pharmaceutically acceptable salt, hydrate, or solvate thereof.

4. The pyridazinone compound according to claim 1, wherein $X_3$ is O and $R_3$ is phenoxy, wherein said phenoxy is optionally substituted with $R_{31}$, or pharmaceutically acceptable salt, hydrate, or solvate thereof.

5. The pyridazinone compound according to claim 1, wherein $X_3$ is $NR_3'$.

6. The pyridazinone compound according to claim 5, wherein $NR_3'$ forms together with $R_3$ a group selected from the group consisting of N-methyl piperazinyl, pyrrolidinyl, and optionally substituted 1,2,3-triazolyl.

7. The pyridazinone compound according to claim 5, wherein $R_3$ is H, and $R_3$ is selected from a group consisting of H, $C_{1-6}$-alkyl, $C_{3-6}$-cycloalkyl, benzyl, $R_{33}R_{33}'N-C_{1-6}$-alkylenyl, pyrrolidinyl and N-methyl piperidinyl, or pharmaceutically acceptable salt, hydrate, or solvate thereof.

8. The pyridazinone compound according to claim 5, wherein $R_3'$ is H, and $R_3$ is optionally substituted phenyl, or pharmaceutically acceptable salt, hydrate, or solvate thereof.

9. The pyridazinone compound according to claim 8, wherein $R_{34}$ is selected from this group consisting of dimethylamino, methoxy piperidinyl, N-methyl piperazinyl, N-benzoyl piperazinyl, and morpholinyl, or pharmaceutically acceptable salt, hydrate, or solvate thereof.

10. The pyridazinone compound according to claim 1, wherein $R_4$, is 1,2,3-triazolyl or 1,2,4-triazolyl, or pharmaceutically acceptable salt, hydrate, or solvate thereof.

11. The pyridazinone compound according to claim 1, wherein the said compound is selected from the following compounds:

2-(4-chlorophenyl)-5-phenoxy-6-(1H-1,2,4-triazol-3-yl)-3(2H)-pyridazinone;
5-isopropylamino-2-phenyl-6-(1H-1,2,4-triazol-3-yl)-3 (2H)-pyridazinone;
5-cyclohexylamino-2-phenyl-6-(1H-1,2,4-triazol-3-yl)-3 (2H)-pyridazinone;
2-(4-chlorophenyl)-5-[(4-methoxyphenyl)amino]-6-(1H-1,2,4-triazol-3-yl)-3(2H)-pyridazinone;
2-(4-chlorophenyl)-5-[(3,4 methylenedioxyphenyl) amino]-6-(1H-1,2,4-triazol-3-yl)-3(2H)-pyridazinone;
2-(4-chlorophenyl)-5-{[4-(4-methylpiperazine-1-yl)phenyl]amino}-6-(1H-1,2,4-triazol-3-yl)-3(2H)-pyridazinone;
2-(4-chlorophenyl)-5-{[(4-(N,N-dimethylamino)phenyl] amino}-6-(1H-1,2,4-triazol-3-yl)-3(2H)-pyridazinone;
2-(4-chlorophenyl)-5-[(N-methylpiperidin-4-yl)amino]-6-(1H-1,2,4-triazol-3-yl)-3 (2H)-pyridazinone;
2-(4-chlorophenyl)-5-{[4-(4-piperazine-1-yl)phenyl] amino}-6-(1H-1,2,4-triazol-3-yl)-3 (2H)-pyridazinone;

or pharmaceutically acceptable salt, hydrate, or solvate thereof.

12. A pharmaceutically composition comprising an effective amount of one or more of the pyridazinone compound(s) of formula (I) as claimed in claim 1 in combination with one or more pharmaceutically acceptable excipient(s) and/or with other active ingredients.

13. A process for the preparation of the pyridazinone compound of formula (I') as claimed in claim 1, wherein X, $R_1$ $X_3$, and $R_3$ are as defined in claim 1, $R_2$ is H, and $R_4$ is optionally substituted phenyl or 5 to 6 membered heterocyclic ring, comprising reacting a compound of formula (IIb)

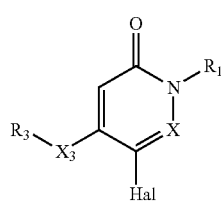

(IIb)

with a compound of formula (IIIb),

(IIIb)

wherein R' is alkyl and $R_4'$ is optionally substituted phenyl or 5 to 6 membered heterocyclic ring.

14. A process for the preparation of the pyridazinone compound of formula (I') as claimed in claim 1, wherein X is N and $R_1$ is as claimed in claim 1, $R_2$ is H, $X_3R_3$ is OH and $R_4$ is —C(=O)$X_4R_{41}$ as defined in claim 1, comprising reacting a compound of formula (IV),

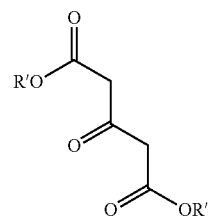

(IV)

wherein R' is alkyl, with a compound of formula (IIIc),

(IIIc)

wherein $R_1$ is as defined In claim 1 and A is anion, and heating the obtained compound, to obtain a first compound of formula (I') wherein $X_4$ is O and $R_{41}$ is alkyl, and reacting the obtained compound with acid, to obtain a second compound of formula (I') wherein $X_4$ is O and $R_{41}$ is H, and reacting the said second compound with compound of formula (V),

(V)

wherein $R_{41}$ is as defined in claim 1, to obtain a third compound of formula (I'), wherein $X_4$ is NH and $R_{41}$ is as defined in claim 1.

15. A process for the preparation of the pyridazinone compound of general formula (I') as claimed in claim 1, wherein X, $R_1$, $R_2$, and $R_4$ are as defined in claim 1 and $X_3$ is S, O or $NR_3'$ and $R_3$ is as defined in claim 1, or $X_3$ and $R_3$ form together $N_3$, comprising reacting a compound of formula (IId),

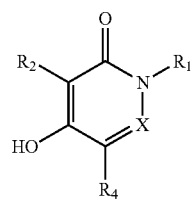

(IId)

wherein X is CH, with POCl$_3$ and reacting the thus obtained compound with NaN$_3$, or with a compound of formula (IIId),

(IIId)

wherein X₃ is S or O and R₃ are as defined claim 1, to obtain a first compound of formula (I'), wherein R₃ is N₃ or X₃ is O or S and R₃₁ is as defined in claim 1, respectively, and, if desired, reacting the said first compound, wherein X₃R₃ is alkoxy with a compound of formula (VIId), R₃R₃'NH (VIId)

wherein R₃ and R₃' are as defined claim 1, to obtain a second compound of formula (I'), wherein X₃ is NR₃' and R₃ is as defined in claim 1.

16. A method for inhibiting SSAO/VAP-1 in an in vitro test method, comprising:
 administering a pyridazinone compound of formula (I), or pharmaceutically acceptable salt, hydrate, or solvate thereof in vitro to SSAO/VAP-1, wherein the formula (I) is:

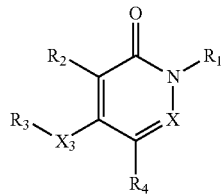
(I)

wherein
 X is N;
 R₁ is phenyl, optionally substituted with R₁₁,
 wherein R₁₁ is selected from the group consisting of halogen, halo-C₁₋₃-alkyl, and C₁₋₆-alkoxy;
 R₂ is H or triazolyl;
 (i) X₃ is O or S, and
 R₃ is selected from the group consisting of H, C₁-C₆-alkyl, C₂₋₆-alkenyl, and phenyl, said phenyl being optionally substituted one or more times with R₃₁, each R₃₁ is independently selected from the group consisting of halogen, halo-C₁₋₃-alkyl and C₁₋₆-alkoxy; or
 (ii) X₃ is NR₃', and
 R₃ and R₃' together with the nitrogen, to which they are attached, form a 5 or 6 membered saturated heterocyclic ring, —N₃, or triazole, said triazole being optionally substituted with R₃₂, wherein R₃₂ is selected from the group consisting of phenyl, C₁₋₆-alkyl, and —CO₂(C₁₋₃-alkyl); or
 R₃' is H or C₁₋₃-alkyl, and
 R₃ is selected from the group consisting of H; C₁₋₆-alkyl; C₂₋₆-alkenyl; C₂₋₆-alkynyl; C₃₋₆-cycloalkyl-C₁₋₆-alkyl; C₃₋₆-cycloalkyl C₁₋₆-cycloalkyl; cyano-C₁₋₆-alkyl; amino-C₁₋₆-alkyl; benzyl; pyridyl; saturated 5 or 6 membered heterocyclic ring having 1 to 2 heteroatoms selected from N, O, and S, and wherein said N is optionally substituted with C₁₋₆-alkyl; R₃₃R₃₃'N—C₁₋₆-alkylenyl; and phenyl, said phenyl being optionally substituted 1 to 3 times with R₃₄;
 wherein
 R₃₃ and R₃₃' are both C₁₋₃-alkyl, or R₃₃ and R₃₃' together with the nitrogen, to which they are attached, form a saturated 5 or 6 membered heterocyclic ring optionally comprising one further heteroatom selected from N, O, and S;
 each R₃₄ is independently selected from the group consisting of NR₃₅R₃₅', hydroxy and C₁₋₆-alkoxy; or two adjacent R₃₄ together with the carbon atoms, to which they are attached, form a 5 or 6 membered fused heterocyclic ring comprising 1 or 2 heteroatom(s) each independently selected from N, O and S;
 wherein R₃₅ and R₃₅' are both H or C₁₋₆-alkyl; or R₃₅ and R₃₅' together with the nitrogen, to which they are attached, form a 5 or 6 membered saturated heterocyclic ring optionally further comprising as a ring member O, S, N, or NR₃₆, wherein R₃₆ is H, C₁₋₆-alkyl or benzoyl;
 R₄ is selected from the group consisting of —CN, —C(=O)X₄R₄₁; phenyl, wherein said phenyl is optionally substituted with R₄₂; and an 5 or 6 membered unsaturated heterocyclic ring having 1 to 4 heteroatoms each independently selected from N, O and S and being optionally substituted one or more times with R₄₃;
 wherein
 X₄ is NH; and
 R₄₁ is selected from the group consisting of H, C₁₋₆-alkyl, R₄₄R₄₄'N—C₁₋₆-alkylenyl, and —NHR₄₂;
 wherein R₄₄ and R₄₄' are both H or C₁₋₆-alkyl; or R₄₄ and R₄₄' together with the nitrogen, to which they are attached, form a 5 or 6 membered saturated heterocyclic ring; and
 R₄₅ is H or imino-C₁₋₆-alkyl; or
 X₄ and R₄₁ taken together form —N=CR₄₆R₄₇, wherein R₄₆ is H or methyl, and
 R₄₇ is di(C₁₋₃-alkyl)amino;
 R₄₂ is selected from the group consisting of halogen, halo-C₁₋₃-alkyl, and C₁₋₆-alkoxy; each R₄₃ is independently selected from the group consisting of —OH, —SH, and methyl.

17. A method for treatment of a SSAO/VAP-1 related disease in a patient, comprising:
 administering a pyridazinone compound of formula (I) or pharmaceutically acceptable salt, hydrate, or solvate thereof to the patient suffering from the SSAO/VAP-1 related disease selected from the group consisting of diabetic kidney disease, renal fibrosis, neoiridmal and medial fibrosis liver fibrosis, collagen-induced arthritis, autoimmune encephalitis and lung inflammation, wherein the formula (I) is:

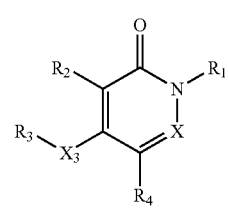
(I)

wherein
 X is N;
 R₁ is phenyl, optionally substituted with R₁₁,
 wherein R₁₁ is selected from the group consisting of halogen, halo-C₁₋₃-alkyl, and C₁₋₆-alkoxy;
 R₂ is H or triazolyl;
 (i) X₃ is O or S, and
 R₃ is selected from the group consisting of H, C₁-C₆-alkyl, C₂₋₆-alkenyl, and phenyl, said phenyl being optionally substituted one or more times with R₃₁, each R₃₁, is independently selected from the group consisting of halogen, halo-C₁₋₃-alkyl and C₁₋₆-alkoxy; or
 (ii) X₃ is NR₃', and
 R₃ and R₃' together with the nitrogen, to which they are attached, form a 5 or 6 membered saturated heterocyclic ring, —Na, or triazole, said triazole being optionally substituted with $R_{32}$, wherein $R_{32}$ is selected from the group consisting of phenyl, $C_{1-6}$-alkyl, and —$CO_2(C_{1-3}$-alkyl); or $R_3'$ is H or $C_{1-3}$-alkyl, and $R_3$ is selected from the group consisting of H; $C_{1-6}$-alkyl; $C_{2-6}$-aikenyl; $C_{2-6}$-alkynyl; $C_{3-6}$-cycloalkyl-$C_{1-6}$-alkyl; $C_{3-6}$-cycloalkyl $C_{1-6}$-cycloalkyl; cyano-$C_{1-6}$-alkyl; amino-$C_{1-6}$-alkyl; benzyl; pyridyl; saturated 5 or 6 membered heterocyclic ring having 1 to 2 heteroatoms selected from N, O, and S, and wherein said N is optionally substituted with $C_{1-6}$-alkyl; $R_{33}R_{33}'$N—$C_{1-6}$-alkylenyl; and phenyl, said phenyl being optionally substituted 1 to 3 times with $R_{34}$;

wherein $R_{33}$ and $R_{33}'$ art both $C_{1-3}$-alkyl; or $R_{33}$ and $R_{33}'$ together with the nitrogen, to which they are attached, form a saturated 5 or 6 membered heterocyclic ring optionally comprising one further heteroatom selected from N, O, and S;

each $R_{34}$ is independently selected from the group consisting of $NR_{35}R_{35}'$, hydroxy and $C_{1-6}$-alkoxy; or two adjacent $R_{34}$ together with the carbon atoms, to which they are attached, form a 5 or 6 membered fused heterocyclic ring comprising 1 or 2 heteroatom(s) each independently selected from N, O and S;

wherein $R_{35}$ and $R_{35}'$ are both H or $C_{1-6}$-alkyl; or $R_{35}$ and $R_{35}'$ together with the nitrogen, to which they are attached, form a 5 or 6 membered saturated heterocyclic ring optionally further comprising as a ring member O, S, N, or $NR_{36}$, wherein $R_{36}$ is H, $C_{1-6}$-alkyl or benzoyl;

$R_4$ is selected from the group consisting of —CN; —C(=O)$X_4R_{41}$; phenyl, wherein said phenyl is optionally substituted with $R_{42}$; and an 5 or 6 membered unsaturated heterocyclic ring having 1 to 4 heteroatoms each independently selected from N, O and S and being optionally substituted one or more times with $R_{43}$;

wherein $X_4$ is NH; and $R_{41}$ is selected from the group consisting of H, $C_{1-6}$-alkyl, $R_{44}R_{44}'$N—$C_{1-6}$-alkylenyl, and —$NHR_{45}$;

wherein $R_{44}$ and $R_{44}'$ are both H or $C_{1-6}$-alkyl; or $R_{44}$ and $R_{44}'$ together with the nitrogen, to which they are attached, form a 5 or 6 membered saturated heterocyclic ring; and $R_{45}$ is H or imino-$C_{1-6}$-alkyl; or $X_4$ and $R_{41}$ taken together form —N=$CR_{46}R_{47}$, wherein $R_{46}$ is H or methyl, and $R_{47}$ is di($C_{1-3}$-alkyl)amino;

$R_{42}$ is selected from the group consisting of halogen, halo-$C_{1-3}$-alkyl, and $C_{1-6}$-alkoxy;

each $R_{43}$ is independently selected from the group consisting of —OH, —SH, and methyl.

* * * * *